US011767552B2

(12) United States Patent
Eisenhower et al.

(10) Patent No.: US 11,767,552 B2
(45) Date of Patent: Sep. 26, 2023

(54) MULTI-FUNCTION ANALYTIC DEVICES

(71) Applicant: Biomeme, Inc., Philadelphia, PA (US)

(72) Inventors: Peter Eisenhower, Downingtown, PA (US); Tom Cook, Downingtown, PA (US); Max Perelman, Philadelphia, PA (US)

(73) Assignee: BIOMEME, INC., Philadelphia, PA (US)

( * ) Notice: Subject to any disclaimer, the term of this patent is extended or adjusted under 35 U.S.C. 154(b) by 0 days.

(21) Appl. No.: 17/479,391

(22) Filed: Sep. 20, 2021

(65) Prior Publication Data
US 2022/0074847 A1 Mar. 10, 2022

Related U.S. Application Data

(63) Continuation of application No. PCT/US2020/023630, filed on Mar. 19, 2020.

(60) Provisional application No. 62/821,652, filed on Mar. 21, 2019.

(51) Int. Cl.
C12Q 1/6848 (2018.01)
G01N 35/00 (2006.01)
G01N 21/03 (2006.01)
G01N 21/64 (2006.01)

(52) U.S. Cl.
CPC ..... *C12Q 1/6848* (2013.01); *G01N 35/00871* (2013.01); *G01N 21/0332* (2013.01); *G01N 21/6428* (2013.01); *G01N 2021/6421* (2013.01); *G01N 2035/00881* (2013.01); *G01N 2201/0221* (2013.01)

(58) Field of Classification Search
CPC ... G01N 2021/6421; G01N 2021/6441; G01N 2035/00881; G01N 21/0332; G01N 21/6428; G01N 2201/0221; G01N 35/00871; B01L 7/52; C12Q 1/6848
See application file for complete search history.

(56) References Cited

U.S. PATENT DOCUMENTS

| 3,757,780 | A | 9/1973 | Ishikawa |
| 5,529,391 | A | 6/1996 | Kindman et al. |
| 5,616,301 | A | 4/1997 | Moser et al. |
| 5,849,488 | A | 12/1998 | Alatossava et al. |
| 6,746,864 | B1 | 6/2004 | McNeil et al. |
| 7,167,755 | B2 | 1/2007 | Seeberger et al. |
| 8,361,316 | B2 | 1/2013 | Siddiqi |
| 8,940,524 | B2 | 1/2015 | Cobb |
| 9,535,676 | B1 | 1/2017 | Forehand et al. |
| 9,579,655 | B2 | 2/2017 | Dejohn et al. |
| 9,618,139 | B2 | 4/2017 | Handique |
| 10,036,058 | B2 | 7/2018 | Baumgartner et al. |
| 10,457,983 | B2 | 10/2019 | Dejohn et al. |
| 2001/0003652 | A1 | 6/2001 | Freeman |
| 2001/0012612 | A1 | 8/2001 | Petersen et al. |
| 2002/0150907 | A1 | 10/2002 | Fomovskaia et al. |
| 2004/0126279 | A1 | 7/2004 | Renzi et al. |
| 2005/0033196 | A1 | 2/2005 | Alroy |
| 2006/0001870 | A1 | 1/2006 | Voigt et al. |
| 2006/0222567 | A1 | 10/2006 | Kloepfer et al. |
| 2007/0035732 | A1 | 2/2007 | Marsche et al. |
| 2008/0145848 | A1 | 6/2008 | Stephan et al. |
| 2008/0145858 | A1 | 6/2008 | Kim et al. |
| 2008/0254532 | A1 | 10/2008 | Chang et al. |
| 2009/0142333 | A1 | 6/2009 | Knopf et al. |
| 2009/0143233 | A1 | 6/2009 | Knight et al. |
| 2010/0177950 | A1 | 7/2010 | Donovan et al. |
| 2011/0057117 | A1 | 3/2011 | Fawcett et al. |
| 2011/0076735 | A1 | 3/2011 | Jovanovich et al. |
| 2011/0290647 | A1 | 12/2011 | Feiglin |
| 2012/0077259 | A1 | 3/2012 | Cobb |
| 2012/0220024 | A1 | 8/2012 | Cobb |
| 2012/0288892 | A1 | 11/2012 | Maiyuran et al. |
| 2012/0288897 | A1 | 11/2012 | Ching et al. |
| 2013/0115607 | A1 | 5/2013 | Nielsen et al. |
| 2013/0230845 | A1 | 9/2013 | Egan et al. |
| 2014/0008311 | A1 | 1/2014 | Weston et al. |
| 2014/0206412 | A1 | 7/2014 | DeJohn et al. |

(Continued)

FOREIGN PATENT DOCUMENTS

| CN | 1680574 A | 10/2005 |
| CN | 1687391 A | 10/2005 |

(Continued)

OTHER PUBLICATIONS

European Examination Report dated Oct. 8, 2018, for EP Appl. 14740636.7.
European search report with written opinion dated Aug. 22, 2016 for EP14740636.
International Search Report and Written Opinion for corresponding PCT Application No. PCT/US2020/023630 dated Jun. 16, 2020.
"International search report with written opinion dated May 23, 2014 for PCT/US2014/012308.".

(Continued)

*Primary Examiner* — Young J Kim
(74) *Attorney, Agent, or Firm* — Wilson Sonsini Goodrich & Rosati

(57) ABSTRACT

The present disclosure provides devices, systems, methods for processing and/or analyzing a biological sample. An analytic device for processing and/or analyzing one or more biological samples may be electronically and/or physically configured or programed to activate one or more features/operations of the analytic device. The analytic device can be configured or programed by one or more instructions received from a cooperating electronic device or a remote server. The analytic device may comprise a moving carriage. The analytic device may be portable. The analytic device may receive instructions for performing an assay from a mobile electronic device external to a housing of the analytic device.

24 Claims, 37 Drawing Sheets

(56) References Cited

U.S. PATENT DOCUMENTS

| | | |
|---|---|---|
| 2015/0024436 A1 | 1/2015 | Eberhart et al. |
| 2015/0111287 A1* | 4/2015 | Rawle .................... C12Q 1/701 422/69 |
| 2016/0041095 A1 | 2/2016 | Rothberg et al. |
| 2016/0069921 A1 | 3/2016 | Holmes et al. |
| 2016/0115520 A1 | 4/2016 | Krishnamurthy |
| 2016/0155120 A1 | 6/2016 | Hurry |
| 2016/0169924 A1 | 6/2016 | Torgerson et al. |
| 2016/0230210 A1 | 8/2016 | Chen et al. |
| 2016/0231171 A1 | 8/2016 | Assefa et al. |
| 2016/0265040 A1 | 9/2016 | Baumgartner et al. |
| 2017/0068533 A1 | 3/2017 | Kiaie et al. |
| 2017/0183713 A1 | 6/2017 | DeJohn et al. |
| 2017/0327867 A1 | 11/2017 | Dohale et al. |
| 2017/0333894 A1 | 11/2017 | Khalid et al. |
| 2020/0276582 A1 | 9/2020 | DeJohn et al. |
| 2020/0376494 A1* | 12/2020 | DeJohn ................ G01N 21/645 |
| 2022/0186325 A1* | 6/2022 | DeJohn ............. B01L 3/502715 |

FOREIGN PATENT DOCUMENTS

| | | |
|---|---|---|
| CN | 101868721 A | 10/2010 |
| CN | 102348985 A | 2/2012 |
| CN | 202379991 U | 8/2012 |
| CN | 104919035 A | 9/2015 |
| CN | 105092543 A | 11/2015 |
| EP | 1704922 A2 | 9/2006 |
| JP | 2013525763 A | 6/2013 |
| WO | WO-2004045772 A2 | 6/2004 |
| WO | WO-2009036956 A1 | 3/2009 |
| WO | WO-2009047804 A2 | 4/2009 |
| WO | WO-2011106315 A1 | 9/2011 |
| WO | WO-2011106384 A1 | 9/2011 |
| WO | WO-2011130629 A1 | 10/2011 |
| WO | WO-2013010178 A1 | 1/2013 |
| WO | WO-2013052318 A1 | 4/2013 |
| WO | WO-2014100725 A1 | 6/2014 |
| WO | WO-2014113785 A1 | 7/2014 |
| WO | WO-2015054245 A1 | 4/2015 |
| WO | WO-2019055875 | 3/2019 |
| WO | WO-2019118343 A2 | 6/2019 |
| WO | WO-2019143812 A1 | 7/2019 |
| WO | WO-2020257297 A1 | 12/2020 |
| WO | WO-2022061105 A1 | 3/2022 |

OTHER PUBLICATIONS

ISR/WO dated Apr. 19, 2019 for PCT/US18/064736.
ISR/WO dated May 23, 2019 for PCT/US19/14005.
Non-Final Office Action dated, Sep. 4, 2019 for U.S. Appl. No. 15/682,675.
Notice of allowance dated Jan. 17, 2017 for U.S. Appl. No. 14/159,844.
Notice of allowance dated Oct. 12, 2016 for U.S. Appl. No. 14/159,844.
Office action dated May 5, 2017 for U.S. Appl. No. 14/159,844.
Office action dated Nov. 5, 2015 for U.S. Appl. No. 14/159,844.
Office Action dated Jul. 27, 2016 issued in the corresponding Chinese Patent Application No. 201480010760.9.
Mar. 29, 2022 Final Office Action U.S. Appl. No. 16/571,535.
Jun. 15, 2022 Non-Final Office Action U.S. Appl. No. 16/899,810.
Sep. 15, 2021 Non-Final Office Action U.S. Appl. No. 16/571,535.
Sep. 30, 2022 Final Office Action U.S. Appl. No. 16/571,535.
European Examination Report dated Aug. 4, 2021, for EP Application No. 18888874.7.
International Preliminary Report on Patentability dated Jul. 21, 2015 for International Application No. PCT/US2014/012308.
International Preliminary Report on Patentability dated Jul. 21, 2020 for International Application No. PCT/US2019/014005.
International Preliminary Report on Patentability dated Jun. 16, 2020 for International Application No. PCT/US2018/064736.
International Preliminary Report on Patentability for PCT/US2020/038159 dated Dec. 30, 2021.
International Search Report and Written Opinion dated May 23, 2019 for International Application No. PCT/US2019/014005.
International Search Report and Written Opinion for PCT/US2020/038159 dated Oct. 14, 2020.
International Search Report and Written Opinion for PCT/US2021/050862 dated Dec. 30, 2021.
Notice of allowance dated Sep. 11, 2019 for U.S. Appl. No. 15/436,080.
Notice of allowance dated Jun. 27, 2019 for U.S. Appl. No. 15/436,080.
Extended European Search Report dated Oct. 14, 2022 for EP20774341.0.

\* cited by examiner

```
┌─────────────────────────────────────────────────┐
│ Provide an analytic device comprising an optical detector    │─── 2301
│ configured to detect optical signals from a first biological │
│ sample over a plurality of optical frequencies comprising a  │
│ first set of optical frequencies and a second set of optical │
│ frequencies different than the first set of optical frequencies, │
│ wherein the analytic device is programmed to output data     │
│ corresponding to the first set of optical frequencies but not│
│ output data corresponding to the second set of optical       │
│ frequencies when assaying the first biological sample        │
└─────────────────────────────────────────────────┘
                          │
┌─────────────────────────────────────────────────┐
│ Receive, over a network, one or more instructions from a     │─── 2302
│ remote server, which one or more instructions are usable to  │
│ program the analytic device to output data corresponding to  │
│            the second set of optical frequencies             │
└─────────────────────────────────────────────────┘
                          │
┌─────────────────────────────────────────────────┐
│ Use the one or more instructions to program the analytic     │─── 2303
│      device such that the analytic device output data        │
│ corresponding to at least the first set of optical frequencies│
│ and the second set of optical frequencies when assaying a    │
│                  second biological sample                    │
└─────────────────────────────────────────────────┘
```

FIG. 23

```
┌─────────────────────────────────────────────────────┐
│ Provide an analytic device configured to perform a  │
│ first assay and a second assay on a first           │── 2401
│ biological sample, wherein the second assay is      │
│ different from the first assay, and wherein the     │
│ analytic device is programmed to output data        │
│ corresponding to the first assay but not output     │
│ data corresponding to the second assay              │
└─────────────────────────────────────────────────────┘
                          │
┌─────────────────────────────────────────────────────┐
│ Receive, over a network, one or more instructions   │
│ from a remote server, which one or more             │
│ instructions are usable to program the analytic     │── 2402
│ device to output data corresponding to              │
│ the second assay                                    │
└─────────────────────────────────────────────────────┘
                          │
┌─────────────────────────────────────────────────────┐
│ Use the one or more instructions to program the     │
│ analytic device such that the analytic device       │
│ output data corresponding to at least the first     │── 2403
│ assay and the second assay when assaying a          │
│ second biological sample                            │
└─────────────────────────────────────────────────────┘
```

FIG. 24

MULTI-FUNCTION ANALYTIC DEVICES

CROSS-REFERENCE

This application is a continuation of International Application No. PCT/US20/23630 filed Mar. 19, 2020 which claims priority to U.S. Provisional Patent Application No. 62/821,652, filed Mar. 21, 2019, which is entirely incorporated herein by reference.

BACKGROUND

Nucleic acid-based amplification reactions are now widely used in research and clinical laboratories for the detection of genetic and infectious diseases. The devices and systems may be provided to perform these amplification reactions. Sometimes, there may be multiple targets need to be amplified or detected in a sample. Devices that are capable for performing multiplexed assays may be provided.

SUMMARY

Recognized herein is a need for an example analytic device operatively used for analyzing biological samples having one or more electronic/physical throttles that are illustratively operative to activate/unlock one or more features/operations of the example analytic device. The present disclosure provides apparatus, methods and systems for electronically and/or physically configuring or programming an example analytic device such that one or more additional features/operations of the analytical device can be activated on the same device without the need for a change of the hardware and/or software of the device. Moreover, devices that have electronic/physical throttles to activate one or more device features/operations are provided in the present disclosure.

In an aspect, the present disclosure provides a method for programming an analytic device, comprising: (a) providing the analytic device comprising an optical detector configured to detect optical signals from a first biological sample over a plurality of optical frequencies comprising a first set of optical frequencies and a second set of optical frequencies different than the first set of optical frequencies, wherein the analytic device is programmed to output data corresponding to the first set of optical frequencies but not output data corresponding to the second set of optical frequencies when assaying the first biological sample; (b) receiving, over a network, one or more instructions from a remote server, which one or more instructions are usable to program the analytic device to output data corresponding to the second set of optical frequencies; and (c) using the one or more instructions to program the analytic device such that the analytic device outputs data corresponding to at least the first set of optical frequencies and the second set of optical frequencies when assaying a second biological sample.

In some embodiments, the analytic device comprises a housing. In some embodiments, the housing has a volume that is less than about 1,500 cubic centimeters. In some embodiments, the housing has a volume that is more than about 1,500 cubic centimeters. In some embodiments, the analytic device comprises at least one heating block within the housing, the at least one heating block comprising a recess configured to receive an assay tube comprising the first or second biological sample. In some embodiments, the analytic device comprises at least one heating unit in thermal communication with the at least one heating block, which at least one heating unit provides thermal energy to the assay tube through the at least one heating block. In some embodiments, the at least one heating unit comprises a resistive heater. In some embodiments, the at least one heating unit is (i) thermally cured to the at least one heating block, or (ii) soldered to the at least one heating block. In some embodiments, the analytic device further comprises a cooling unit disposed within the housing, which cooling unit reduces the thermal energy from the assay tube. In some embodiments, the first set of optical frequencies comprises a first color and the second set of optical frequencies comprises a second color different than the first color. In some embodiments, the analytic device comprises a lighting unit, which lighting unit comprises at least one light path comprising an excitation filter and an emission filter, wherein the at least one light path is configured to provide excitation energy from a light source to the first or second biological sample. In some embodiments, the at least one light path comprises one or more light pipes to convey the excitation energy from the light source to the first or second biological sample. In some embodiments, the one or more light pipes comprise a first end comprising a single pipe, a second end comprising two or more pipes, and a branching portion therebetween. In some embodiments, the analytic device comprises a lighting unit comprising a plurality of light sources configured to provide excitation energy at a plurality of different frequencies or frequency ranges, wherein the lighting unit is configured to bring a light source of the plurality of light sources in optical alignment with a light path that is in optical communication with the first or second biological sample, which light source is configured to provide light at a frequency or frequency range from the plurality of different frequencies or frequency ranges. In some embodiments, the lighting unit is rotatable along an axis. In some embodiments, the lighting unit is translatable along an additional axis orthogonal to the axis, wherein the lighting unit is translatable along the additional axis to remove the light path from alignment with the first or second biological sample. In some embodiments, the analytic device comprises a movable carriage comprising an excitation filter and an emission filter, wherein the movable carriage is configured to translate to bring the excitation filter and the emission filter to a first position in alignment with a light path that provides excitation energy from the excitation source to the first or second biological sample. In some embodiments, the movable carriage comprises a plurality of light paths. In some embodiments, the analytic device further comprises an actuator for moving the movable carriage from the first position to a second position. In some embodiments, the light source is an excitation source. In some embodiments, the excitation source comprises one or more light emitting diodes (LEDs). In some embodiments, the one or more LEDs comprise single-color LEDs. In some embodiments, the one or more LEDs comprise a plurality of LEDs, and each of the plurality of LEDs is configured to emit a different frequency of the excitation energy.

In some embodiments, the method further comprises, subsequent to (a), assaying the first biological sample. In some embodiments, the assaying comprising detecting the first set of optical frequencies and/or the second set of optical frequencies. In some embodiments, the method further comprises receiving an error signal indicative of inability to output the second set of optical frequencies when detecting the second set of optical frequencies.

In some embodiments, the method further comprises, prior to (b), directing a request to the remote server for the one or more instructions.

In some embodiments, the analytic device further comprises a processing unit comprising a circuit within the housing, which processing unit is configured to communicate with a mobile electronic device external to the housing. In some embodiments, the analytic device further comprises a communication unit that provides wireless connection between the processing unit and the mobile electronic device. In some embodiments, the wireless connection is a WiFi connection, a Bluetooth connection, a Bluetooth LE connection, an ANT+ connection, or a Gazell connection.

In some embodiments, the method further comprises using the mobile electronic device to (i) direct the request to the remote server for the one or more instructions, and (ii) receive the one or more instructions from the remote server. In some embodiments, (c) further comprising, upon receiving the one or more instructions, using the mobile electronic device to send instructions to the processing unit to program the analytic device. In some embodiments, the mobile electronic device is a phone, a laptop, a computer, or an iPad. In some embodiments, the phone is a smart phone. In some embodiments, the mobile electronic device is a device that can perform wireless communication with the analytic device.

In some embodiments, the processing unit is configured to: receive instructions from the mobile electronic device external to the housing for processing the first or second biological sample; and in response to the instructions, (i) direct the at least one heating unit to provide thermal energy to the at least one heating block to provide heat to the first or second biological sample, and (ii) direct the excitation source to provide the excitation energy. In some embodiments, in (c), the one or more instructions are used to program the analytic device such that the analytic device outputs data corresponding to at least the first set of optical frequencies, the second set of optical frequencies and a third set of optical frequencies when assaying a second biological sample, wherein the third set of optical frequencies is different than the first set of optical frequencies and the second set of optical frequencies. In some embodiments, the optical signals comprise emission energy.

In some embodiments, the method further comprises outputting data corresponding to at least the first set of optical frequencies and the second set of optical frequencies when assaying the second biological sample.

In another aspect, the present disclosure provides a system for biological sample assaying, comprising: an analytic device comprising an optical detector configured to detect optical signals from a first biological sample over a plurality of optical frequencies comprising a first set of optical frequencies and a second set of optical frequencies different than the first set of optical frequencies, wherein the analytic device is programed to output data corresponding to the first set of optical frequencies but not output data corresponding to the second set of optical frequencies when assaying the first biological sample; one or more computer processors operatively coupled to the analytic device, wherein the one or more computer processors are individually or collectively programmed to (i) receive, over a network, one or more instructions from a remote server, which one or more instructions are usable by the one or more computer processors to program the analytic device to output data corresponding to the second set of optical frequencies, and (ii) use the one or more instructions to program the analytic device such that the analytic device outputs data corresponding to the first set of optical frequencies and the second set of optical frequencies when assaying a second biological sample. In some embodiments, the system further comprises a housing, wherein the analytic device and the one or more computer processors are within the housing. In some embodiments, the system further comprises a housing, wherein the analytic device is within the housing, and wherein the one or more computer processors are external to the housing. In some embodiments, the analytic device comprises a housing with a volume that is less than about 1,500 cubic centimeters. In some embodiments, the analytic device comprises at least one heating block within the housing, the at least one heating block comprising a recess configured to receive an assay tube comprising the first or second biological sample. In some embodiments, the analytic device comprises at least one heating unit in thermal communication with the at least one heating block, which at least one heating unit provides thermal energy to the assay tube through the at least one heating block. In some embodiments, the at least one heating unit comprises a resistive heater. In some embodiments, the at least one heating unit is (i) thermally cured to the at least one heating block, or (ii) soldered to the at least one heating block. In some embodiments, the analytic device further comprises a cooling unit disposed within the housing, which cooling unit reduces the thermal energy from the assay tube. In some embodiments, the first set of optical frequencies comprises a first color and the second set of optical frequencies comprises a second color different than the first color. In some embodiments, the analytic device comprises a lighting unit, which lighting unit comprises at least one light path comprising an excitation filter and an emission filter, wherein the at least one light path is configured to provide excitation energy from a light source to the first or second biological sample. In some embodiments, the at least one light path comprises one or more light pipes to convey the excitation energy from the light source to the first or second biological sample. In some embodiments, the one or more light pipes comprise a first end comprising a single pipe, a second end comprising two or more pipes, and a branching portion therebetween. In some embodiments, the analytic device comprises a lighting unit comprising a plurality of light sources configured to provide excitation energy at a plurality of different frequencies or frequency ranges, wherein the lighting unit is configured to bring a light source of the plurality of light sources in optical alignment with a light path that is in optical communication with the first or second biological sample, which light source is configured to provide light at a frequency or frequency range from the plurality of different frequencies or frequency ranges. In some embodiments, the lighting unit is rotatable along an axis. In some embodiments, the lighting unit is translatable along an additional axis orthogonal to the axis, wherein the lighting unit is translatable along the additional axis to remove the light path from alignment with the first or second biological sample. In some embodiments, the analytic device comprises a movable carriage comprising an excitation filter and an emission filter, wherein the movable carriage is configured to translate to bring the excitation filter and the emission filter to a first position in alignment with a light path that provides excitation energy from the excitation source to the first or second biological sample. In some embodiments, the movable carriage comprises a plurality of light paths. In some embodiments, the analytic device further comprises an actuator for moving the movable carriage from the first position to a second position. In some embodiments, the light source is an excitation source. In some embodiments, the excitation source comprises one or more light emitting diodes (LEDs). In some embodiments, the one or more LEDs comprise single-color LEDs. In some embodiments, the one or more LEDs comprise a plurality of LEDs, and each of the plurality of LEDs is configured to emit a different frequency of the excitation energy. In some embodiments, the one or more computer processors are configured to communicate with a mobile electronic device external to the housing. In some embodiments, the analytic device further comprises a communication unit that provides wireless connection between the one or more computer processors and the mobile electronic device. In some embodiments, the wireless connection is a WiFi connection, a Bluetooth connection, a Bluetooth LE connection, an ANT+ connection, or a Gazell connection. In some embodiments, the one or more computer processors are individually or collectively programmed to direct a request to the remote server for the one or more instructions. In some embodiments, the mobile electronic device is configured to (i) direct the request to the remote server for the one or more instructions, and (ii) receive the one or more instructions from the remote server. In some embodiments, the mobile electronic device is configured to send instructions to the one or more computer processors to program the analytic device upon receiving the one or more instructions. In some embodiments, the one or more computer processors are configured to: receive instructions from the mobile electronic device external to the housing for processing the first or second biological sample; and in response to the instructions, (i) direct the at least one heating unit to provide thermal energy to the at least one heating block to provide heat to the first or second biological sample, and (ii) direct the excitation source to provide the excitation energy. In some embodiments, the one or more computer processors are individually or collectively programmed to program the analytic device such that the analytic device outputs data corresponding to at least the first set of optical frequencies, the second set of optical frequencies and a third set of optical frequencies when assaying a second biological sample, wherein the third set of optical frequencies is different than the first set of optical frequencies and the second set of optical frequencies.

In another aspect, the present disclosure provides a method for programming an analytic device, comprising: (a) providing the analytic device configured to perform a first assay and a second assay on a first biological sample, wherein the second assay is different from the first assay, and wherein the analytic device is programmed to output data corresponding to the first assay but not output data corresponding to the second assay; (b) receiving, over a network, one or more instructions from a remote server, which one or more instructions are usable to program the analytic device to output data corresponding to the second assay; and (c) using the one or more instructions to program the analytic device such that the analytic device outputs data corresponding to at least the first assay and the second assay when assaying a second biological sample. In some embodiments, the first assay is a thermal cycling assay. In some embodiments, the thermal cycling assay comprises heating and cooling of the first or second biological sample. In some embodiments, the second assay is a melting curve assay. In some embodiments, the melting curve assay comprising heating the first or second biological sample over a range of temperatures at a temperature increment. In some embodiments, the temperature increment is at least about 0.1° C., about 0.2° C., about 0.3° C., about 0.4° C., about 0.5° C., about 0.6° C., about 0.7° C., about 0.8° C., about 0.9° C., about 1° C., or higher. In some embodiments, the first biological sample and the second biological sample are same. In some embodiments, the first biological sample and the second biological sample are different.

In another aspect, the present disclosure provides a system for biological sample assaying, comprising: an analytic device configured to perform a first assay and a second assay on a first biological sample, wherein the second assay is different from the first assay, and wherein the analytic device is configured to output data corresponding to the first assay but not output data corresponding to the second assay; one or more computer processors operatively coupled to the analytic device, wherein the one or more computer processors are individually or collectively programmed to (i) receive, over a network, one or more instructions from a remote server, which one or more instructions are usable by the one or more computer processors to program the analytic device to output data corresponding to the second assay, and (ii) use the one or more instructions to program the analytic device such that the analytic device outputs data corresponding to the first assay and the second assay when assaying a second biological sample. In some embodiments, the first assay is a thermal cycling assay. In some embodiments, the thermal cycling assay comprises heating and cooling of the first or second biological sample. In some embodiments, the second assay is a melting curve assay. In some embodiments, the melting curve assay comprising heating the first or second biological sample with a range of temperatures with a temperature increment. In some embodiments, the temperature increment is at least about 0.1° C., 0.2° C., 0.3° C., 0.4° C., 0.5° C., 0.6° C., 0.7° C., 0.8° C., 0.9° C., 1° C., or higher. In some embodiments, the first biological sample and the second biological sample are same. In some embodiments, the first biological sample and the second biological sample are different. In some embodiments, the system further comprises a housing, wherein the analytic device and the one or more computer processors are within the housing. In some embodiments, the system further comprises a housing, wherein the analytic device is within the housing, and wherein the one or more computer processors are external to the housing.

In another aspect, the present disclosure provides a method for programming an analytic device, comprising: (a) providing the analytic device comprising, wherein the analytic device is configured to perform a thermal cycling assay and a melting curve assay of a first biological sample, and wherein the analytic device is programmed to output data corresponding to the thermal cycling assay but not output data corresponding to the melting curve assay when assaying the first biological sample; (b) receiving, over a network, one or more instructions from a remote server, which one or more instructions are usable to configure the analytic device to output data corresponding to the melting curve assay; and (c) using the one or more instructions to configure the analytic device such that the analytic device outputs data corresponding to at least the thermal cycling assay and the melting curve assay when assaying a second biological sample. In some embodiments, the analytic device comprise a heating block comprising a recess configured to receive an assay tube comprising the first biological sample. In some embodiments, the analytic device comprises a heating unit in thermal communication with the heating block, which heating unit provides thermal energy to the heating block. In some embodiments, the analytic device comprises a cooling unit, which cooling unit reduces the thermal energy from the assay tube.

In another aspect, the present disclosure provides a method for unlocking features in an analytic device, comprising (a) providing the analytic device configured to perform a first assay and a second assay, wherein the first assay is unlocked such that the analytic device performs the first assay on a first biological sample and output data corresponding to the first assay, and wherein the second assay is locked such that the analytic device does not perform the second assay or output data corresponding to the second assay, (b) receiving over a network instructions to unlock the second assay, and (c) unlocking the second assay such that the analytic device performs the second assay on a second biological sample or outputs data corresponding to the second assay when the second assay is performed on the second biological sample. In some embodiments, the first assay is a thermal cycling assay. In some embodiments, the second assay is a melting curve assay.

In another aspect, the present disclosure provides a system for unlocking features in an analytic device, comprising: an analytic device configured to perform a first assay and a second assay, wherein the first assay is unlocked such that the analytic device performs the first assay on a first biological sample and output data corresponding to the first assay, and wherein the second assay is locked such that the analytic device does not perform the second assay or output data corresponding to the second assay, and one or more computer processors operatively coupled to the analytic device, wherein the one or more computer processors are individually or collectively programmed to (i) receive over a network instructions to unlock the second assay, and (ii) unlock the second assay such that the analytic device performs the second assay on a second biological sample or outputs data corresponding to the second assay when the second assay is performed on the second biological sample.

In another aspect, the present disclosure provides a method for programming an analytic device, comprising: (a) providing the analytic device having one or more features/operations that are operatively electronically activatable; (b) receiving one or more instructions usable to activate the one or more features/operations of the analytic device; and (c) using the one or more instructions to activate the one or more features/operations of the analytic device.

In another aspect, the present disclosure provides a method for programming an analytic device to activate one or more desired features/operations available to be performed by the example analytic device, the one or more features/operations comprising: 1) using one or more of a selected group of available optical frequencies when performing analysis on a biological sample input, 2) using a different one or more of a selected group of available optical frequencies when performing analysis on the biological sample input, 3) using yet another different one or more of a selected group of optical frequencies when performing analysis on a different biological sample input, the method comprising the steps of receiving electronically one or more programming instructions by the example analytic device that when executed by the analytic device illustratively activate one or more features/operations of the example analytic device, the activated one or more features/operations operative to perform desired analysis on one or more biological sample inputs. In an illustrative operation, the one or more programming instructions can operatively be electronically received by the example electronic device from one or more cooperating electronic devices local to the example electronic device and/or over an example communication module on the example analytic device operative to communicate and receive data over one or more example electronic communication protocols.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 23 shows a flow chart of an example method of programming an analytic device of the present disclosure.

FIG. 24 shows a flow chart of an example method of programming an analytic device of the present disclosure.

DETAILED DESCRIPTION

Figure 1A:
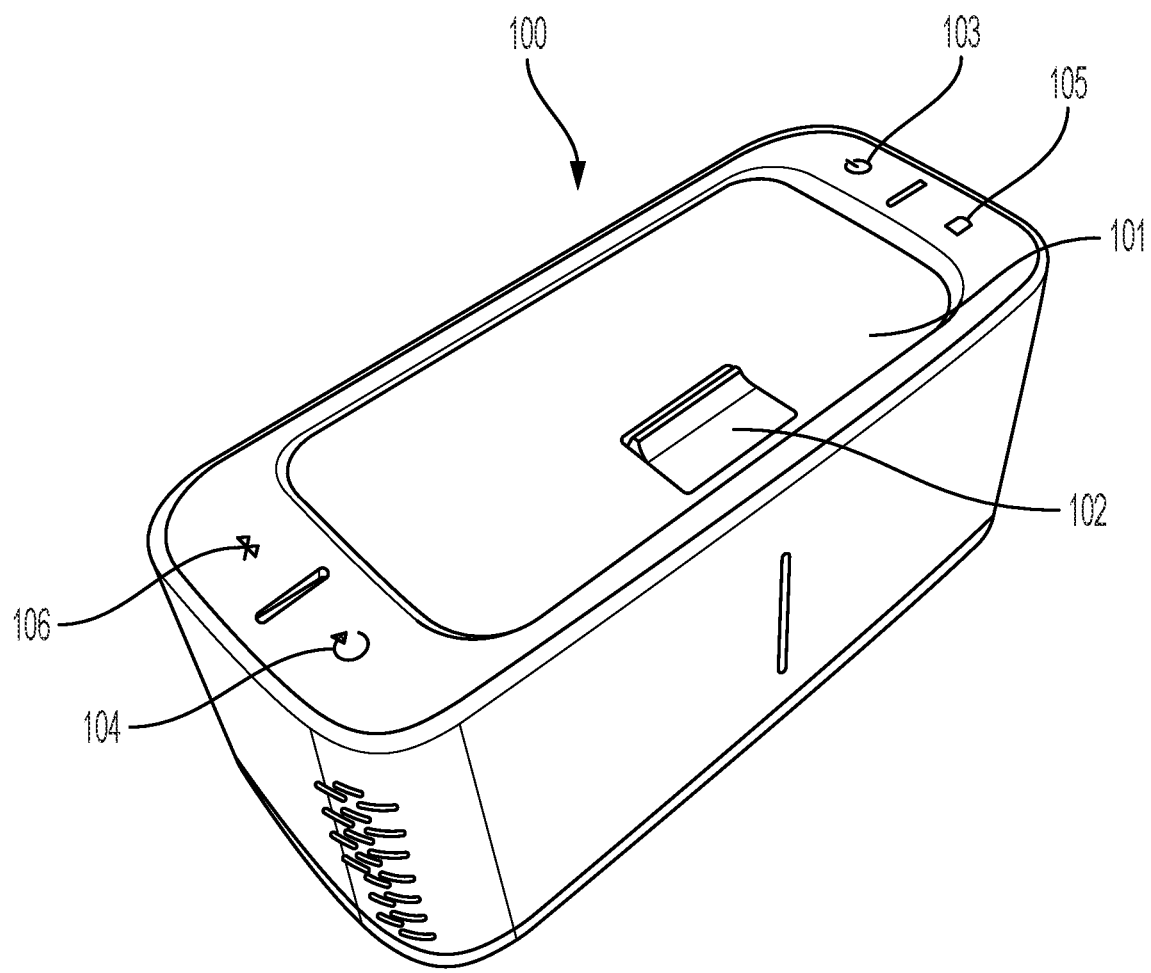
FIGS. 1A-1B show various views of a housing for a portable analytic device for analyzing a biological sample.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Overview

The present disclosure provides an analytic device that may be configured to perform multiple functions (e.g., multiple assays), but initially set to perform a limited number of functions but programed to unlock one or more additional functions upon request. A user of such analytic device may purchase the analytic device at a lower price for certain functions, and later upgrade the analytic device to perform additional functions. This may be performed upon performing a transaction between the user and an entity regulating access to such additional functions.

An analytic device may be configured to perform multiple functions, such as multiple assays. Examples of such assays include nucleic acid amplification, polymerase chain reaction (PCR), quantitative PCR (qPCR), isothermal amplification, melting curve analysis, and high resolution melting analysis. The additional functions may include additional color channels or additional assay programs. The user may not need to change the hardware and/or the software of the analytic device.

For example, at the time of purchase, the analytic device is unlocked to perform a qPCR assay by detecting two colors. The analytic device is equipped to detect more than two colors (e.g., the analytic device includes optics for detecting three colors), but an initial configuration of the analytic device is such that a user of the analytic device is permitted to perform the qPCR assay by detecting only two colors. Using the analytic device or an electronic device of the user (e.g., a smart phone), the user submits a request to unlock an additional color such that the user may perform a qPCR assay by detecting three colors. Such request may be directed to a server in remote (e.g., network) communication with the analytic device. Once the request has been granted, the server may send an unlock signal to the analytic device. The analytic device may be unlocked for the additional color, thus permitting the user to perform the qPCR assay by detecting three colors. The unlock signal may trigger the analytic device to permit the analytic device to use additional optics or process data corresponding to the additional color.

The analytic device provided herein (e.g., FIG. 14A) can enable multiplex real-time detection of multiple samples and/or multiple targets in a sample. Analytic devices of the disclosure may be configured to detect at least 1, 2, 3, 4, 5, 6, 7, 8, 9, 10, 20, or more targets in one sample or multiple samples (e.g., 2, 3, 4, 5, 6, 7, 8, 9, 10 or more samples). For example, an analytic device can detect up to twenty seven targets from one sample or three targets each from nine samples. In some examples, a user of the analytic device may have access to nine wells, three fluorophore (e.g., FAM/SYBR, TexasRedX, ATTO647N/CY5), and three color channels (e.g., Green, Amber, Red). In some cases, a user may not necessarily require all three color channels that the analytic device detects for the PCR testing. Instead, a user may prefer a device that consists of only one or two channels to detect one or two fluorophores at a cheaper price with the ability to add additional fluorophores/color channels as needed. The analytic device may be configured to detect one color and later unlocked for an additional one, two, three, four, five or more different color channels such that it can detect two, three, four, five, or six, or more different colors. The analytic device may be unlocked for additional color channels such that it can detect six, seven, eight, nine, or ten different colors. A user can upgrade or unlock the analytic device from a first given number of color channels to a second given number of color channels. There may be no limitation of the first given number or the second given number. For example, a user can upgrade or unlock the analytic device from one color channel to two color channels, from one color to three color channels, from one color channel to four color channels, from one color channel to five color channels, from two color channels to three color channels, from two color channels to four color channels, or from two color channels to five color channels.

The analytic device can be ungraded or unlocked by a mobile electronic device. An App on the mobile electronic device can be used to send instructions from the analytic device to a remote server. The mobile electronic device can be connected to the analytic device via BLE or serial to complete the upgrade.

In some cases, a user may scan a two or three-color multiplex test that is not compatible with the analytic device which is configured detect only one or two colors. The user may be prevented from running the test. If the device is connected, a warning may be shown to inform the user that the device can be upgraded before proceeding. If the device is not connected, a warning may be shown once the device is connected.

In some examples, if a user chooses to upgrade the analytic device, they may complete a form or request (e.g., Typeform), or the user may be redirected to a website (e.g., Shopify) to purchase additional channels, or the user can do an in-app purchase.

In some cases, a user may create a custom protocol that may or may not be compatible with the analytic device. The user may receive a warning after protocol creation and ask the user to confirm that he/she understand if the custom protocol is not compatible with the analytic device, he/she may not receive any results.

The present disclosure provides systems and methods for configuring, programming or unlocking features of an analytic device. The present disclosure also provides devices, systems, and methods for sample processing and/or analysis. An analytic device may be portable and may comprise a housing, a heating block heated by a heating unit that is configured to provide thermal energy to a sample container including a sample, and a light path to provide excitation energy from an excitation source to the sample. An analytic device may be configured to accept and/or communicate with a mobile electronic device. An analytic device may also comprise a movable carriage that comprises an optical filter and an excitation source and is configured to translate to bring the optical filter in alignment with the light path. The inclusion of a movable carriage may facilitate the production of a smaller and/or less expensive analytic device as one or more excitation sources, optical filters, and light paths of the movable carriage may be used to process and/or analyze multiple sample containers including multiple samples. An analytic device may be used to analyze a biological sample including, or suspected of including, one or more nucleic acid molecules to determine the presence or an amount of the one or more nucleic acid molecules.

FIG. 23 shows an example process flow for programming an analytic device. In the first operation 2301, an analytic device is provided to a user. The analytic device can comprise an optical detector configured to detect optical signals from a first biological sample over a plurality of optical frequencies comprising a first set of optical frequencies and a second set of optical frequencies different than the first set of optical frequencies. The analytic device can be programmed to output data corresponding to the first set of optical frequencies but not output data corresponding to the second set of optical frequencies when assaying the first biological sample. In the second operation 2302, the analytic device receives one or more instructions from a remote server over a network. The one or more instructions can be used to program the analytic device to output data corresponding to the second set of optical frequencies. In the third operation 2303, the user uses the one or more instructions to program the analytic device such that the analytic device can output data corresponding to at least the first set of optical frequencies and the second set of optical frequencies when assaying a second biological sample.

FIG. 24 shows another example process flow for programming an analytic device. In the first operation 2401, an analytic device is provided to a user. The analytic device can be configured to perform a first assay and a second assay on a first biological sample. The second assay may be different from the first assay. The analytic device can be programmed to output data corresponding to the first assay but not output data corresponding to the second assay. In the second operation 2402, the analytic device receives one or more instructions from a remote server over a network. The one or more instructions can be used to program the analytic device to output data corresponding to the second assay. In the third operation 2403, the user uses the one or more instructions to program the analytic device such that the analytic device can output data corresponding to at least the first assay and the second assay when assaying a second biological sample.

Figure 25:
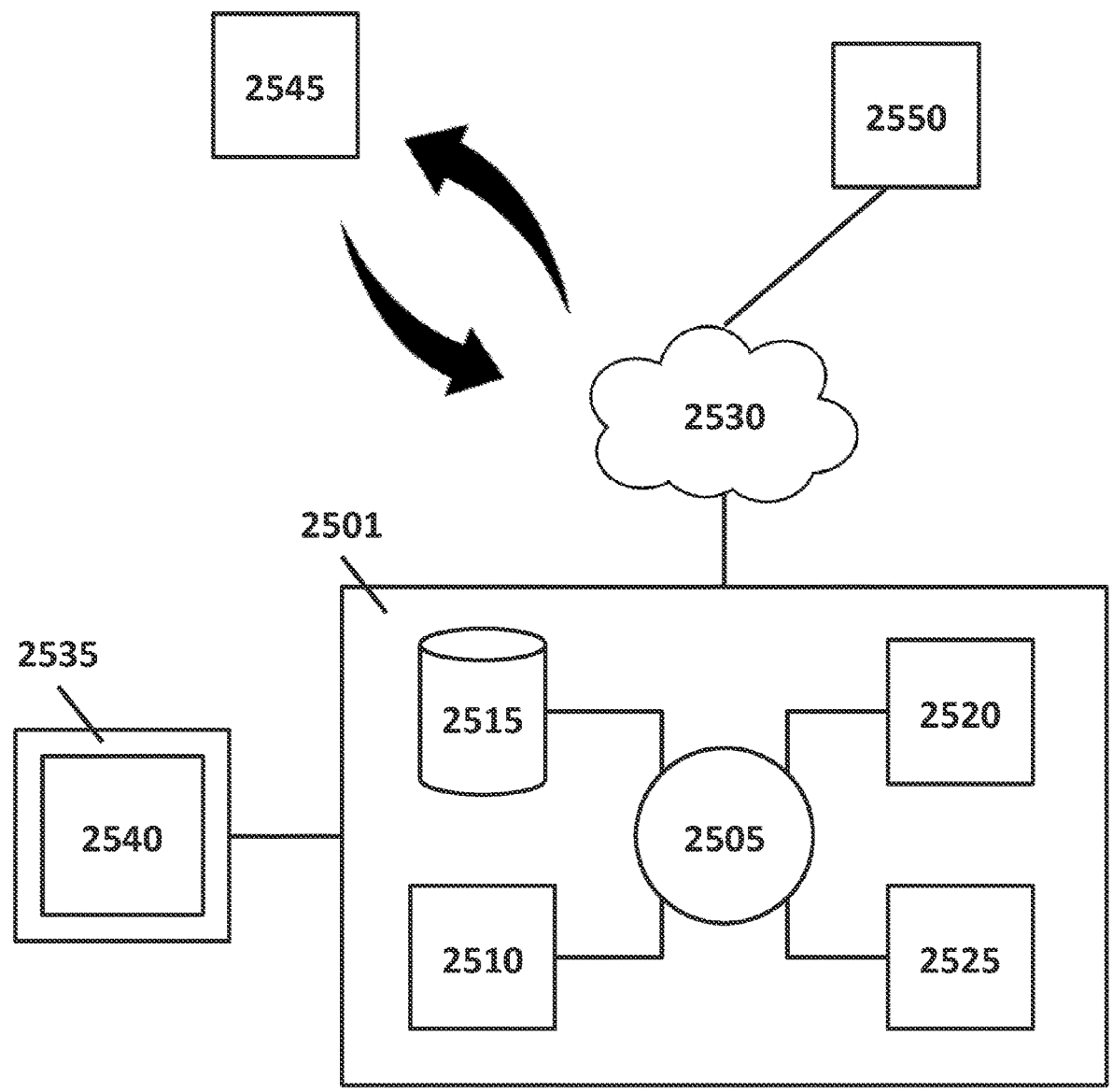
FIG. 25 shows an example system having an analytic device in communication with a remote server over a network.

FIG. 25 shows an example system having an analytic device in communication with a remote server for unlocking one or more features or functions. An analytic device 2545 can be connected to a network 2530, which may further comprise one or more remote servers 2550. The analytic device 2545 can be in communication with the one or more remote servers 2550 through the network 2530 for sending and receiving information (arrows). The analytic device can also be connected, through the network 2530, to a mobile electronic device 2501. For example, the analytic device 2545 can send a request to the mobile electronic device 2501 for unlocking one or more features or functions. The mobile electronic device 2501, upon receiving the request, can then send the request to the remote server 2550 through the network 2530. The remote server 2550 can send one or more instructions to the mobile electronic device 2501. A user of the mobile electronic device 2501 can use the one or more instructions to unlock the one or more features or functions of the analytic device 2545. The mobile electronic device can be a computer, a laptop, a phone (e.g., a smart phone), an iPad, or other devices that can communicate with the analytic device. The mobile electronic device 2501 can include memory or memory location 2510 (e.g., random-access memory, read-only memory, flash memory), electronic storage unit 2515 (e.g., hard disk), communication interface 2520 (e.g., network adapter) for communicating with one or more other systems, and peripheral devices 2525, such as cache, other memory, data storage and/or electronic display adapters. The memory 2510, storage unit 2515, interface 2520 and peripheral devices 2525 can be in communication with the CPU 2505 through a communication bus (solid lines), such as a motherboard. The mobile electronic device 2501 may include or be in communication with an electronic display 2535 that comprises a user interface (UI) 2540 for providing, for example, messages (e.g., a request for unlocking a function) received from the analytic device, warnings, current status of a sample, or experimental data.

Analytic Device

Figure 1B:
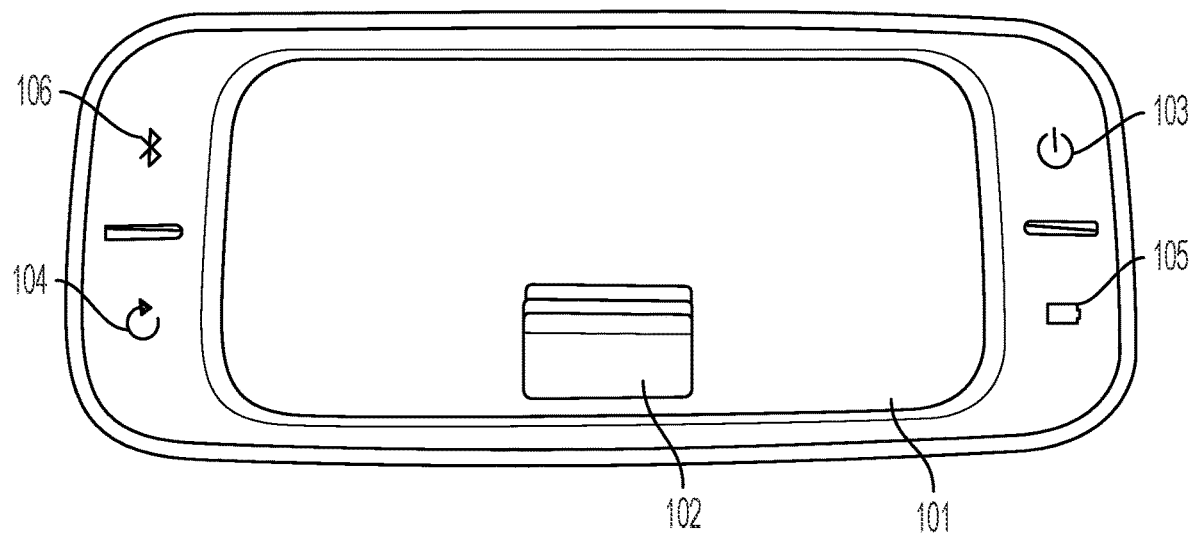

An analytic device of the present disclosure may be used for processing and/or analyzing a sample, such as a biological sample. An analytic device of the present disclosure may be portable. For example, an analytic device may be hand-held. FIGS. 1A-1B show (A) perspective and (B) side views of a housing 100 for a portable analytic device for analyzing a biological sample. A housing may have a lid 101, a securing unit 102 for securing the lid in an open or closed position, and/or buttons or indicators 103-106. Housing 100 may comprise a button 103 for powering on/off the device. Housing 100 may comprise a button 104 for restarting the device. Housing 100 may comprise an indicator 105 for notifying a user that the battery is low and/or an indicator 106 that a wireless connection (e.g., a Bluetooth or Near Field Communication connection) has been established between the analytic device and a mobile electronic device. In some cases, the analytic device is an assaying device. The mobile electronic device can be a phone, a laptop, a computer, or an iPad. The phone may be a smart phone. The mobile electronic device can be a device that can communicate with the analytic device. The mobile electronic device can be wirelessly connected to the analytic device.

An analytic device may comprise at least one button capable of, upon actuation, affecting the operability of the analytic device (e.g., powering on/off the device or connecting the analytic device to other devices). An analytic device may comprise 1, 2, 3, 4, 5, or more buttons. For example, an analytic device may comprise 4 buttons. Each button may correspond to a different function or feature of the analytic device. In some cases, pairs of buttons may correspond to the same function or feature of the analytic device. For example, an analytic device may include a button to increase a value, zoom level, volume, or other characteristic as well as a button to decrease the same value, zoom level, volume, or other characteristic.

A button mechanism may be a physical mechanism. For example, a button may comprise a depressible mechanism, such as button or micro-switch. Alternatively, a button may comprise a slidable or rotatable mechanism. For analytic devices including two or more buttons, each button may be separately selected from the group consisting of depressible mechanisms, slidable mechanisms, and rotatable mechanisms.

A button may comprise a touch-sensitive feature or mechanism. For example, buttons 103 and 104 of FIGS. 1A and 1B may comprise a touch-sensitive feature or mechanism. A touch-sensitive mechanism may be a touch-sensitive virtual mechanism (e.g., a virtual button). Such a virtual mechanism may be virtually depressible, virtually slidable, or virtually rotatable, thereby giving the illusion of a physical button. For example, the analytic device may comprise or be configured to accept a mobile electronic device communicatively coupled with a wireless connection to the analytic device, and the mobile electronic device may comprise one or more virtual buttons. Depression of a virtual button of the mobile electronic device may transmit a signal from the mobile electronic device to the analytic device, thereby affecting, e.g., a thermocycling program or other process, as described herein. A connection between an analytic device and a mobile electronic device may comprise a one-way or two-way wired or wireless connection, such as a WiFi connection, a Bluetooth connection, a Bluetooth LE connection, an ANT+ connection, a Gazell connection, or any other wireless data communication protocol.

An analytic device may comprise one or more buttons disposed anywhere on the external surface of a housing of the analytic device. For example, a button may be located on a front face, a back face, a right side, a left side, a top side, or a bottom side of a housing of an analytic device. A button may be disposed in a location that is unavailable or hidden during operation of an analytic device (e.g., on the bottom side of a housing of the analytic device). In some cases, a panel may be used to cover or hide one or more buttons (e.g., when the analytic device is not in use and/or to prevent accidental actuation of a button).

Actuation or activation of one or more buttons may permit the user to cycle between a plurality of different thermocycling programs. For example, actuation of a button may cause an analytic device to switch from executing a first thermocycling program to a second thermocycling program. In another example, actuation of a button may cause an analytic device to switch from an "off" state to executing a first thermocycling program. Actuation of the button a second time may cause the analytic device to switch from executing a first thermocycling program to an "off" state. It should appreciated that an "off" state may refer to an idle state (e.g., wherein an analytic device may be on but a thermocycling program is paused, or wherein the analytic device is in a minimal power state) or a powered-down state (e.g., wherein the analytic device is powered off). Actuation of a button may affect a parameter of a thermocycling program. For example, an analytic device may comprise a depressible mechanism, and actuation of the depressible mechanism may cause a thermocycling program to switch from a denaturation step to an annealing step. In another example, an analytic device may comprise a rotatable mechanism, and rotation of the rotatable mechanism may cause a thermocycling temperature to increase. In some cases, actuation of two or more buttons may be used to affect a thermocycling program.

The degree of an input may affect the state of a thermocycling program. Non-limiting examples of a degree of an input that may be varied include a number of inputs (e.g., a number of times a button is actuated and released in succession), a speed of an input (e.g., a speed at which a button is actuated and/or released), a duration of an input (e.g., an amount of time that a button is actuated), a force exerted for the input (e.g., a force with which a button is actuated), and a direction of an input. An input may comprise actuation of a button. In one example, an analytic device may comprise a depressible mechanism, and brief (e.g., less than half of one second) depression and subsequent release of the depressible mechanism may pause a thermocycling program. In another example, a paused thermocycling program may be resumed by depressing a depressible mechanism for, e.g., 1-2 seconds.

An analytic device may be configured to accept one or more containers including a sample. For example, an analytic device may be configured to accept one or more assay tubes. An assay tube for use with an analytic device of the present disclosure may have any useful size and shape and comprise any useful material. For example, an assay tube may comprise a plastic, a polymer, or glass. An analytic device may be configured to accept an assay tube having a cross section that is substantially cylindrical, substantially rectangular, or has any other shape (e.g., a star shape). An analytic device may be configured to accept an assay tube having a mechanical key element such as a groove or protrusion disposed at one end of the assay tube or along a dimension of the assay tube to facilitate placement of the assay tube in the analytic device. For example, an assay tube may comprise a substantially rectangular protrusion along its length and the analytic device may comprise a corresponding indentation configured to accept the assay tube in a particular orientation. An analytic device may be configured to accept an assay tube having a cap or lid. Alternatively, an analytic device may comprise a component configured to cover an opening of an assay tube when the assay tube is placed in the analytic device. An analytic device may be configured to accept one or more assay tubes. For example, an analytic device may be configured to accept 1, 2, 3, 4, 5, 6, 7, 8, 9, or more assay tubes.

A device described herein can have a surface or support to receive a reagent tube or a cartridge. The cartridge can be a reagent cartridge. The surface or support can be a recessed surface or support. The surface can be a protruded surface or support. The surface can be a chamber. The cartridge can be loaded onto the surface or support. Upon loading the cartridge onto the surface or support, a lid can be closed to click the cartridge in place.

Figure 1C:
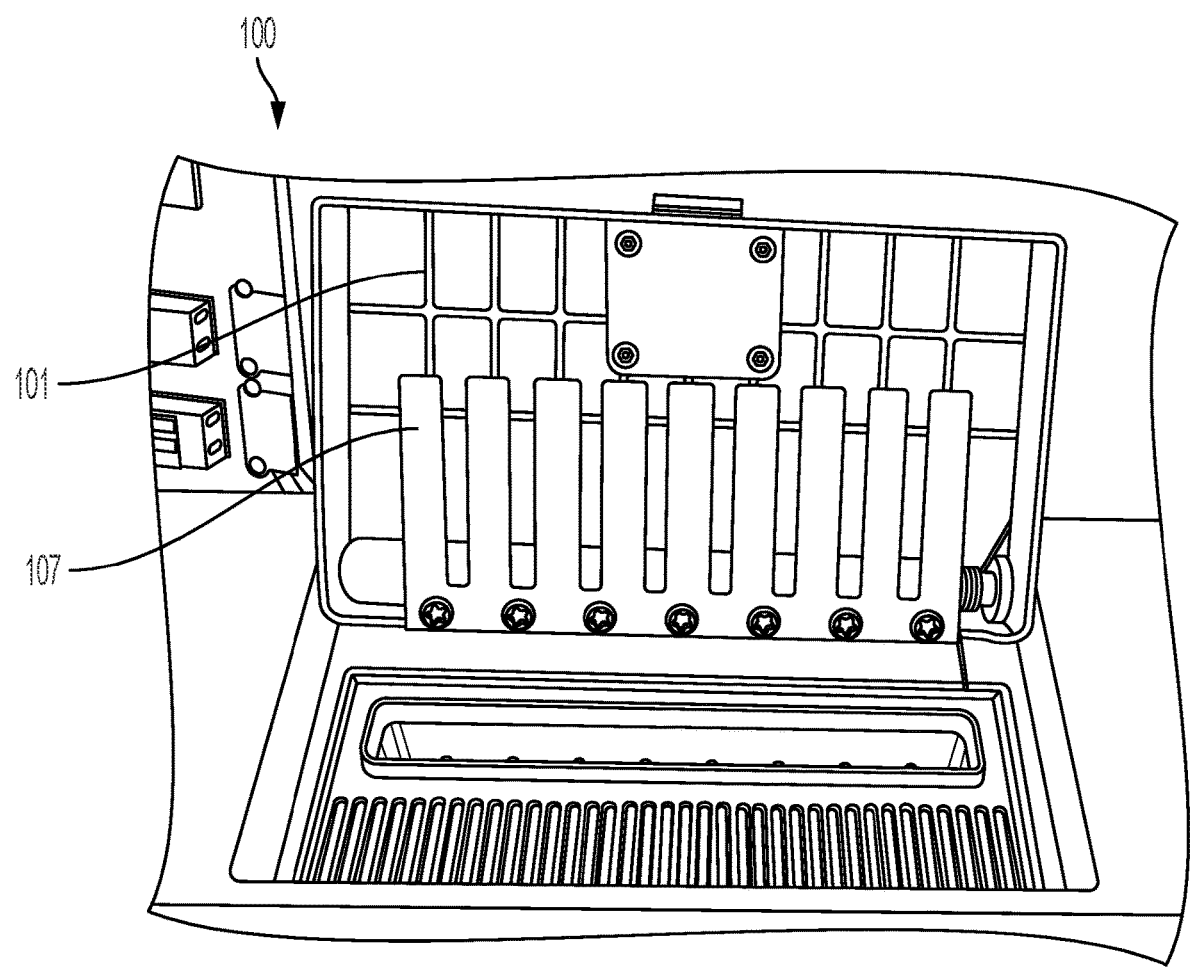
FIG. 1C shows a lid of a housing for a portable analytic device, the lid having a bendable comb capable of applying pressure and/or heat to an assay tube inserted into the analytic device.
Figure 1D:
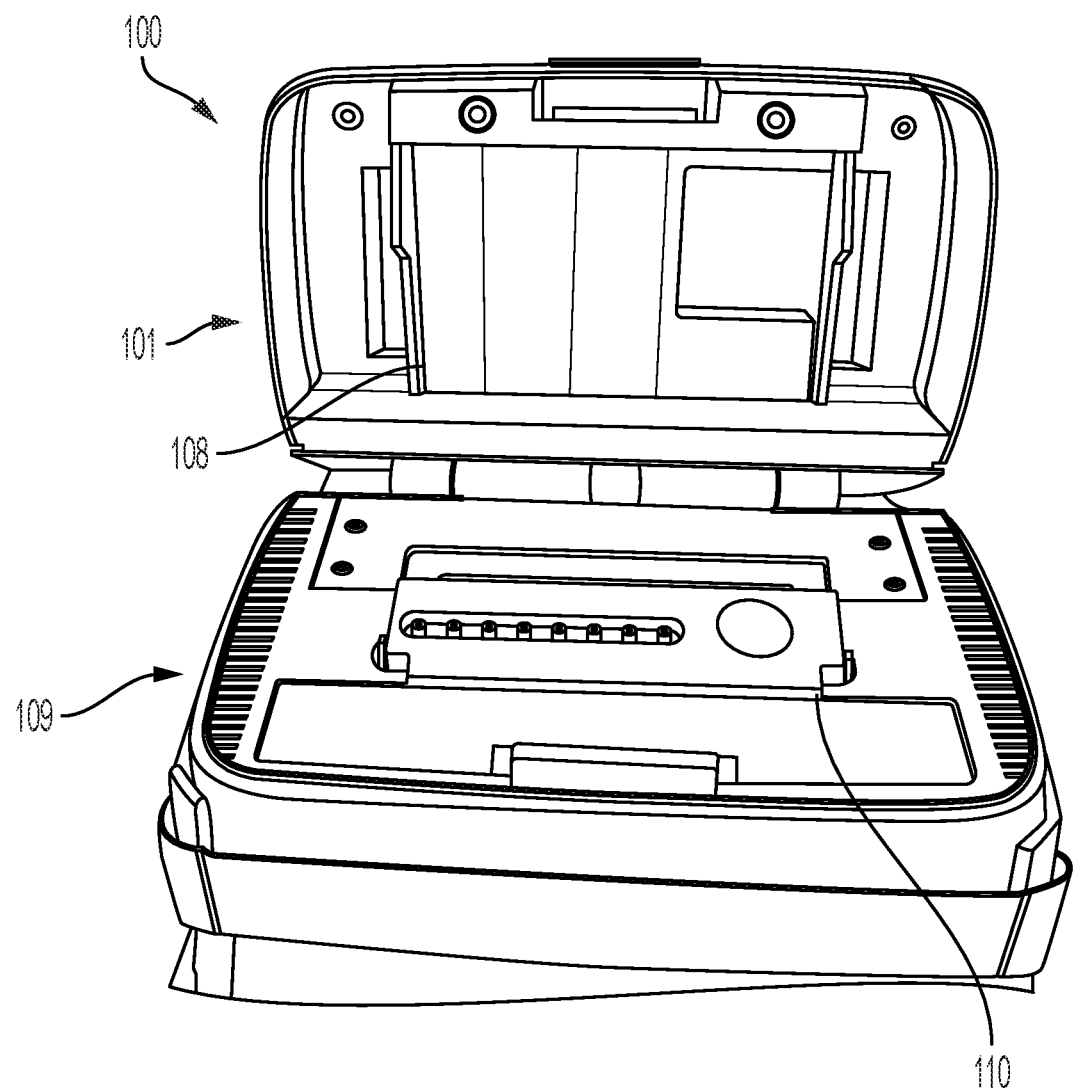
FIG. 1D shows an example of a housing for a portable analytic device with the lid open.

As shown in FIG. 1C, an inner surface of a lid 101 of housing 100 of the analytic device may comprise one or more cantilevers 107 capable of applying pressure to one or more assay tubes seated in a heating block of the analytic device. A cantilever may be useful for securing an assay tube containing a sample against the heating block, thereby increasing the efficiency of energy transfer between the heating block and the assay tube. A cantilever may be heated (e.g., at a temperature equal to the temperature of the heating block) to effect heating of a portion of the assay tube not in contact with the heating block. A cantilever may be heated to any temperature, and the temperature of the cantilever may change throughout a thermal cycle. For example, the temperature of a cantilever may be coordinated (e.g., to be the same as) the temperature of the heating block throughout a thermal cycle. As shown in FIG. 1D, an inner surface of a lid 101 of housing 100 of the analytic device may comprise a recessed surface 108 to receive or accommodate a cartridge inserted into the device. An inner surface of the body 109 of housing 100 of the analytic device may comprise a protruded surface 110 to receive a cartridge inserted into the device.

An analytic device may be portable. For example, an analytic device including a housing may be able to be easily carried or moved. A size, weight and/or shape of the housing and/or other components may affect the portability of the analytic device. A volume of a housing of an analytic device may be less than about 100,000 cubic centimeters, less than about 50,000 cubic centimeters, less than about 10,000 cubic centimeters, less than about 9,000 cubic centimeters, less than about 8,000 cubic centimeters, less than about 7,000 cubic centimeters, less than about 6,000 cubic centimeters, less than about 5,000 cubic centimeters, less than about 4,500 cubic centimeters, less than about 4,000 cubic centimeters, less than about 3,500 cubic centimeters, less than about 3,000 cubic centimeters, less than about 2,500 cubic centimeters, less than about 2,000 cubic centimeters, less than about 1,500 cubic centimeters, less than about 1,400 cubic centimeters, less than about 1,300 cubic centimeters, less than about 1,200 cubic centimeters, less than about 1,100 cubic centimeters, less than about 1,000 cubic centimeters, less than about 900 cubic centimeters, less than about 800 cubic centimeters, less than about 700 cubic centimeters, less than about 600 cubic centimeters, or less than about 500 cubic centimeters. For example, a volume of a housing of an analytic device may be less than about 1,500 cubic centimeters. A volume of a housing of an analytic device may fall within a range. For example, a volume of a housing of an analytic device may be between about 500 cubic centimeters and about 1,500 cubic centimeters. A dimension of the housing (e.g., length, width or height) may be at most about 50 centimeters, at most about 40 centimeters, at most about 30 centimeters, at most about 25 centimeters, at most about 24 centimeters, at most about 23 centimeters, at most about 22 centimeters, at most about 21 centimeters, at most about 20 centimeters, at most about 19 centimeters, at most about 18 centimeters, at most about 17 centimeters, at most about 16 centimeters, at most about 15 centimeters, at most about 14 centimeters, at most about 13 centimeters, at most about 12 centimeters, at most about 11 centimeters, at most about 10 centimeters, at most about 9 centimeters, at most about 8 centimeters, at most about 7 centimeters, at most about 6 centimeters, or at most about 5 centimeters.

A weight of an analytic device including the housing may be less than about 25 kilograms, less than about 20 kilograms, less than about 15 kilograms, less than about 10 kilograms, less than about 5 kilograms, less than about 4.5 kilograms, less than about 4 kilograms, less than about 3.5 kilograms, less than about 3 kilograms, less than about 2.5 kilograms, less than about 2.4 kilograms, less than about 2.3 kilograms, less than about 2.2 kilograms, less than about 2.1 kilograms, less than about 2 kilograms, less than about 1.9 kilograms, less than about 1.8 kilograms, less than about 1.7 kilograms, less than about 1.6 kilograms, less than about 1.5 kilograms, less than about 1.4 kilograms, less than about 1.3 kilograms, less than about 1.2 kilograms, less than about 1.1 kilograms, less than about 1 kilogram, less than about 0.9 kilograms, less than about 0.8 kilograms, less than about 0.7 kilograms, less than about 0.6 kilograms, less than about 0.5 kilograms, less than about 0.4 kilograms, less than about 0.3 kilograms, less than about 0.2 kilograms, or less than about 0.1 kilograms. For example, a volume of a housing of an analytic device may be less than about 1.5 kilograms. A weight of an analytic device including a housing may fall within a range of weights. For example, a weight of an analytic device including a housing may be between about 0.5 kilograms and about 1.5 kilograms.

A shape of a housing of an analytic device may also contribute to the portability of the analytic device. At least one dimension of a housing (e.g., length, width or height), may be sufficiently small such that the housing may be easily grasped by the human hand. An analytic device may have an ergonomically shaped housing of a size that enables a user to hold the analytic device with one or two hands. The housing may comprise a gripping region, e.g., a portion of the housing that is gripped by the user when the user holds the analytic device. A gripping region of a housing may be shaped to conform to the fingers of the user, thereby allowing the user to maintain a secure grip on the housing. A front surface of a housing of an analytic device may be narrower in a middle section associated with a gripping region than at a top or bottom section of the front surface. The narrower section may be conveniently and securely gripped by the user, while the relatively wider top section may include a display device or a component thereof, such as a screen. A housing may comprise a retractable handle that may be ergonomically shaped. A housing of an analytic device may feature rounded corners and/or edges (e.g., where perpendicular surfaces meet) such that when a user holds the analytic device, the user's hand may be in contact with rounded corners rather than sharp corners.

Figure 9:
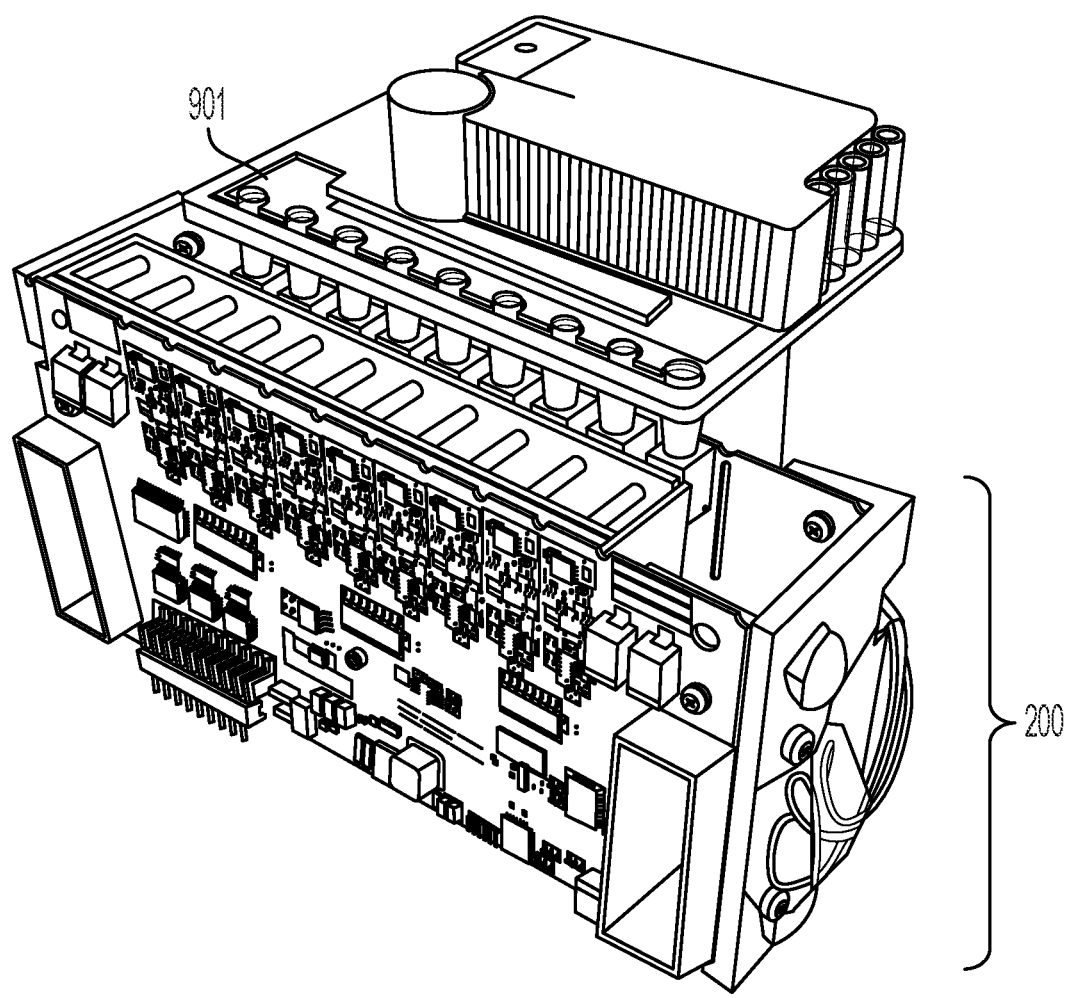
FIG. 9 shows an example portable analytic device having multiple heating blocks, and assay tubes inserted into the heating blocks.
Figure 13:
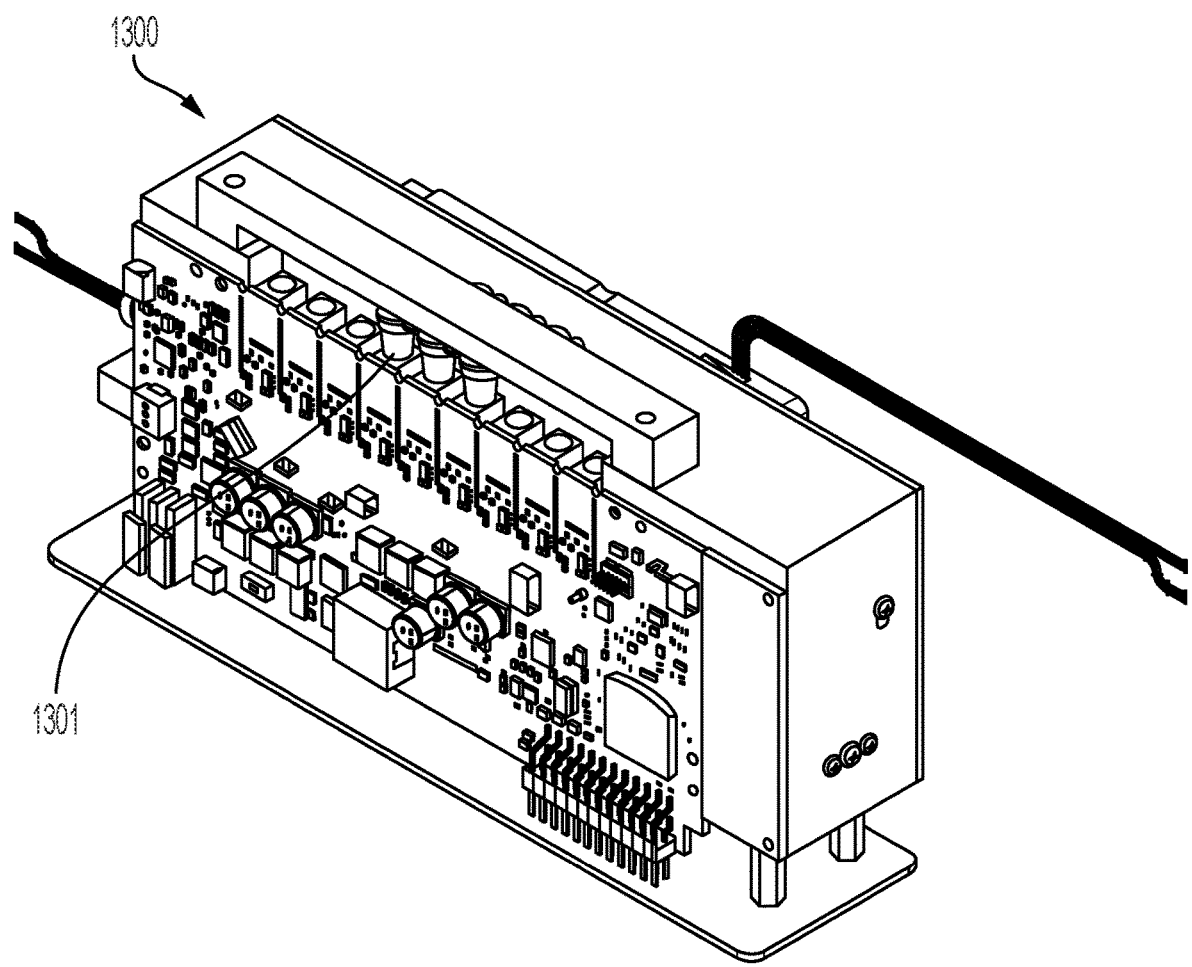
FIG. 13 shows an example portable analytic device having multiple heating blocks, and assay tubes inserted into the heating blocks.

FIG. 9 shows an example portable device having a sample cartridge 901 inserted into the device for sample analysis. A perspective view of an internal mechanism 200 is shown. FIG. 13 shows another example of the portable device 1300 having sample tubes 1301 inserted into the device for sample analysis.

Thermocycling

Figure 2:
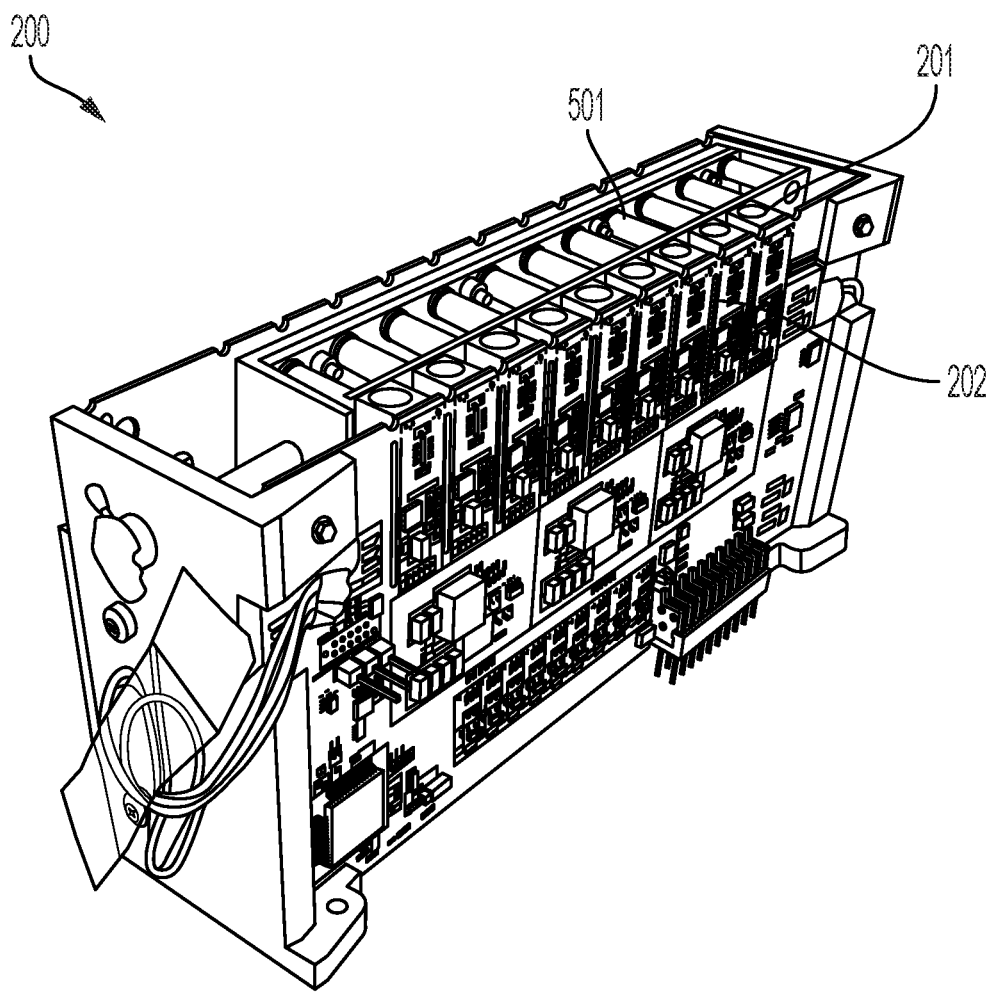
FIG. 2 shows a perspective view of an internal mechanism for a portable analytic device for analyzing a biological sample.

An analytic device may be configured to heat or cool a sample within an assay tube. As shown in FIG. 2, an analytic device 200 may comprise one or more heating blocks 201 within which an assay tube containing a sample is placed. The analytic device may be configured to raise or lower the temperature of the heating block using a heater 202 (e.g., a resistive heater) in discrete steps.

In some cases, the heating block can convert electrical energy into heat through the process of resistive or Joule heating. The heating block can be a resistive heater. Heated blocks can have power resister (e.g., thermister), thermal epoxy to bring in thermal communication with sample chambers. The heating blocks may be level and uniform. Cooling of the heating block can be achieved or controlled through a fan.

In some cases, the heating block can be a Peltier heater. Heating and cooling can be achieved or controlled through a Peltier controller. In some other cases, the heating block may not be a Peltier heater or the heating block may not be controlled by a Peltier controller.

The device described herein may or may not comprise a heated lid.

Figure 3A:
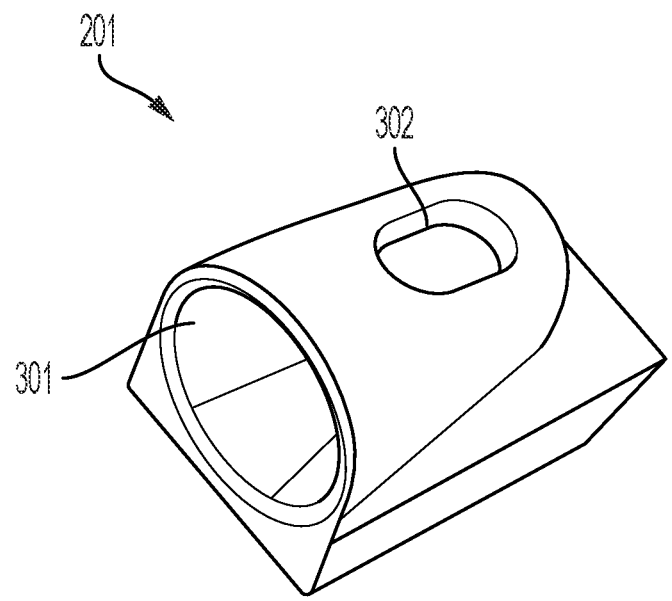
FIGS. 3A-3B show various heating blocks for use in a portable analytic device.
Figure 3B:
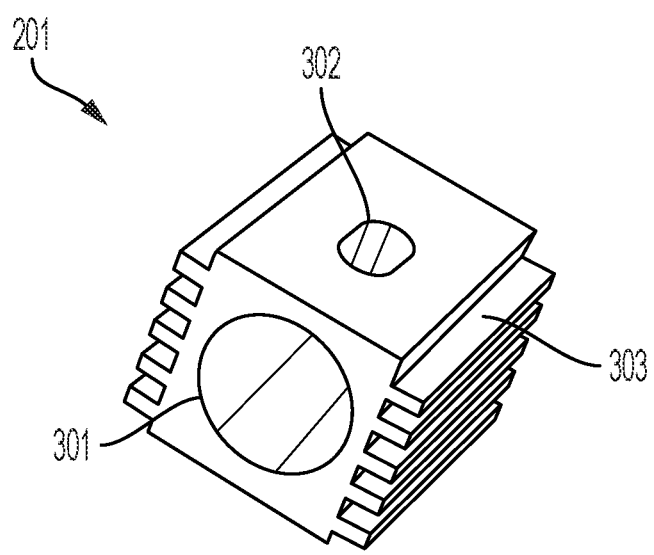

A heating block 201 may comprise any useful material. Non-limiting examples of materials that may be used to construct a heating block include aluminum, concrete, glass, quartz, steel, iron, nickel, zinc, copper, brass, silver, tin, gold, carbon, and any combination thereof (e.g., a zinc alloy such as Zamak). For example, a heating block may be constructed using silver, as shown in FIG. 3A. In another example, a heating block may be constructed using aluminum, as shown in FIG. 3B. The heating block may include a first opening 301 for accepting a vial containing or configured to contain a sample (e.g., biological sample), and a second opening 302 configured to be in optical communication with a detector or an optical source (e.g., for excitation). The heating block may include a third opening (not shown) configured to be in optical communication with a detector or an optical source. For example, the second opening 302 may be in optical communication with a detector and the third opening (not shown) may be in optical communication with an optical source for excitation. The heating block may comprise one or more fins 303.

A heating block may be formed of an alloy. For example, a heating block may be constructed using steel. It is contemplated that constructing the heating block using a material compatible with the process of die casting, (e.g., a material that that may be used in the die cast construction of a heating block) can allow for the heating blocks to be manufactured at a larger scale (e.g., at a higher volume in a shorter period of time, and/or at a reduced cost per unit). In some embodiments, a heating block can be constructed using a combination of materials. For example, a heating block can be constructed using aluminum and subsequently coated with nickel. In another example, a heating block can be constructed using zinc, and coated with silver. Coating the heating block can be advantageous for several reasons. For example, coating a heating block (e.g., with nickel) can allow the heating block to be soldered to a printed circuit board (PCB), as opposed to using thermal epoxy. Soldering the heating block to the PCB can allow an analytic device to be manufactured with a removable heating block (e.g., in the case of damage), whereas the use of a thermal epoxy can permanently affix the heating block to the PCB. It is contemplated that the choice of the material used to produce the heating block may affect the number of thermal cycles that the analytic device is capable of undergoing using a power supply (e.g., a self-contained power supply, such as a battery). In particular, the higher the specific heat capacity of the material, the more energy may be used to raise the temperature of the material. Accordingly, a heating block can be constructed using a material with a specific heat capacity (e.g., at 25° C., as measured in Joules per gram per ° C.; J/g° C.) of less than about 2 J/g° C., less than about 1.5 J/g° C., less than about 1 J/g° C., less than about 0.9 J/g° C., less than about 0.8 J/g° C., less than about 0.7 J/g° C., less than about 0.6 J/g° C., less than about 0.5 J/g° C., less than about 0.45 J/g° C., less than about 0.4 J/g° C., less than about 0.35 J/g° C., less than about 0.3 J/g° C., less than about 0.25 J/g° C., less than about 0.2 J/g° C., less than about 0.15 J/g° C., less than about 0.1 J/g° C., less than about 0.05 J/g° C., or less than about 0.01 J/g° C. For example, a heating block can be constructed using a material having a specific heat capacity of less than about 1 J/g° C. at 25° C.

Additionally, the lower the thermal conductivity of a material, the more energy may be required to raise the temperature of the material. Accordingly, a heating block can be constructed using a material with a thermal conductivity (e.g., as measured in Watt per meter per Kelvin; W/mK) of at least about 500 W/mK, at least about 400 W/mK, at least about 300 W/mK, at least about 200 W/mK, at least about 175 W/mK, at least about 150 W/mK, at least about 125 W/mK, at least about 100 W/mK, at least about 75 W/mK, at least about 50 W/mK, at least about 25 W/mK, or at least about 10 W/mK. For example, a heating block can be constructed using a material having a thermal conductivity of at least about 75 W/mK. In another example, a heating block can be constructed using a material having a thermal conductivity of at least about 400 W/mK.

A heating block may also comprise one or more fins 303 to increase a surface area of the heating block and provide better heat dissipation from the heating block. It is also contemplated that the volume of the material used to form a heating block may affect the number of thermal cycles that the analytic device is capable of undergoing using a power supply (e.g., a self-contained power supply, such as a battery). In particular, the greater the volume of the material used to construct the heating block, the more energy may be used to raise the temperature of the heating block. Accordingly, a volume of a material used to construct a heating block may be less than about 20 cubic centimeters, less than about 15 cubic centimeters, less than about 10 cubic centimeters, less than about 9 cubic centimeters, less than about 8 cubic centimeters, less than about 7 cubic centimeters, less than about 6 cubic centimeters, less than about 5 cubic centimeters, less than about 4 cubic centimeters, less than about 3 cubic centimeters, less than about 2 cubic centimeters, less than about 1 cubic centimeters, less than about 0.9 cubic centimeters, less than about 0.8 cubic centimeters, less than about 0.7 cubic centimeters, less than about 0.6 cubic centimeters, less than about 0.5 cubic centimeters, less than about 0.4 cubic centimeters, less than about 0.3 cubic centimeters, less than about 0.2 cubic centimeters, or less than about 0.1 cubic centimeters. For example, a volume of a material used to construct a heating block may be less than about 0.5 cubic centimeters.

As described above, the material and/or volume of material used to construct the heating block may be selected based on minimizing the energy used to heat or cool the block. Accordingly, an analytic device of the present disclosure may provide more energy to perform a greater number of thermal cycles, as compared to a device that uses a larger heating block, or a heating block constructed using a material with a higher specific heat capacity. An analytic device of the present disclosure may perform any number of thermal cycles. An analytic device may perform a given number of thermal cycles on a single charge of a power supply (e.g., a self-contained power supply, such as a battery). An analytic device of the present disclosure may perform at least about 1 thermal cycle, at least about 2 thermal cycles, at least about 3 thermal cycles, at least about 4 thermal cycles, at least about 5 thermal cycles, at least about 6 thermal cycles, at least about 7 thermal cycles at least about 8 thermal cycles, at least about 9 thermal cycles, at least about 10 thermal cycles, at least about 11 thermal cycles, at least about 12 thermal cycle, at least about 13 thermal cycles, at least about 14 thermal cycles, at least about 15 thermal cycles, at least about 16 thermal cycles, at least about 17 thermal cycles, at least about 18 thermal cycles at least about 19 thermal cycles, at least about 20 thermal cycles, at least about 25 thermal cycles, at least about 30 thermal cycles, at least about 35 thermal cycle, at least about 40 thermal cycles, at least about 45 thermal cycles, at least about 50 thermal cycles, or at least about 100 thermal cycles. An analytic device of the present disclosure may perform about 1 to about 10 thermal cycles, about 5 to about 15 thermal cycles, about 10 to about 20 thermal cycles, or about 15 to about 25 thermal cycles.

An analytic device of the present disclosure may be configured to perform an amplification reaction such as polymerase chain reaction (PCR) (e.g., by cycling the temperature of a sample in an assay tube). Performing PCR may involve making a series of repeated temperature changes (e.g., thermal cycles) with each series (e.g., cycle) including two or three discrete temperature steps. Thermal cycling may be preceded by a single temperature step at a higher temperature (e.g., >90° C.). Temperatures used and the length of time they are applied in each cycle may vary based on, for example, the enzyme used for deoxyribonucleic acid (DNA) synthesis, the concentration of bivalent ions and nucleotides (dNTPs) in the reaction, and the melting temperature (Tm) of one or more primers. The individual steps of an amplification reaction such as PCR may comprise initialization, denaturation, annealing, and/or extension/elongation. Initialization may be used for DNA polymerases that require heat activation (e.g., "hot start" PCR). Initialization may comprise heating a sample (e.g., a sample in an assay tube) to a high temperature (e.g., 94-96° C. [201-205° F.) or 98° C. [208° F.], if thermostable polymerases are used), which may be maintained for about 1-10 minutes. Denaturation may comprise heating (e.g., to 94-98° C. [201-208° F.]) a sample (e.g., a sample in an assay tube) for a given time such as between about 5 seconds and 5 minutes. This may result in DNA melting, or denaturation, of a double-stranded DNA template by breaking hydrogen bonds between complementary bases, yielding two single-stranded nucleic acid molecules (e.g., templates). Annealing may comprise lowering the temperature of a sample (e.g., a sample in an assay tube) to, e.g., 50-65° C. (122-149° F.) for a given time, such as between about 5 seconds and 5 minutes, thereby allowing annealing of one or more primers to each of the single-stranded nucleic acid templates. At least two different primers may be included in the reaction mixture, including one for each of the two single-stranded nucleic acid templates containing a target region. The primers may be single-stranded nucleic acid molecules themselves. Conditions suitable for effective extension/elongation may depend on the DNA polymerase used. Extension/elongation comprises synthesizing a new DNA strand complementary to a single-stranded nucleic acid template by adding, in the presence of a DNA polymerase, free dNTPs from a reaction mixture that are complementary to the template in the 5'-to-3' direction and condensing the 5'-phosphate group of the dNTPs with the 3'-hydroxy group at the end of the nascent (elongating) DNA strand. The time used for extension/elongation may depend on the DNA polymerase used and/or on the length of the DNA target region to amplify.

Denaturation, annealing, and extension/elongation may constitute a single thermal cycle. Multiple cycles may be used to amplify a DNA target to a detectable level.

Figure 4:
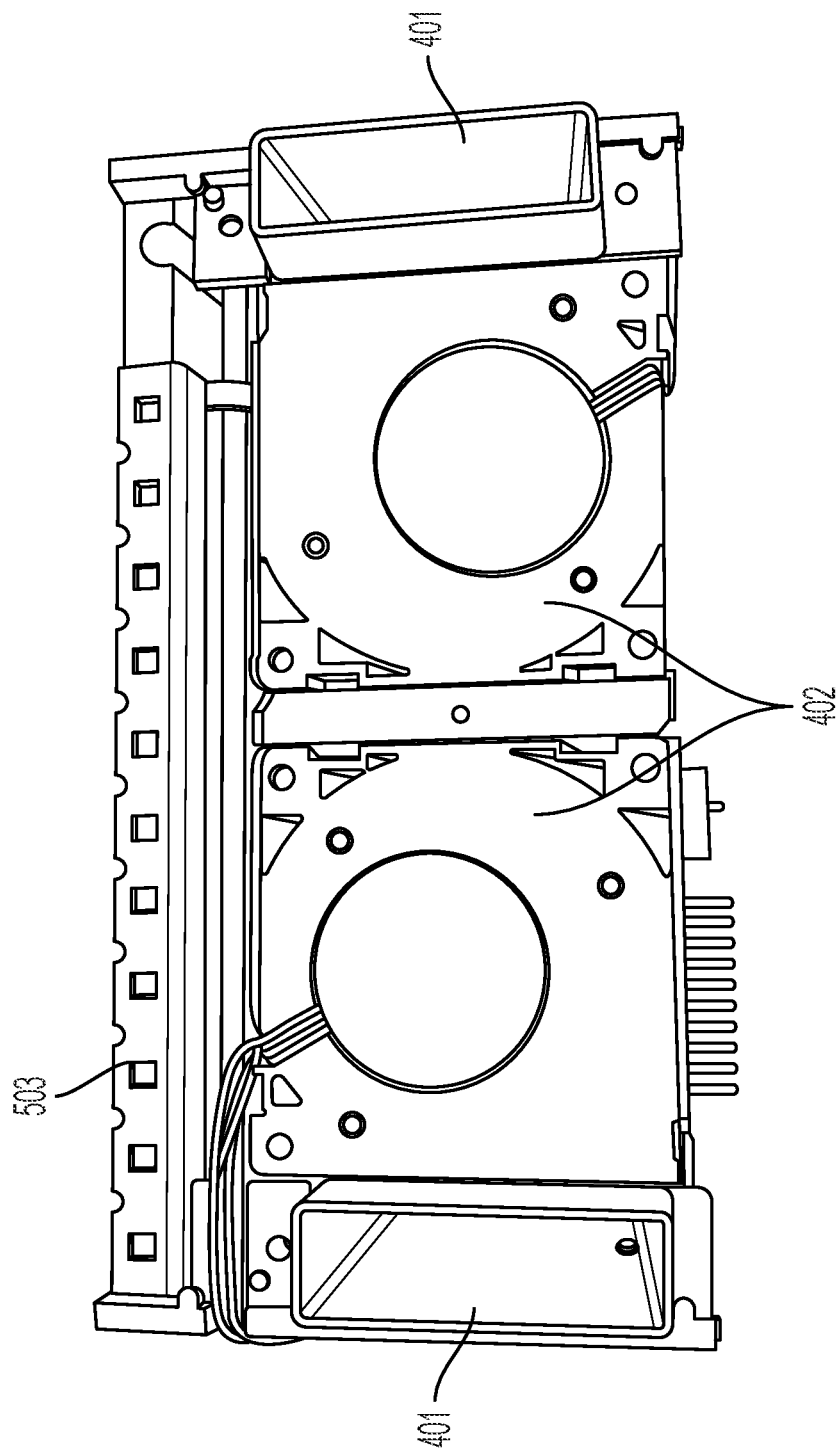
FIG. 4 shows a rear view of an internal mechanism for a portable analytic device with a circuit board removed, thereby exposing fans of the internal mechanism.

The temperature of a heating block may be regulated in any useful way. Thermal energy may be provided to or removed from a sample (e.g., a sample in an assay tube) by heating or cooling, respectively, the heating block. A temperature of a heating block may be controlled (e.g., increased or decreased) using a heating unit (e.g., comprising a resistive, ohmic heater, or flexible heater) and/or a cooling unit (e.g., comprising a thermoelectric cooler or a fan). Temperature monitoring may be necessary for thermocycling applications. Accordingly, a heating or cooling unit may also comprise one or more thermistors and/or temperature transducers to monitor and/or provide feedback to a heating or cooling unit to regulate the temperature of a heating block. A heating or cooling unit may be disposed adjacent to a heating block (e.g., on a surface of a heating block). Alternatively, a heating or cooling unit may be disposed within a recess along a surface of a heating block. A cooling unit may comprise a fan disposed away (e.g., not in direct contact with) a heating block. A fan may be used to apply a positive or negative pressure to a volume adjacent to a heating block, thereby evacuating the area surrounding the heating block. By evacuating the area surrounding the heating block, which may comprise air having radiant heat energy from the heating block, the temperature of the heating block may be reduced. A fan may be used to generate a vacuum to evacuate radiant heat surrounding the heating block. Alternatively, a fan may be used to generate positive pressure to exhaust or force radiant heat surrounding the heating block (e.g., a fluid comprising heat from the heating block) out of the analytic device. As shown in FIGS. 4A-4B, radiant heat surrounding the heating block may be removed from the analytic device through one or more vents 401 disposed on the analytic device. One or more fans 402 may be fluidly connected to the space surrounding the heating block and one or more vents. An analytic device may comprise any number of fans. For example, an analytic device may comprise 1, 2, 3, 4, 5, or more fans. An analytic device may comprise one fan for each heating block.

Carriage

Figure 5A:
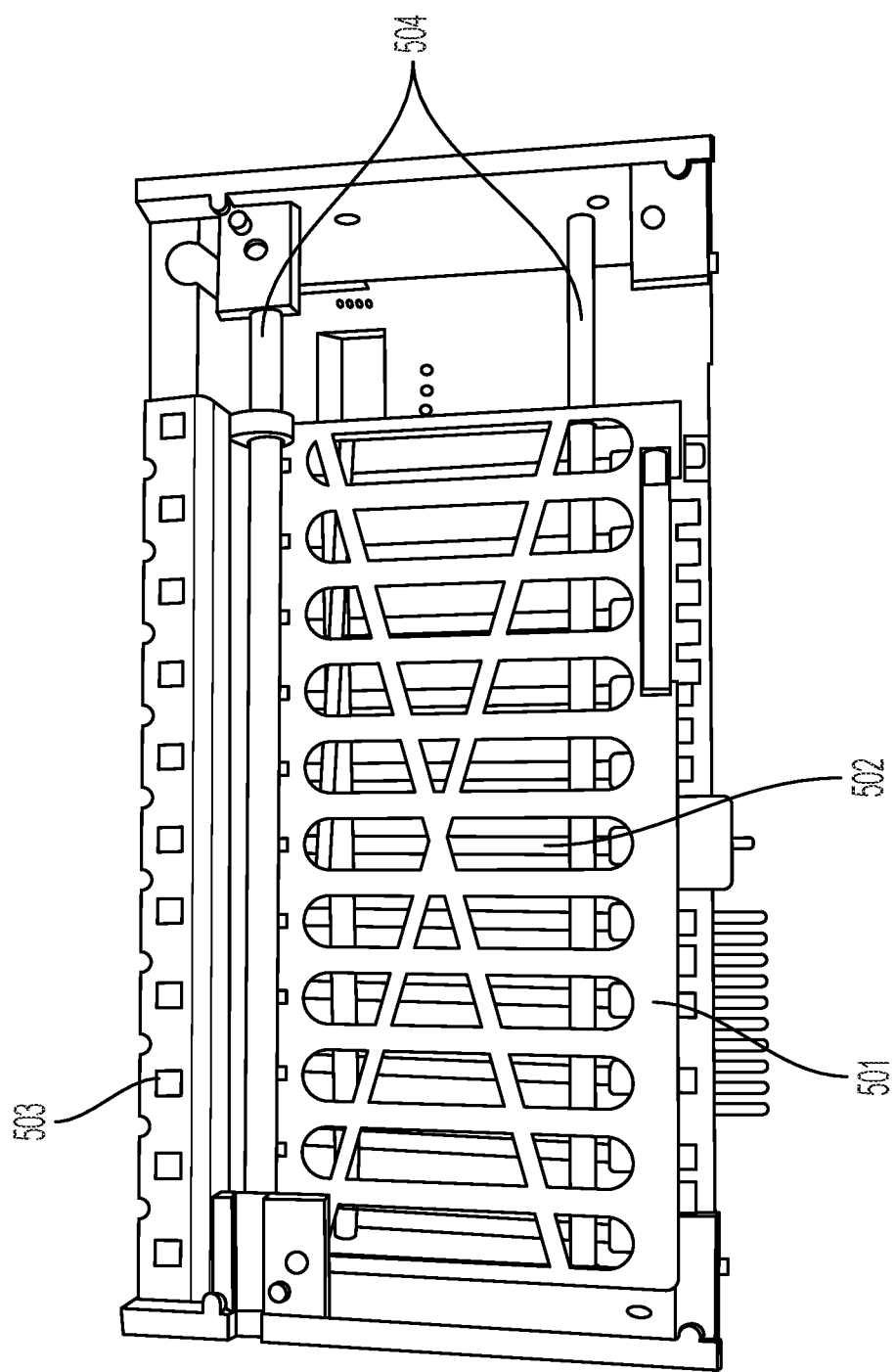
FIG. 5A shows a rear view of an internal mechanism for a portable analytic device with a circuit board and fans removed, thereby exposing a moving carriage of the internal mechanism.
Figure 5B:
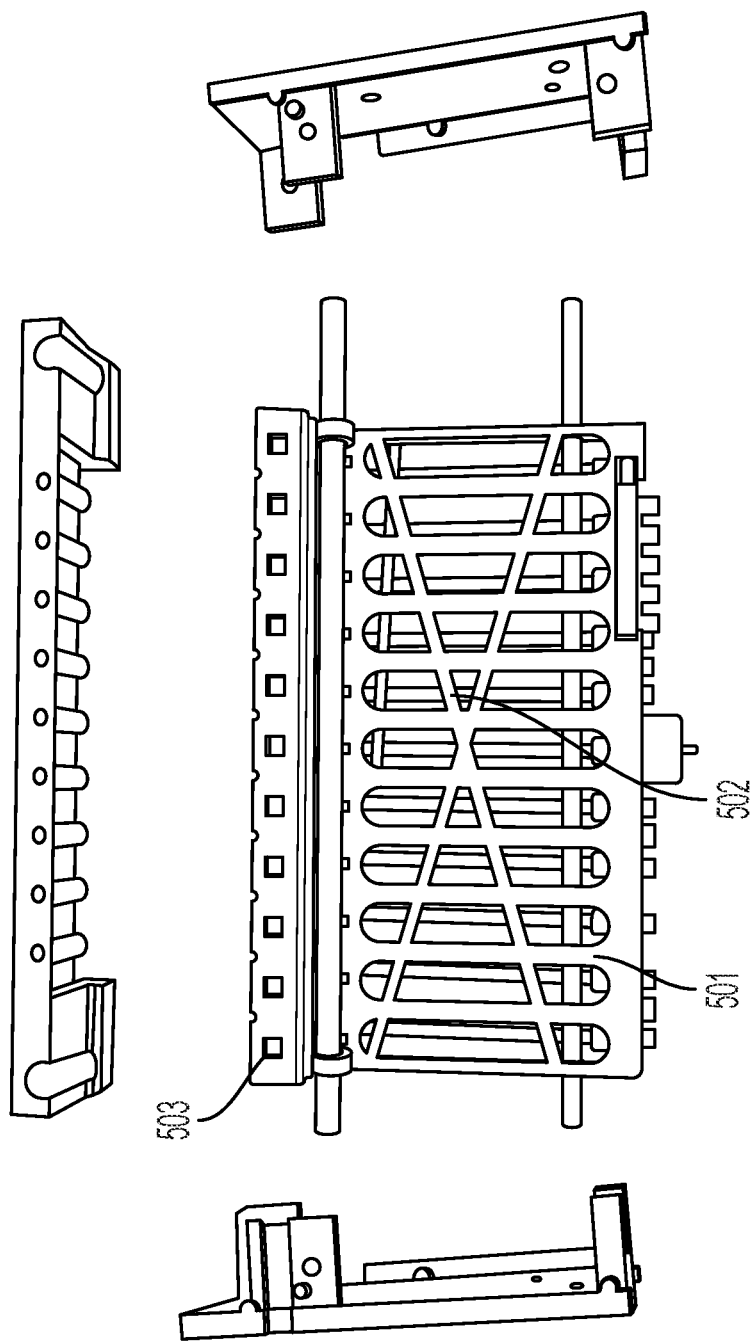
FIG. 5B shows a deconstructed view of a moving carriage of the internal mechanism.
Figure 5C:
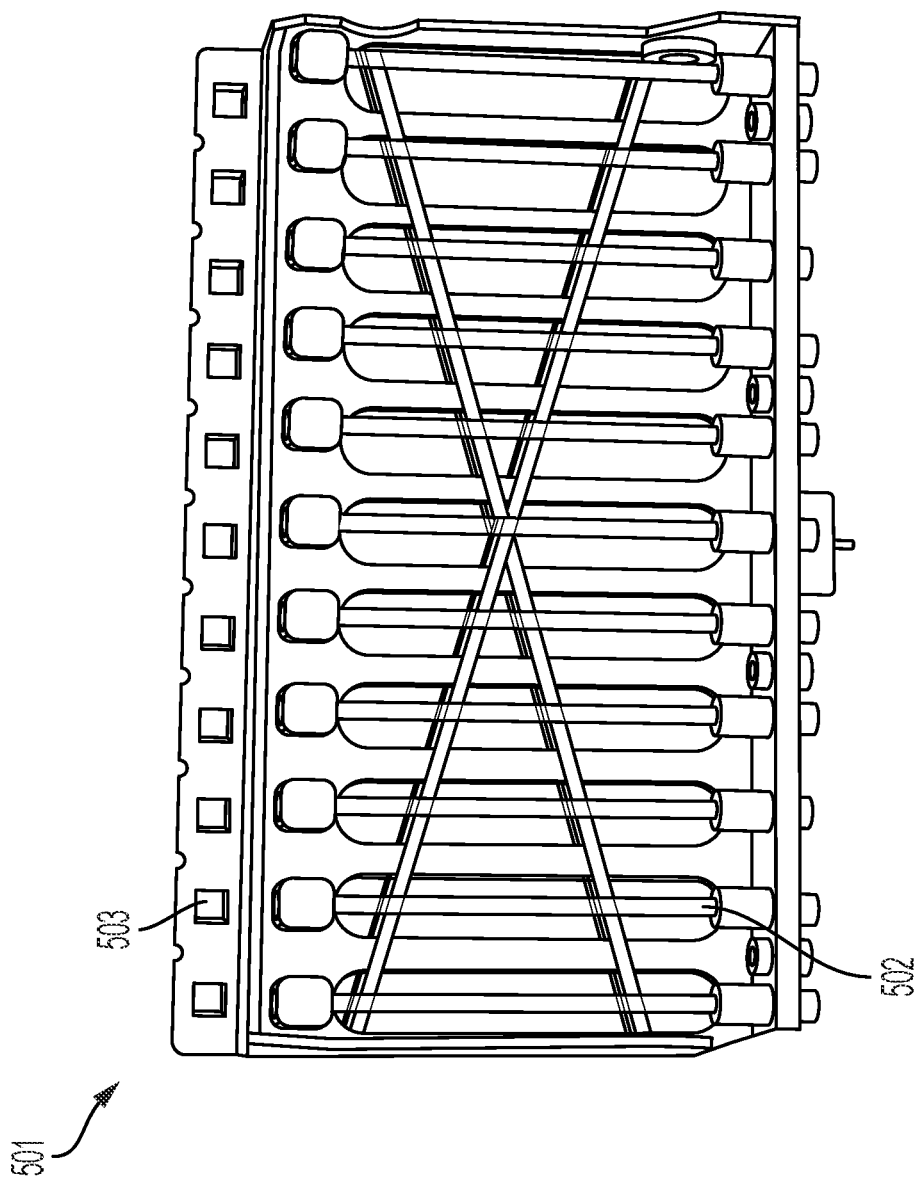
FIG. 5C shows a front view of a moving carriage of the internal mechanism, the moving carriage having multiple light paths.

An analytic device may comprise a carriage. A carriage may be used to hold in place or shift one or more optical components (e.g., an optical filter such as an emission filter or an excitation filter, a light path, and/or a light source) to align with a specified assay tube. As shown in FIG. 5A, a carriage 501 may comprise various optical components, such as an excitation filter (not shown), a light path 502 (e.g., a light pipe) to communicate filtered excitation energy to a sample (e.g., a sample in an assay tube), and an emission filter 503 to filter emission energy prior to detection by a detector. FIG. 5B shows a deconstructed view of the carriage mechanism shown in FIG. 5A. The carriage may be configured to move along one or more paths, grooves, or rails 504. The carriage may be constructed using any useful material. Non-limiting examples of materials that may be used to construct the carriage include polysiloxane, polyphosphazene, low-density polyethylene (ldpe), high-density polyethylene (hdpe), polypropylene (pp), polyvinyl chloride (pvc), polystyrene (ps), nylon, nylon 6, nylon 6,6, teflon (polytetrafluoroethylene), thermoplastic polyurethanes (tpu), polychlorotrifluoroethylene (pctfe), bakelite, kevlar, twaron, mylar, neoprene, nylon, nomex, orlon, rilsan, technora, teflon, ultem, vectran, viton, zylon, polyamides, polycarbonate, polyester, polyethylene, polyvinylidene chloride (pvdc), acrylonitrile butadiene styrene (abs), polyepoxide, polymethyl methacrylate, maleimide, polyetherimide, polylactic acid, furan, silicone, polysulfone, or a metal or metal alloy (e.g., aluminum, brass, copper, iron, and silver). A light path may comprise an open space of a particular geometry and volume. The space may be defined by a container or guide such as a pipe. A light path (e.g., a light pipe) may be constructed using any useful material. Non-limiting examples of materials that may be used to construct a light path (e.g., a light pipe) include glass, silica, fluorozirconate, fluoroaluminate, chalcogenide, plastic, PMMA, polystyrene, silicone resin, and any combination thereof.

A carriage may be a moving carriage. A moving carriage may be used to shift a light path aligning with a first light source and a first assay tube to a second light source and a second assay tube. Similarly, a moving carriage may be used to shift a sample from aligning with a first light path to align with a second light path. An analytic device comprising a moving carriage may provide certain advantages compared to an analytic device comprising, in lieu of a moving carriage, a stationary component. For example, the inclusion of a moving carriage may allow multiple assay tubes to share light paths and associated components such as optical filters (e.g., excitation and emission filters). This may reduce the cost of producing the analytic device (e.g., by requiring fewer optical filters, e.g., excitation and emission filters, which may be costly). The sharing of light paths may also reduce the overall size of the analytic device (e.g., by reducing the number of optical components necessary for analyzing the sample in each assay tube), thereby making the analytic device more portable. A moving carriage may be configured to move from a first or original position to a final position, making one or more stops at specified positions between the original and final positions. The path between the original and final positions may be a linear path and may comprise one or more grooves, tracks, or rails along which a moving carriage may travel. The path between the original and final positions may comprise one or more specified positions at which the moving carriage may stop (e.g., via a manual or automated control, as described herein). The one or more specified positions may correspond to the positions of one or more assay tubes or seats or housings therefor in an analytic device. A specified position may comprise a mechanical component such as a key to facilitate positioning of the moving carriage in the specified position (e.g., beneath an assay tube). Movement of a moving carriage may be achieved using a variety of methods. For example, an electric motor may be used to move the carriage from a first position to a second position. A motor having a cam may be used to move the carriage via a belt coupled to the carriage and the cam. Movement of a moving carriage may be achieved using a magnetic levitation system. For example, a carriage may be slidably disposed on or in one or more electrified rails or grooves, and a magnetic force generated within a rail or groove may be used to move the carriage. A spring may be used to return a moving carriage to its original position, e.g., after it has moved from its original position to a final position, such as the end of a rail, track, or groove. It is contemplated that constructing the moving carriage using lighter weight materials may reduce the energy used to move the carriage, thereby increasing the amount of energy available for heating and/or cooling the sample and/or other processes.

Figure 6A:
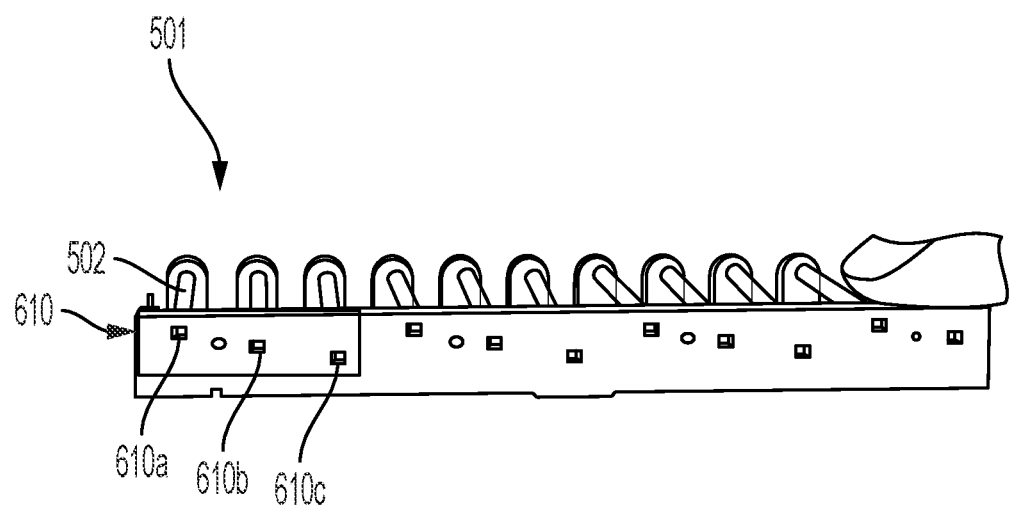
FIG. 6A shows a bottom view of a moving carriage of the internal mechanism, the bottom of the moving carriage having multiple optical filters, which may be offset from one another.

A carriage may comprise one or more optical filters (e.g., excitation or emission filters) and one or more light pipes. FIG. 6A shows a carriage comprising one or more excitation filters 610*a* (red), 610*b* (yellow), and 610*c* (blue). A carriage may also comprise one or more emission filters. A light pipe may extend from an optical filter (e.g., an excitation filter) to an assay tube containing a sample.

An analytic device may comprise any useful optical filters (e.g., excitation and/or emission filters). Filters may be optical bandpass filters (e.g., optical interference films) having a bandpass at a frequency that may be optimal for one or more of (i) the excitation wavelength of a fluorophore or dye, and (ii) the emission wavelength of a fluorophore or dye. A filter may substantially attenuate non-bandpass frequencies to prevent transmission of undesirable light. For example, when using SYBR Green dye, an excitation filter bandpass may center around a wavelength of 485 nm, and an emission filter bandpass may center around a wavelength of 555 nm. An optical filter (e.g., an excitation filter and/or an emission filter) may be tilted (e.g., a plane containing the filter may be disposed at an angle) relative to a light path.

Excitation Source

Figure 6B:
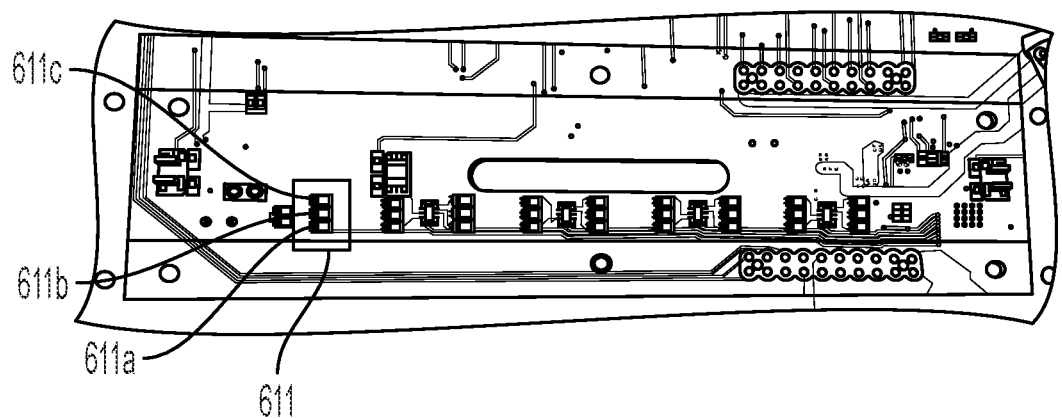
FIG. 6B shows a circuit board having multiple excitation sources (e.g., LEDs), which are spaced to correspond to the offset of the optical filters shown in FIG. 6A.

An analytic device may comprise one or more excitation sources. An excitation source may be disposed on a carriage (e.g., a moving carriage, as described herein) and may be configured to deliver excitation energy to a sample (e.g., a sample in an assay tube) through an excitation filter and a light path. For an analytic device comprising a moving carriage, a single excitation source disposed on the carriage may be configured to deliver excitation energy to two or more samples (e.g., two or more samples in two or more assay tubes) through the same excitation filter and light path (e.g., as the moving carriage aligns the excitation source and light path with different assay tubes containing different samples). As shown in FIG. 6B, an analytic device may have a dedicated set 611 of excitation sources 611*a* (blue), 611*b* (yellow), and 611*c* (red) for each assay tube.

An excitation source may comprise a Light Emitting Diode (LED) or an array of LEDs (e.g., a set of single-color LEDs). An LED may have any useful size, shape, wavelength, or other characteristic. An LED may be a high power LED that may emit greater than or equal to about 1 mW of excitation energy. A high power LED may emit at least about 5 mW of excitation energy. An LED or an array of LEDs may emit, for example, about 50 mW of excitation energy. An array of high-powered LEDs may be used that draws, for example, about 10 watts of energy or less, or about 10 watts of energy or more. The total power draw may depend on the power of each LED and the number of LEDs in the array. The use of LEDs in an analytic device as an excitation source may be beneficial, for example, because an LED array may result in a significant reduction in power usage over other light sources such as halogen light sources. An excitation source may use a power of about 1 microwatt (µW) or less. Alternatively, an excitation source may use a power of about 1 microwatt (µW), about 5 µW, about 25 µW, about 50 µW, about 100 µW, about 1 milliwatt (mW), about 5 mW, about 25 mW, about 50 mW, about 100 mW, about 1 W, about 5 W, about 50 W, or about 100 W or more, individually or when in used in an array. In some cases, a cooling device such as, but not limited to, a heat sink or fan may be used to cool the excitation source or a component thereof.

An excitation source may comprise an organic LED (OLED) or an array of OLEDs. An OLED may have any useful size, shape, wavelength, or other characteristic. An OLED may provide luminescence over a large area, for example, to provide excitation energy to multiple assay tubes simultaneously. Scatter or cross-talk light between multiple sample wells (e.g., seats or housings for assay tubes) for such an OLED may be reduced by overlaying a mask on the OLED or by patterning the luminescence of the OLED to operatively align with the multiple sample wells. An OLED may be a low power consumption device. An OLED may include a small-molecule OLED and/or a polymer-based OLED also known as a Light-Emitting Polymer (LEP). A small-molecule OLED that is deposited on a substrate may be used. An OLED that is deposited on a surface by vapor-deposition technique may be used. An OLED may also be deposited on a surface by, for example, silk-screening. An LEP may be used that is deposited by, for example, via solvent coating.

An excitation source may comprise an array of LEDs or OLEDs 611a-611c (e.g., multiple single-color LEDs). The array may be constructed and arranged in any configuration. For example, the excitation sources in an array may be arranged linearly along the axis of movement of a moving carriage. Alternatively, as shown in FIG. 6B, the excitation sources in an array may be arranged linearly perpendicular to the axis of movement of a moving carriage. In such a configuration, the light paths 502 may be disposed at an angle relative to the base of the moving carriage. A light path extending from the base of the moving carriage (e.g., from an excitation filter disposed in the base of the moving carriage) may be perpendicular to the base of the carriage, or not perpendicular to the base of the carriage (e.g., at an angle other than 90 degrees to the base of the carriage).

One or more lenses may be used to direct, re-direct, focus, disperse, or collimate excitation or emission energy. For example, a lens may be used to focus excitation energy onto a sample (e.g., a sample in an assay tube). In another example, a lens may be used to collimate excitation energy from an excitation source. Non-limiting examples of lenses that may be used include a biconvex lens, a plano-convex lens, a positive meniscus lens, a negative meniscus lens, a plano-concave lens, a biconcave lens, a Fresnel lens, a cylindrical lens, a lenticular lens, and a gradient index lens. For example, a Fresnel lens may be used to collimate excitation energy from an excitation source and direct the excitation energy into a light path. A Fresnel lens may be made much thinner than a comparable plano-convex lens, in some cases taking the form of a flat sheet, which may be advantageous for producing a portable analytic device.

Figure 7:
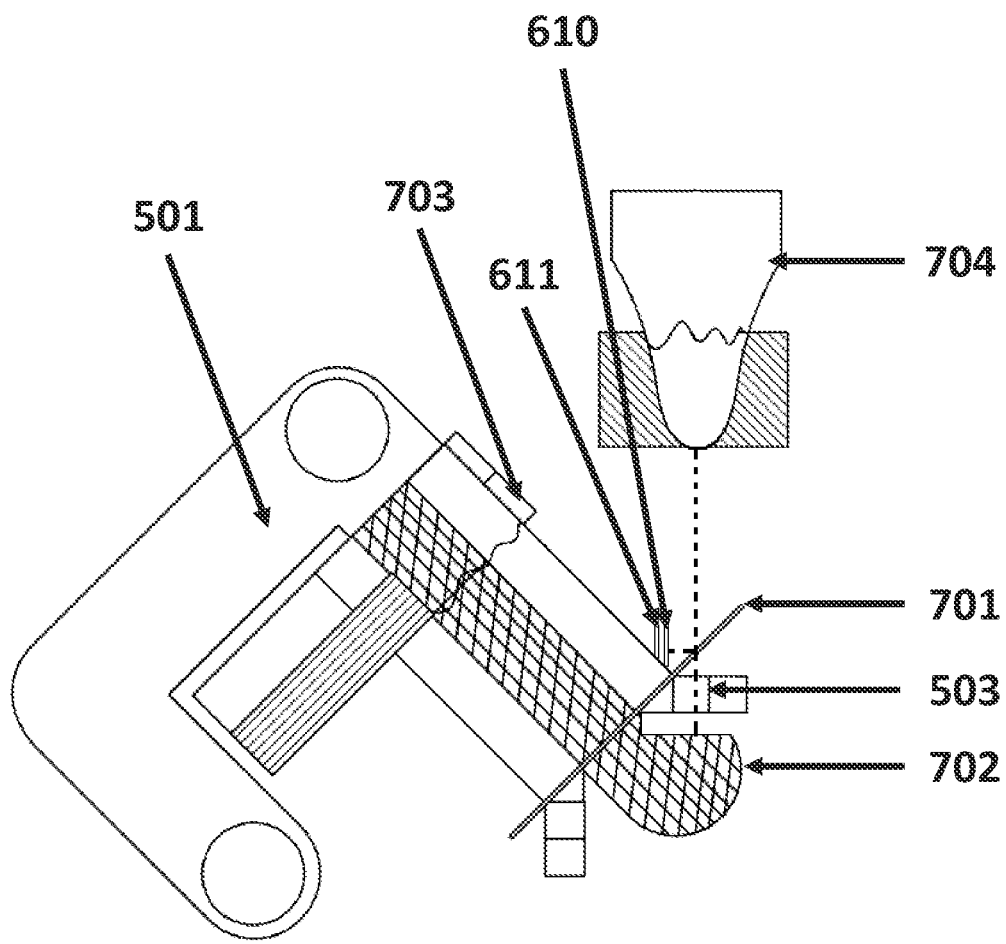
FIG. 7 shows another example of a moving carriage, having optical components (e.g., emission filters, excitation filters, LEDs and/or dichroic beam splitters) that rotate using a pinion mechanism.

FIG. 7 shows an additional configuration for moving carriage 501 in which excitation source 611, excitation filter 610, dichroic beam splitter 701, emission filter 503, and detector 702 are disposed on moving carriage 501. Excitation source 611, excitation filter 610, dichroic beam splitter 701, and emission filter 503 may be disposed on a rotating pinion mechanism 703 such that as moving carriage 501 aligns with each sample, the pinion mechanism may be used to rotate the optical components 611, 610, 701, and 503 to provide to a desired excitation energy to a sample (e.g., a sample in an assay tube), and detect an emission energy from the sample 704.

Figure 8:
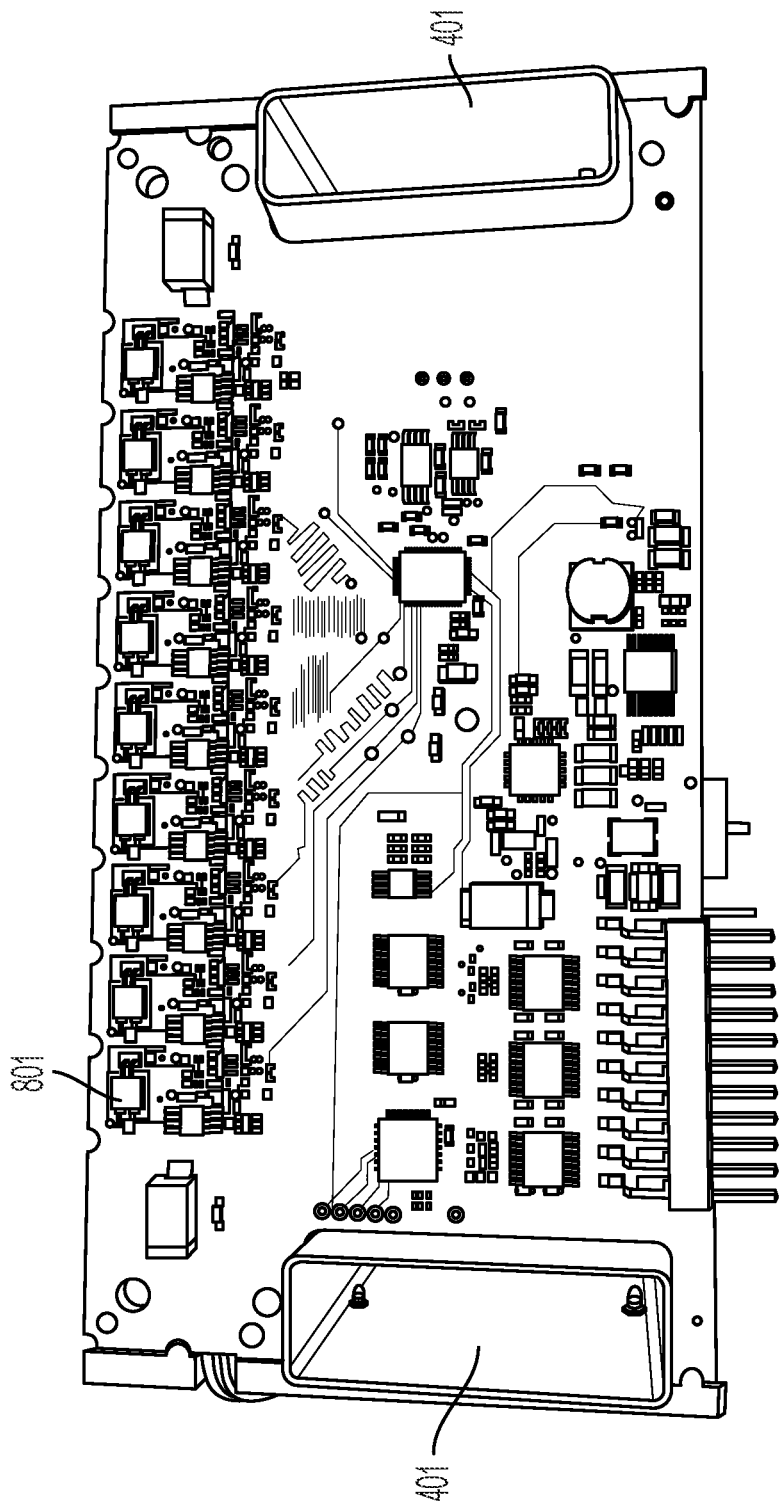
FIG. 8 shows rear view of an internal mechanism for a portable analytic device for analyzing a biological sample.

The analytic device may also comprise a detector such as detector 801, as shown in FIG. 8. The detector may be configured to receive emission energy from a sample (e.g., a sample in an assay tube), and possibly through an emission filter. Accordingly, the detector may comprise any suitable photodetector, such as, for example, an optical detector, a photoresistor, a photovoltaic cell, a photo diode, a phototube, a photomultiplier tube, a charge coupled device (CCD) camera, a complementary metal oxide semiconductor (CMOS), or any combination thereof. Emission energy may be produced by any suitable source, such as, for example, by the excitation of a component of a sample in an assay tube (e.g., an excitable fluorophore). A detector may be configured to selectively receive emission energy from a sample (e.g., energy of a particular wavelength or intensity). A detector may comprise a plurality of detectors (e.g., a series of photodetectors, each configured to receive a light beam having a different wavelength than the light beams received by the other photodetectors).

Figure 14A:
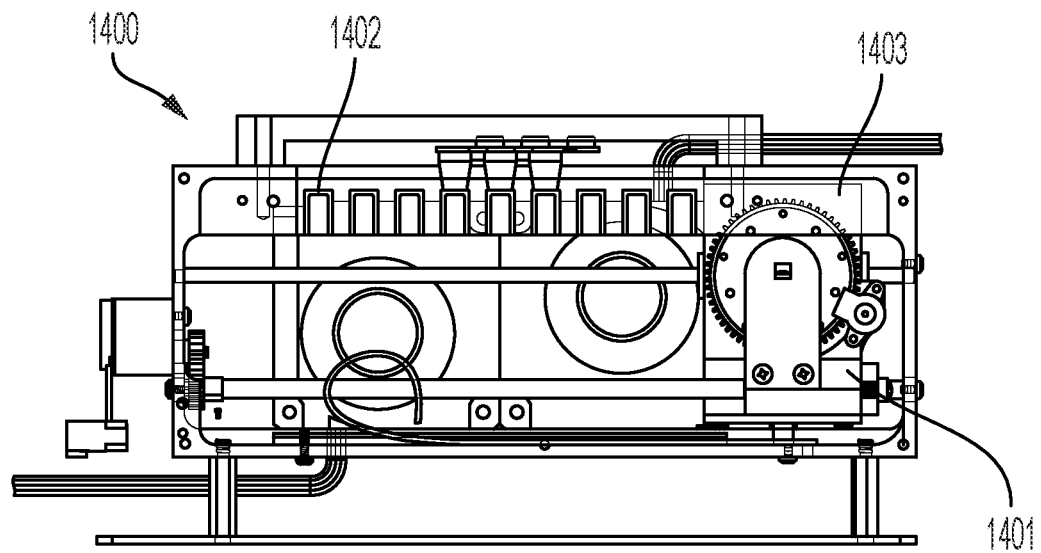
FIG. 14A shows a front view of a movable carriage inside an example portable device.
Figure 14B:
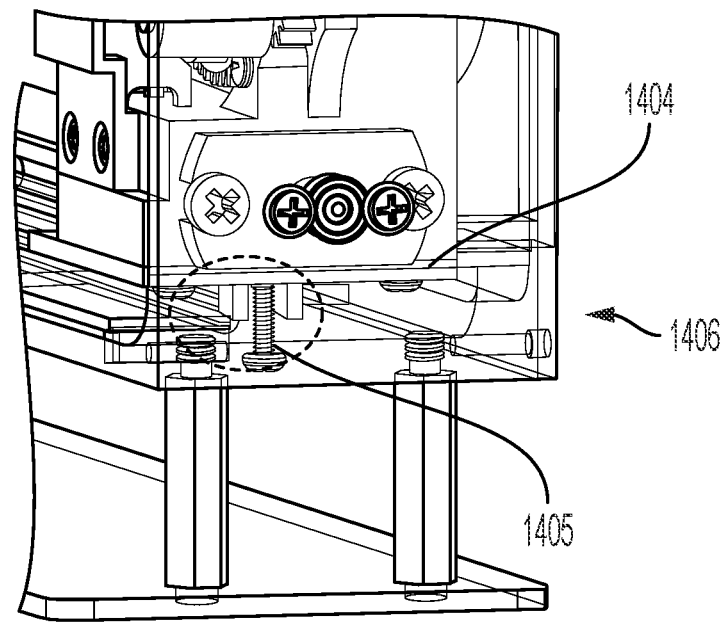
FIG. 14B shows a side view of an example portable device.
Figure 14C:
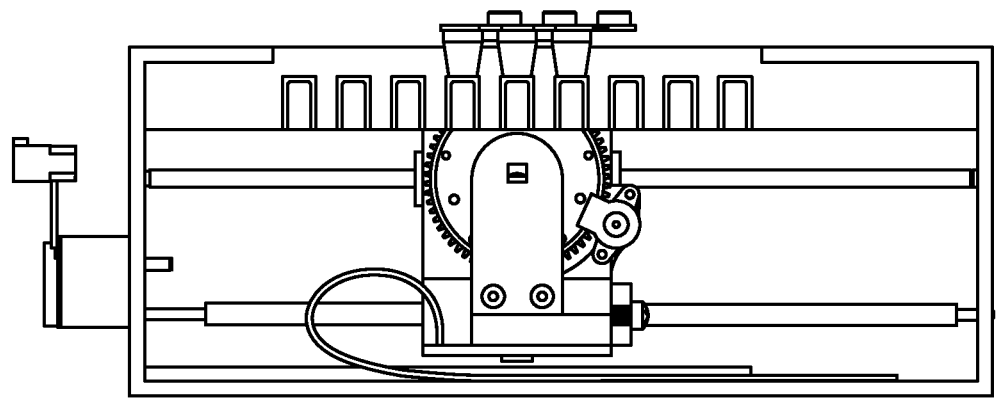
FIG. 14C shows an additional front view of the example movable carriage inside a portable device.
Figure 14D:
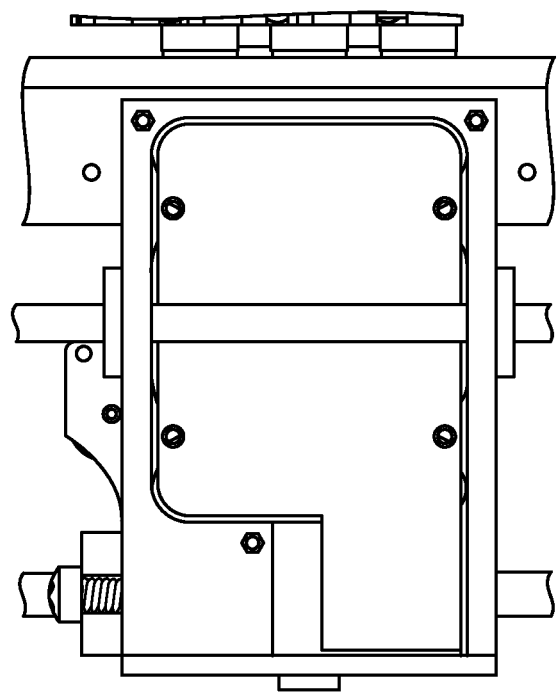
FIG. 14D shows a back view of the example movable carriage.

A movable carriage may comprise a wheel-shaped (or circular) component to carry one or more optical elements, such as filters. As an alternative or in addition to, the wheel-shaped component can include a mirror, light source (e.g., an LED, a single pixel LED, or a multi-pixel LED), prism, lens, or any combination thereof. The movable carriage can be configured to move in a linear path and stopped at a specific position. For example, the movable carriage can be configured to move along the axis of heating blocks and stopped at each heating block for data acquisition from a sample tube inserted into each heating block. The wheel-shaped component inside the movable carriage may be movable along the wheel axle to switch between different filters. For example, FIG. 14A shows a front view of a movable carriage 1401 inside a portable device 1400. In this example device, the wheel-shaped component 1403 of the movable carriage 1401 carries 9 pairs of filters (a pair of filter comprises an excitation filter and an emission filter). The movable carriage can move along the different heating blocks 1402. FIG. 14B shows a zoom-in view of a portion of the movable carriage. The bottom PCB 1404 may comprise a break beam switch. The chassis 1406 can comprise two screws to trigger beam switch to stop carriage from hitting chassis walls. One screw 1405 is shown in FIG. 14B. FIG. 14C shows an additional front view of the example movable carriage stopped at a different position inside a portable device. FIG. 14D shows a back view of the example movable carriage.

The wheel-shaped component can have other shapes. For example, the elements of such wheel-shaped component may be included in a component that is triangular, square, rectangular, pentagonal, hexagonal, or any other shape or combination of shapes thereof.

Figure 15:
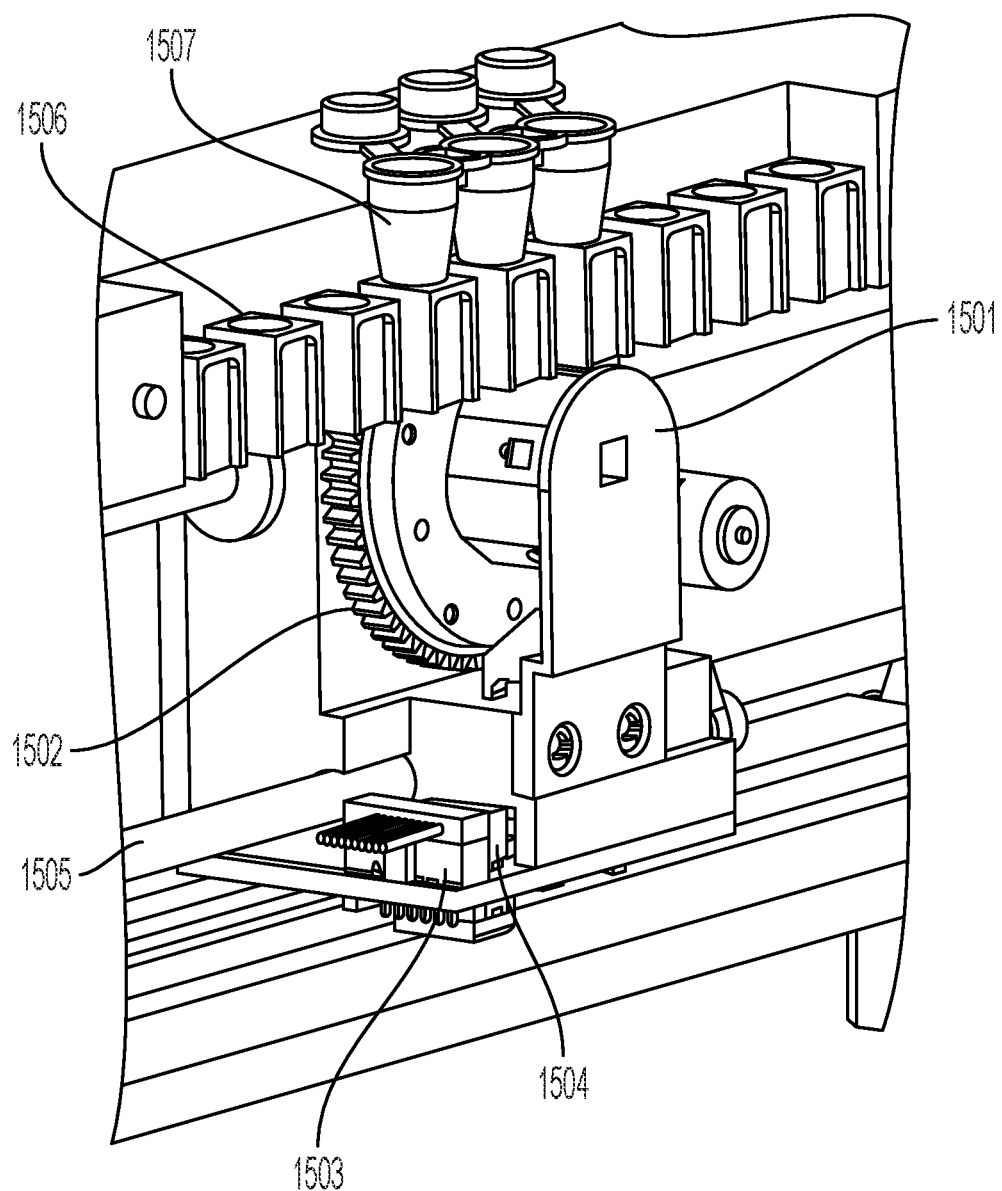
FIG. 15 shows a zoom-in view of an example movable carriage having a circular (or wheel-shaped) component.

FIG. 15 shows a zoom-in view of an example movable carriage 1501 having a wheel-shaped component 1502. The bottom portion of the movable carriage can comprise a ribbon wire 1503 and an actuator (e.g., stepper motor) 1504. The stepper motor 1504 may be used to move the movable carriage along a guide 1505 among the sample stations 1506. A given one of the sample stations 1506 may include a vial 1507 having a solution containing a biological sample and reagents necessary for sample processing (e.g., polymerase chain reaction (PCR)). The movable carriage 1501 may include another actuator (e.g., stepper motor) for rotating the movable carriage 1501 along an axis orthogonal to the guide 1505.

Figure 16:
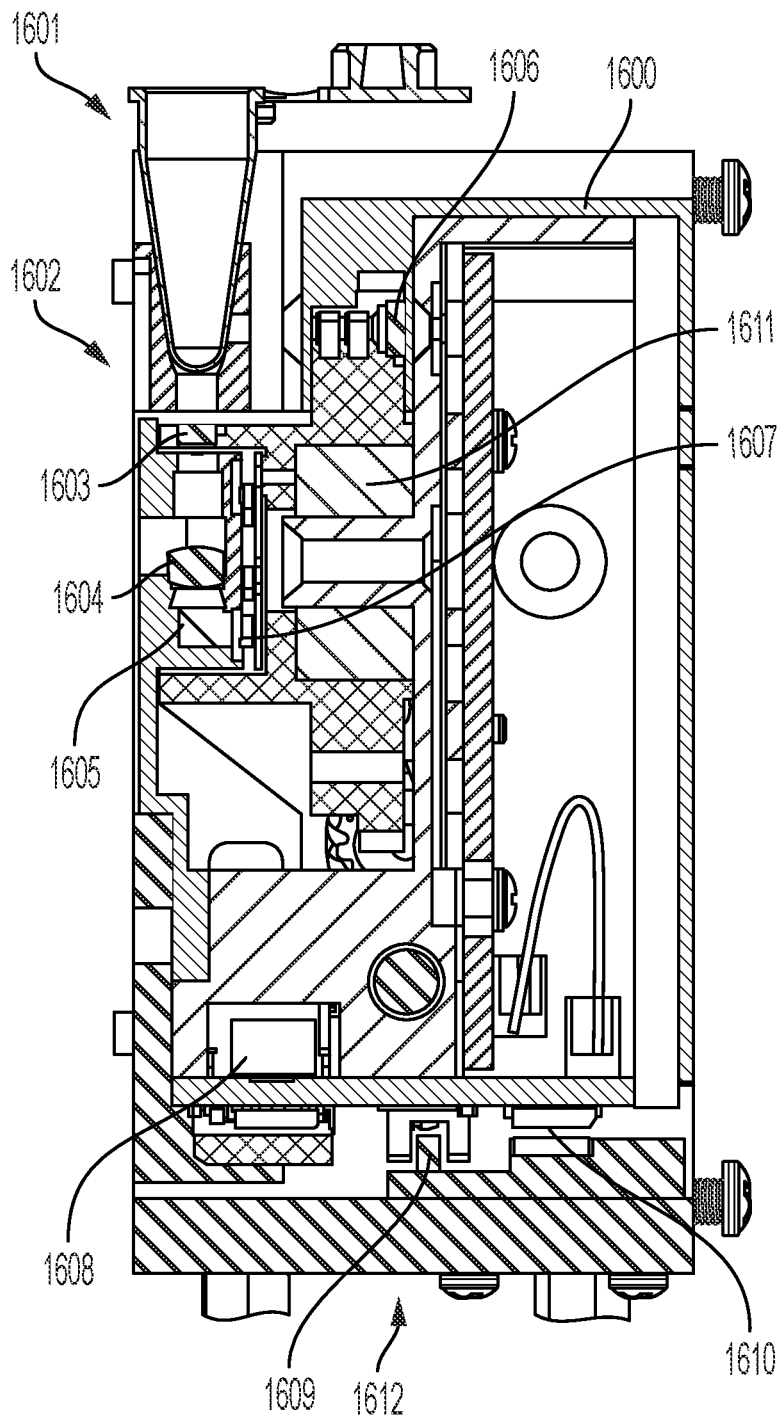
FIG. 16 shows a side view of the internal mechanism of an example movable carriage inside a portable analytic device.
Figure 17:
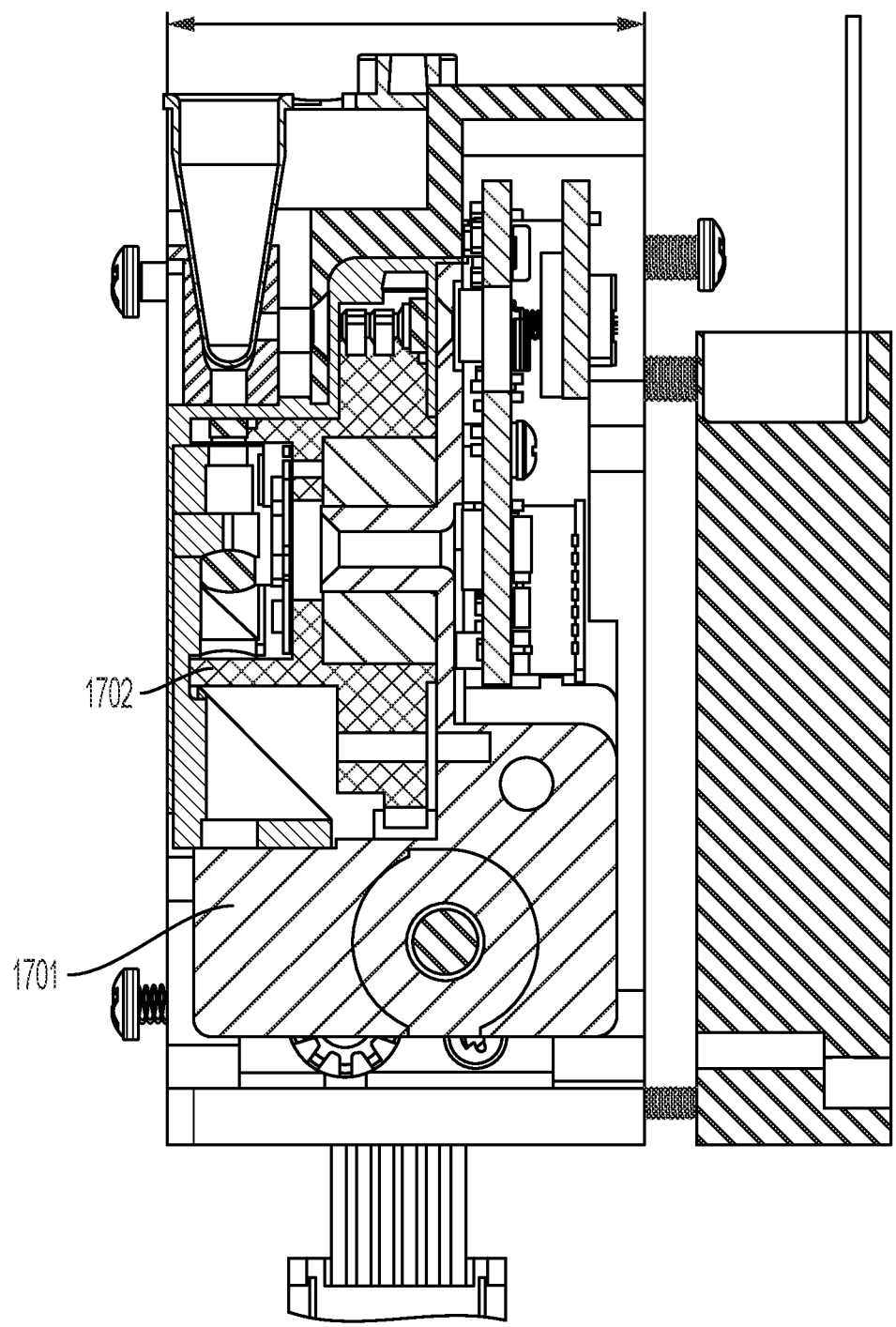
FIG. 17 shows a side view of the internal mechanism of an example movable carriage inside a portable analytic device.

FIG. 16 shows a side view of the internal mechanism of the example movable carriage 1600. The movable carriage can comprise an optical system having an excitation filter 1603, a lens 1604, a mirror 1605, an emission filter 1606, and a light source 1607 (e.g., LED). The movable carriage can comprise one or more magnetic pieces 1611. The movable carriage may comprise multiple excitation filters, emission filters, and light sources. Each light source may be configured to be used with a given pair of excitation filter and emission filter for data acquisition from a sample tube 1601 inserted in a heating block 1602. Shown in FIG. 16 is an example of one optical system having one given pair of excitation and emission filters. When the wheel-shaped component moves around the wheel axle, another option system having another pair of excitation and emission filters and another light source can be lined up with the sample tube for data acquisition. The movable carriage can comprise at least 1, 2, 3, 4, 5, 6, 7, 8, 9, 10, 11, 12, 13, 14, 15, 16, 17, 18, 19, 20 or more filters. The movable carriage can comprise at least one pair, two pairs, three pairs, four pairs, five pairs, six pairs, seven pairs, eight pairs, nine pairs, ten pairs, eleven pairs, twelve pairs, thirteen pairs, fourteen pairs, fifteen pairs, or more pairs of filters. The movable carriage can further comprise a big capacitor 1608. The chassis 1612 of the device can comprise a flag 1609 to trigger a photo interrupter. The chassis 1612 can comprise a magnetic strip and linear encoder 1610 (e.g., a liner encoder having a 0.4 mm gap). The movable carriage can be built with various materials or combinations of materials. For example, shown in FIG. 17, the part 1701 of the movable carriage can be built with metal. The part carrying the optical system 1702 may be built with black dyed micro fine 3D print. The detector board may be fully enclosed for EMI shielding.

Figure 18:
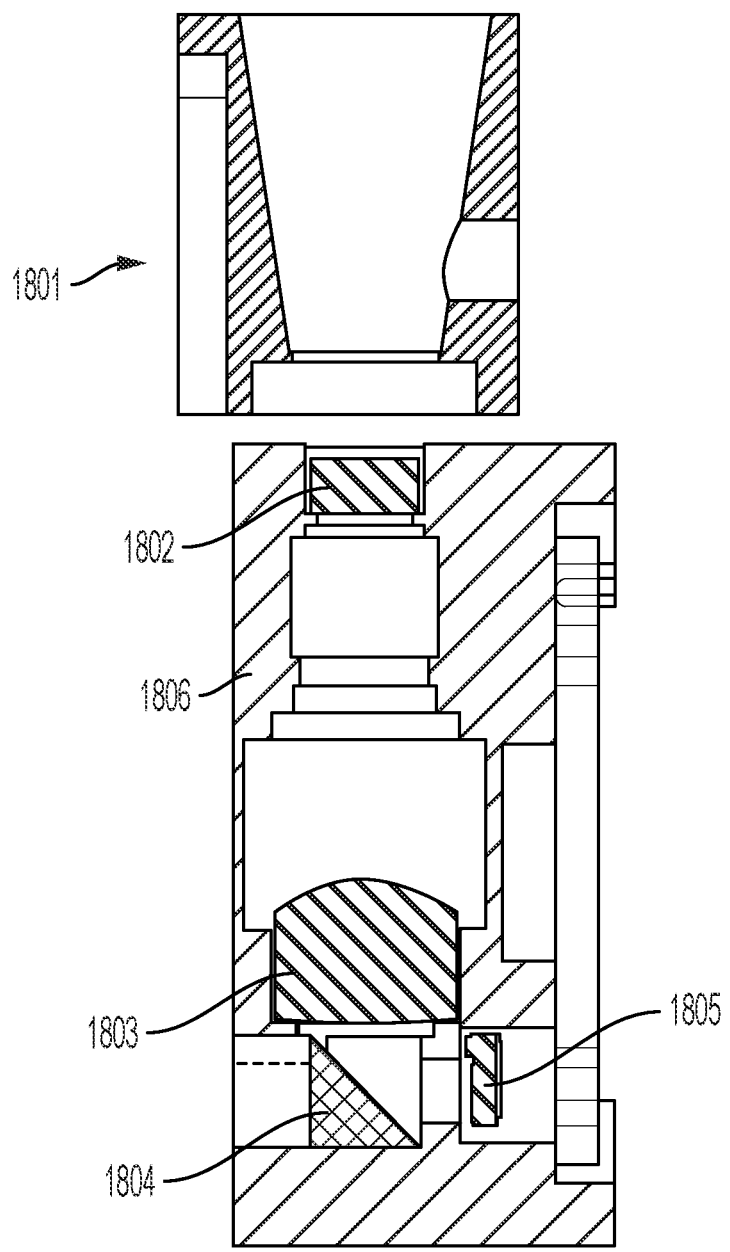
FIG. 18 shows a zoom-in view of an example optical system of the movable carriage.

FIG. 18 shows a zoom-in view of an example mechanism of an optical system of the movable carriage. The lens 1803 can be made of various materials, for example, glass or polycarbonate. The lens 1803 may be mounted in a non-rotating part of the hub 1806 of the wheel-shaped component. The light source (or excitation source) 1805 can be a LED light. The filter 1802 can be an excitation filter. The filter 1802 may provide transmission of a desired excitation wavelength. For example, the light transmitted from the excitation filter may have a center wavelength of at least about 390 nanometers (nm), 434 nm, 445 nm, 469 nm, 475 nm, 497 nm, 542 nm, 559 nm, or 565 nm. The optical system can further comprise a fold mirror 1804. The distance between the light source 1805 and the fold mirror 1804 can vary. Shown in FIG. 18, the part 1801 is a heating block. In addition, the optical system can comprise an emission filter. The emission filter can provide transmission of a desired emission wavelength. For example, the light transmitted from the emission filter may have a center wavelength of at least about 460 nm, 479 nm, 510 nm, 525 nm, 530 nm, 535 nm, 620 nm, or 630 nm. In some cases, the optical system inside a movable carriage may comprise one or more dichroic filters.

Figure 19A:
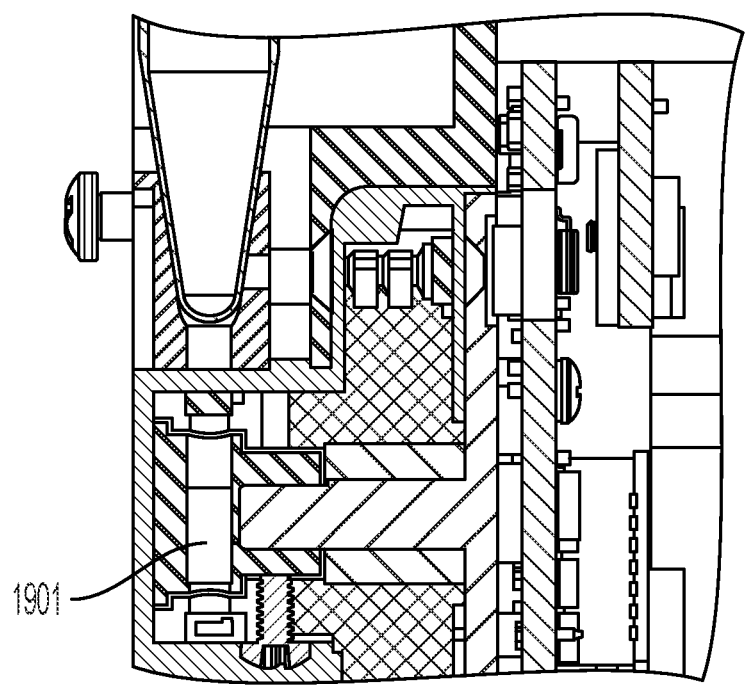
FIG. 19A shows an alternative configuration of the optical system.
Figure 19B:
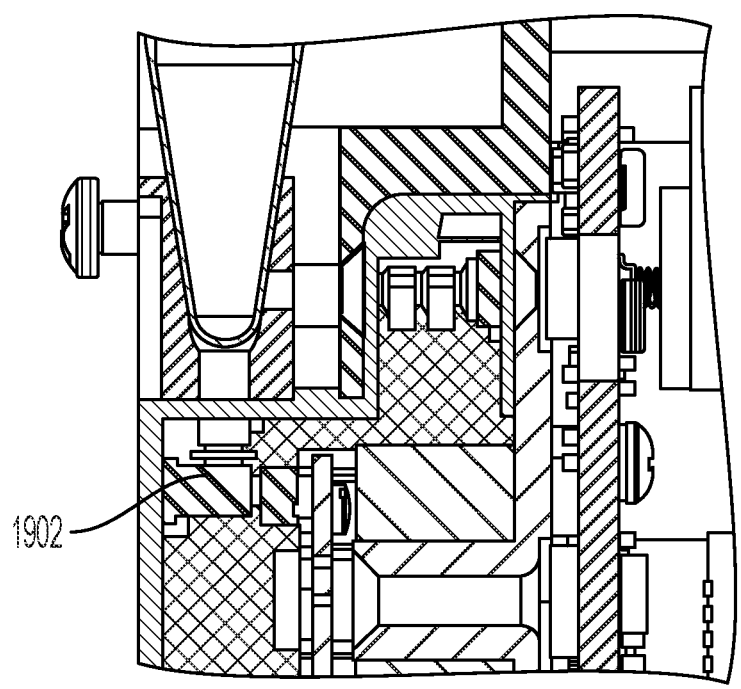
FIG. 19B shows another alternative configuration of the optical system.

The optical system may comprise different components and can be assembled in different configurations. FIGS. 19A and 19B show two additional examples of the optical systems inside of a movable carriage. For example, an optical system of the movable carriage may not comprise a mirror and lens. An optical system may comprise a light path 1901 that allow the light from a light source to reach an excitation filter. For another example, an optical system may comprise a prism 1902 to allow the light from a light source to reach the excitation filter.

Different configurations of the optical systems may result in different properties of the system as demonstrated by parameters such as power to vial, moving carriage baseline, signal to noise ratio (SNR), etc. As used herein, the SNR can be defined using the following equation:

$$SNR = \frac{\text{Total power on detector}}{\text{Power on filter outside} \times \text{degrees that reaches the detector}}$$

where, x is the incidence angle of a light.

Figure 20A:
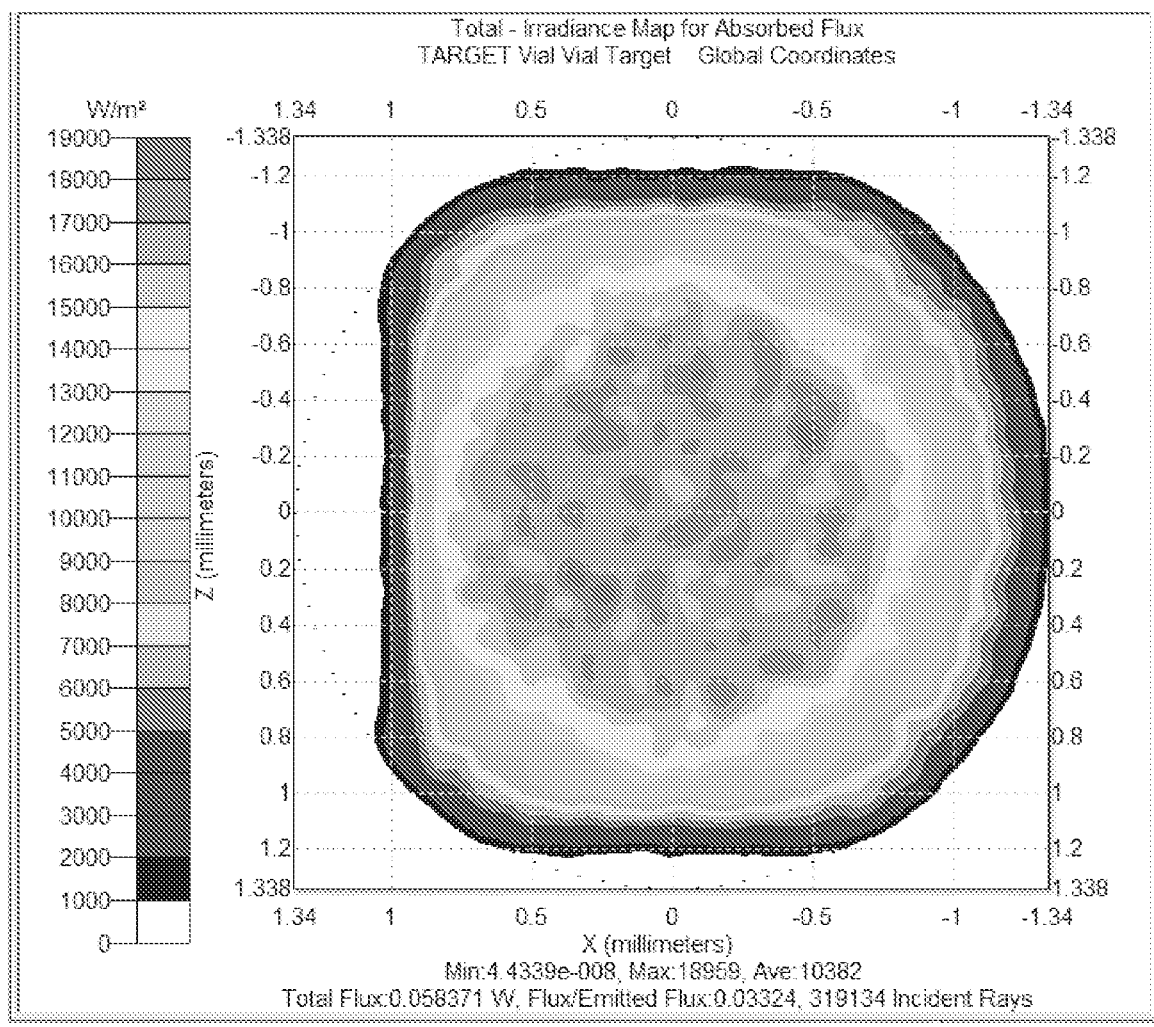
FIG. 20A shows a simulation result of an optical system.
Figure 20B:
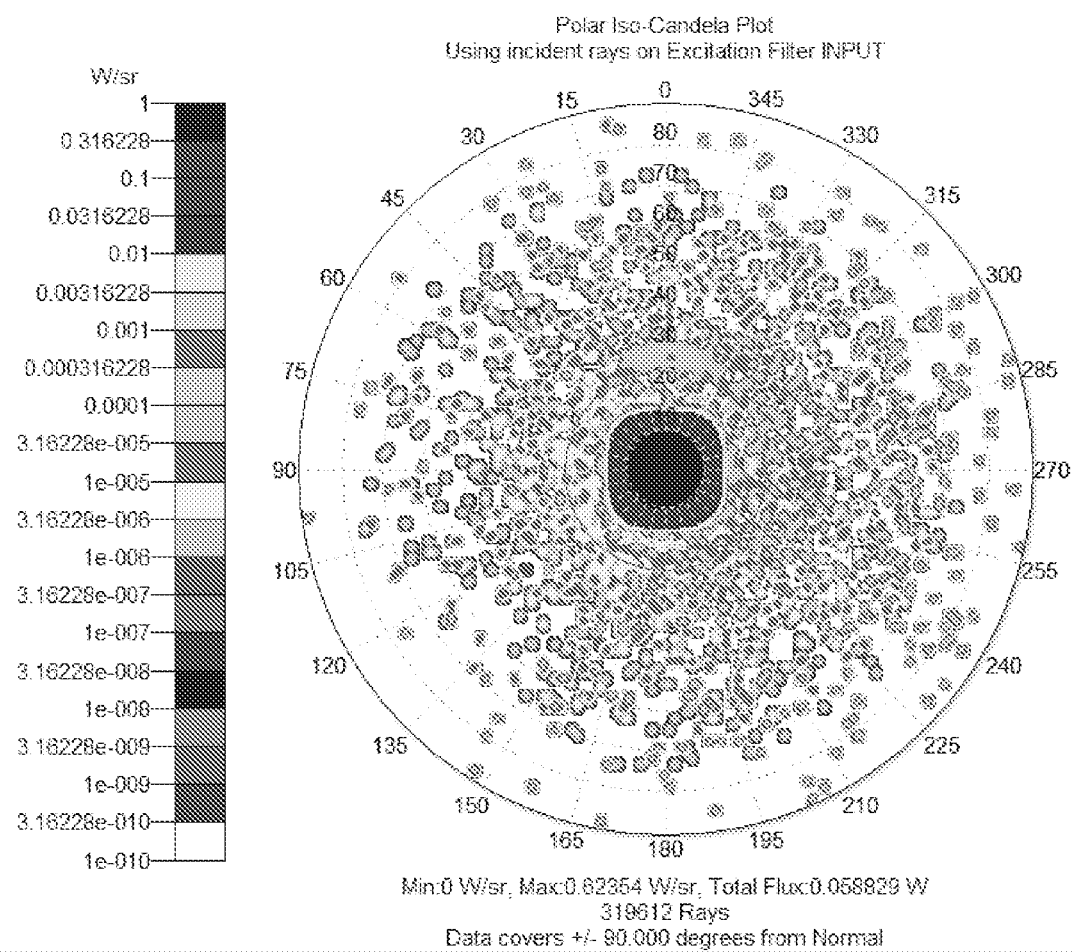
FIG. 20B shows another simulation result of an optical system.
Figure 20C:
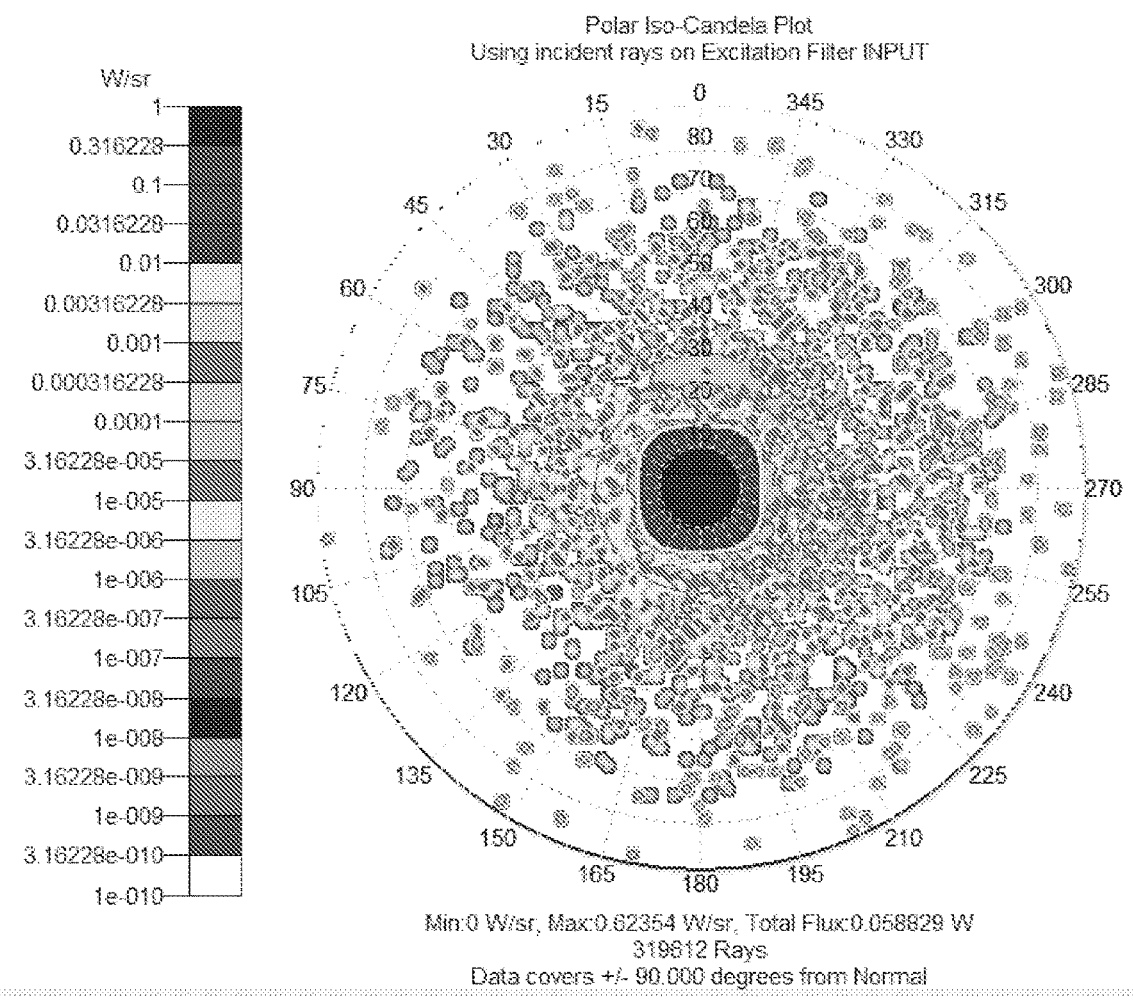
FIG. 20C shows another simulation result of an optical system.
Figure 21A:
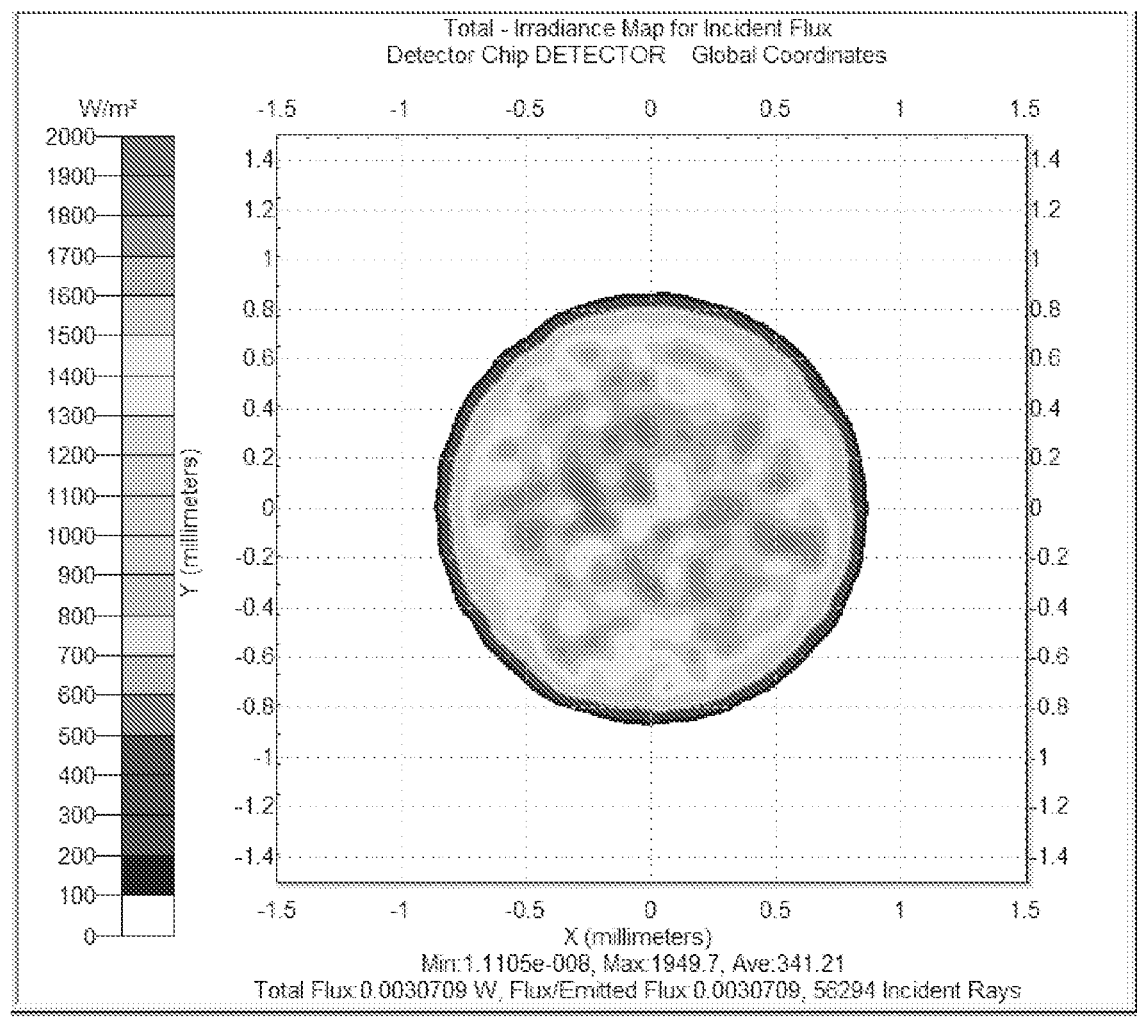
FIG. 21A shows a simulation result of an optical system.
Figure 21B:
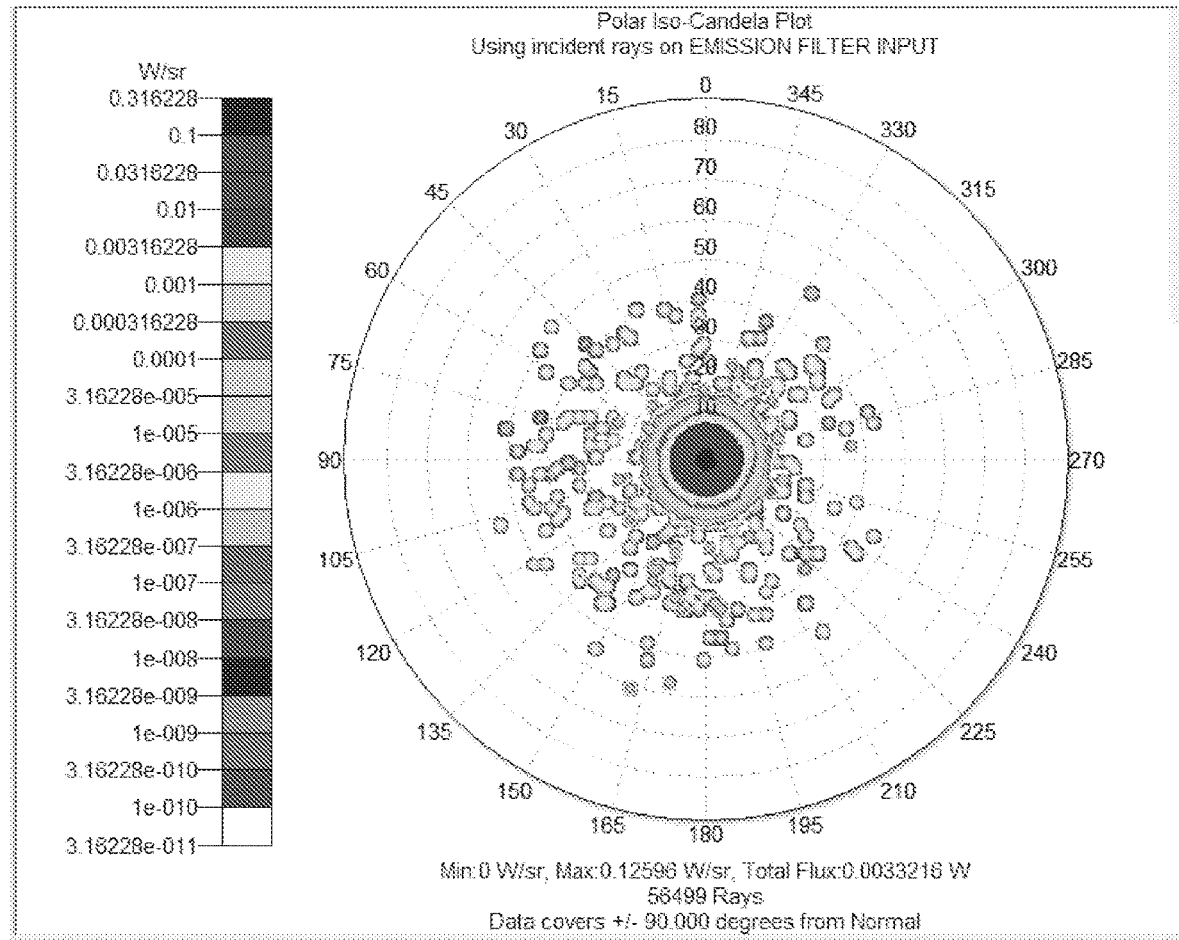
FIG. 21B shows another simulation result of an optical system.
Figure 21C:
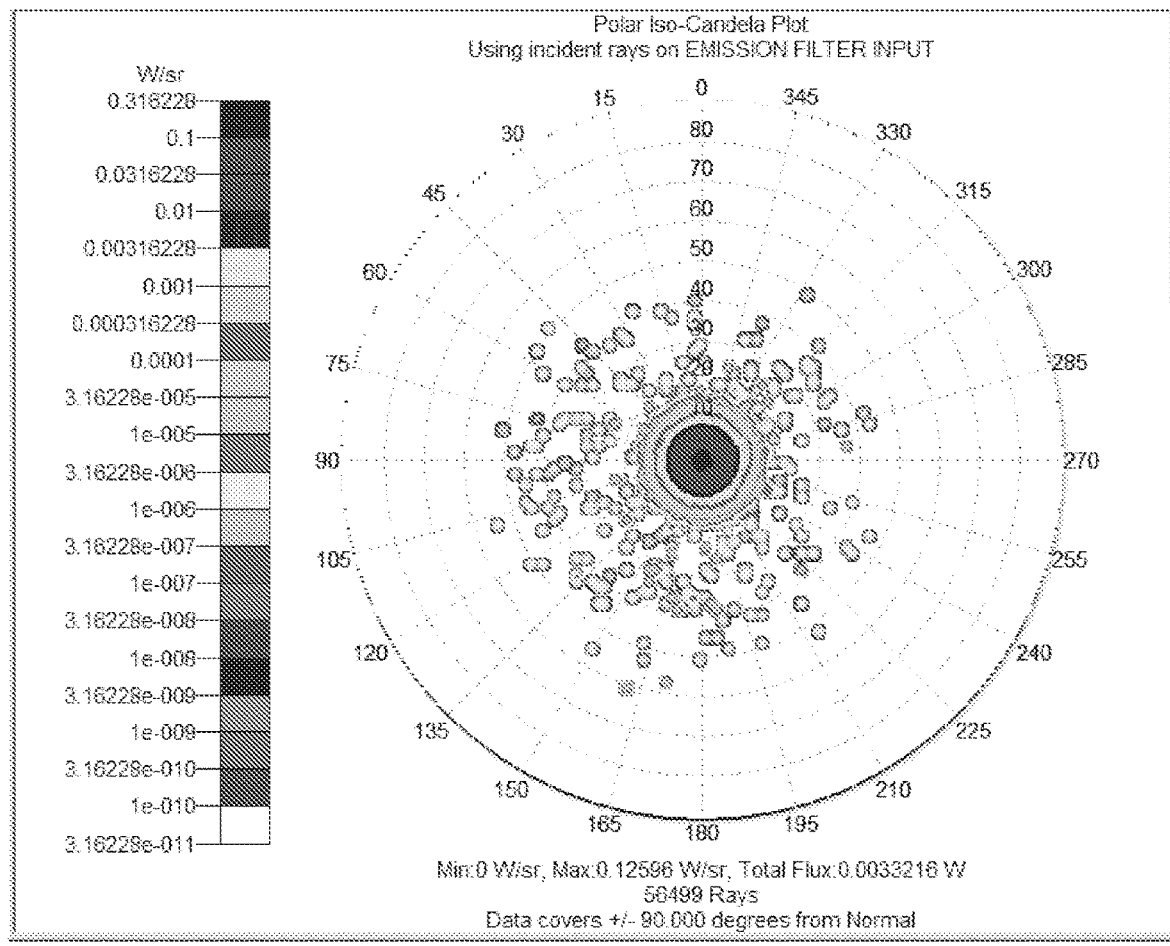
FIG. 21C shows another simulation result of an optical system.

In some cases, x may be 25 degrees on excitation and 15 degrees on emission. "Power to vial" refers to the total optical power making it into the vial that is available for excitation of fluorescent probes. "Moving carriage baseline," as used herein, refers to a baseline used for comparing different configurations of the optical system. Example data shown in the present disclosure are baselined against the design without a wheel-shaped component, for example, as shown in FIGS. 7 and 8. Using the parameters described herein, the properties of different configurations can be tested by excitation simulation. For example, an optical system can have a power to vial value of about 2%, 3%, 4%, 5%, 6%, 7%, 8%, 9%, 10% or more. The optical system can be 1 fold, 1.5 fold, 2 fold, 2.5 fold, 3 fold, 3.5 fold, 4 fold, 5 fold, 6 fold, 7 fold, 8 fold, 9 fold, 10 fold, 15 fold, 20 fold, or more efficient than the moving carriage baseline. The SNR of the optical system can be at least 1,000, 1,500, 2,000, 2,500, 3,000, 3,500, 4,000, 5,000 or more. In some case, the SNR of the optical system can be at least 100, 150, 200, 250, 300, 350, 400, 450, 500 or more. For example, a configuration shown in FIG. 16 have a power to vial value of 5.8%, 2 to 20 fold more efficient than the moving carriage baseline, and have a SNR value of about 2,000. FIGS. 20A-20C and 21A-20C show example simulation results of the optical system. FIG. 20A shows the power to vial value of 5.8% of the tested carriage having a fold mirror configuration. FIG. 20B shows the total power on filter of 5.9%. FIG. 20C shows the SNR calculated at 25 degrees to be 2112. FIG. 21A shows the power to detector of 0.31% of the tested carriage having a fold mirror configuration. FIG. 21B shows the power on filter of 0.33%. FIG. 21C shows the SNR calculated at 15 degrees to be 3067.

Figure 10:
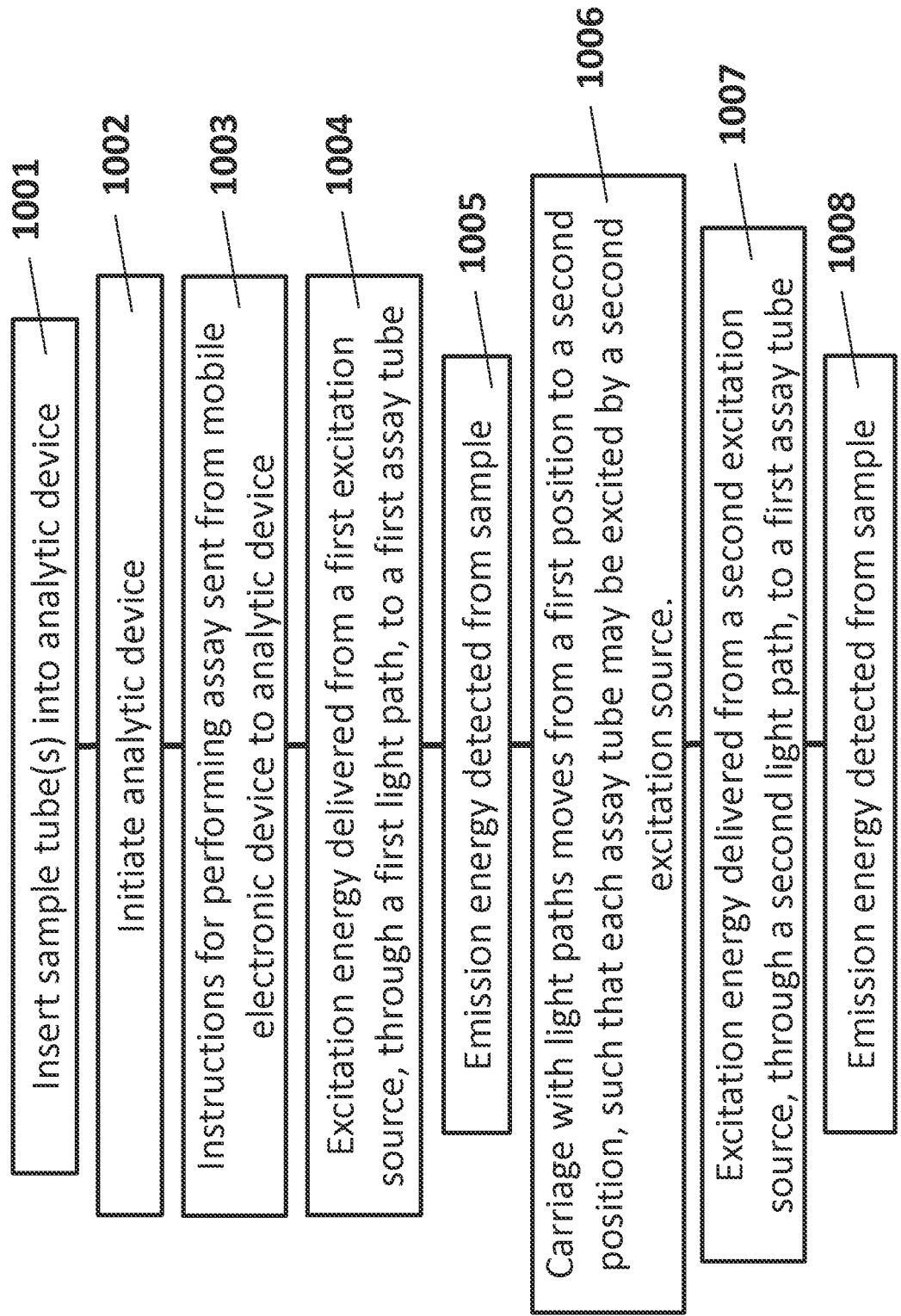
FIG. 10 shows a flow chart of an example method of analyzing a biological sample using a portable analytic device of the present disclosure, such as the device of FIG. 2A.

FIG. 10 shows an example process flow for the analytic device of FIGS. 1A-1B. In a first operation 1001, lid 101 of housing 100 is opened, and a user inserts one or more assay tubes each containing a sample into the analytic device. In a second operation 1002, the user initiates the analytic device by pressing power button 103 located on housing 100. In a third operation 1003, the user provides instructions for performing an amplification reaction (e.g., a thermal cycling assay). The instructions may be provided using an application on a mobile electronic device (e.g., which may be physically detached from the analytic device, integrated into the analytic device, or removably disposed in or on the analytic device, for example in a housing or groove of the analytic device). Instructions provided to the application may then be communicated to the analytic device (e.g., via a wireless connection, as described herein). In a fourth operation 1004, the analytic device is initiated, and an excitation energy is delivered from excitation source 611, through excitation filter 610, through light path 502, to a first assay tube. In a fifth operation 1005, emission energy from the sample in the first assay tube is delivered from the sample through emission filter 503 to detector 801. In a sixth operation 1006, a moving carriage comprising excitation source 611, excitation filter 610, and emission filter 503 may move to a second position (e.g., aligning light path 502 with a second assay tube). In a seventh operation 1007, excitation energy is delivered from a second excitation source, through a second excitation filter, through a second light path, to the first assay tube. In an eighth operation 1008, emission energy from the sample in the first assay tube is delivered from the sample through a second emission filter and to detector 801.

Methods of Configuring Analytic Devices

The present disclosure provides methods for configuring or programming an analytic device. The present disclosure also provides methods for unlocking features in an analytic device.

An analytic device may comprise a locked function. The locked function can be unlocked through an instruction received from a remote server. For example, the analytic device may comprise a light path configured to provide excitation energy to a biological sample, but the light path can be locked such that the light path is unable to provide the excitation energy. Upon receiving one or more instructions from a remote server, the analytic device can be configured to unlock the light path such that it is able to provide the excitation energy. For another example, the analytic device may comprise an optical detector configured to detect optical signals from a biological sample over a plurality of optical frequencies comprising a first set of optical frequencies and a second set of optical frequencies different than the first set of optical frequencies, but the analytic device can output data corresponding to the first set of optical frequencies not the second set of optical frequencies. Upon receiving one or more instructions from a remote server, the analytic device can be configured to unlock a function such that it can output data corresponding to the second set of optical frequencies. For another example, the analytic device may comprise a locked function to detect or generate melting curves of a biological sample. Upon receiving one or more instructions from a remote server, the analytic device can be configured to unlock the function such that it can detect or generate melting curves of the biological sample. The analytic device may be configured to unlock an additional light path, a color channel, or a light source. The analytic device may be configured to unlock an additional function to perform an assay, e.g., high resolution melt analysis. The functions of the analytic device to be unlocked can be non-limiting.

The method for unlocking features in an analytic device may comprise providing the analytic device configured to perform a first assay and a second assay. The first assay may be unlocked such that the analytic device can perform the first assay on a first biological sample and output data corresponding to the first assay. The second assay may be locked such that the analytic device does not perform the second assay or output data corresponding to the second assay. Next, the second assay may be unlocked by instructions received over a network. Next, the second assay can be unlocked such that the analytic device can perform the second assay on a second biological sample or outputs data corresponding to the second assay when the second assay is performed on the second biological sample.

The method for configuring or programming an analytic device may comprise providing the analytic device configured to perform a first assay and a second assay on a first biological sample. The second assay may be different from the first assay. The analytic device may be programmed to output data corresponding to the first assay but not output data corresponding to the second assay. Next, one or more instructions from a remote server may be received over a network. The one or more instructions may be usable to configure or program the analytic device to output data corresponding to the second assay. Next, the one or more instructions may be used to program the analytic device such that the analytic device can output data corresponding to at least the first assay and the second assay when assaying a second biological sample. The first assay can be a thermal cycling assay. The thermal cycling assay can comprise heating and cooling of a biological sample. The second assay can be a melting curve assay. The melting curve assay can comprise heating a biological sample over a range of temperatures at a temperature increment. The temperature increment may be at least about 0.1° C., 0.2° C., 0.3° C., 0.4° C., 0.5° C., 0.6° C., 0.7° C., 0.8° C., 0.9° C., 1° C., or higher. The first biological sample and the second biological sample may be the same or different.

The method for configuring or programming an analytic device may comprise providing the analytic device configured to perform a thermal cycling assay and a melting curve assay of a first biological sample. The analytic device may be programmed to output data corresponding to the thermal cycling assay but not output data corresponding to the melting curve assay when assaying the first biological sample. Next, the one or more instructions may be received over a network from a remote server. The one or more instructions may be usable to configure the analytic device to output data corresponding to the melting curve assay. The one or more instructions may be used to configure or program the analytic device such that the analytic device can output data corresponding to at least the thermal cycling assay and the melting curve assay when assaying a second biological sample. The analytic device may comprise a heating block comprising a recess configured to receive an assay tube. The analytic device may further comprise a heating unit in thermal communication with the heating block. The heating unit can provide thermal energy to the heating block. The analytic device may further comprise a cooling unit. The cooling unit can reduce the thermal energy from the assay tube.

The method of configuring or program an analytic device may comprise providing the analytic device for assaying a biological sample. The analytic device comprises a locked function. The analytic device can comprise an optical detector configured to detect optical signals from a first biological sample over a plurality of optical frequencies comprising a first set of optical frequencies and a second set of optical frequencies different than the first set of optical frequencies. The analytic device can be configured or programed to output data corresponding to the first set of optical frequencies but not output data corresponding to the second set of optical frequencies when assaying the first biological sample. Next, one or more instructions can be received from a remote server over a network. The one or more instructions may be usable to configure or program the analytic device to output data corresponding to the second set of optical frequencies. The one or more instructions can be used to configure or program the analytic device such that the analytic device outputs data corresponding to at least the first set of optical frequencies and the second set of optical frequencies when assaying a second biological sample. The optical signals can comprise emission energy.

An example method comprises (a) providing a analytic device comprising an optical detector configured to detect optical signals from a first biological sample over a plurality of optical frequencies comprising a first set of optical frequencies and a second set of optical frequencies different than the first set of optical frequencies, wherein the analytic device is configured to output data corresponding to the first set of optical frequencies but not output data corresponding to the second set of optical frequencies when assaying the first biological sample; (b) receiving, over a network, one or more instructions from a remote server, which one or more instructions are usable to configure or program the analytic device to output data corresponding to the second set of optical frequencies; and (c) using the one or more instructions to configure or program the analytic device such that the analytic device outputs data corresponding to at least the first set of optical frequencies and the second set of optical frequencies when assaying a second biological sample.

The analytic device can comprise a housing with a volume that is less than about 1,500 cubic centimeters. The analytic device can comprise at least one heating block within the housing. The at least one heating block can comprise a recess configured to receive an assay tube. The assay tube can comprise a biological sample, e.g., the first or second biological sample. In some cases, the analytic device comprises two or more heating blocks. The analytic device can comprise at least one heating unit in thermal communication with the at least one heating block. The at least one heating unit can provide thermal energy to the assay tube through the at least one heating block. The at least one heating unit can comprise a resistive heater. The at least one heating unit can be thermally cured to the at least one heating block. The at least one heating unit can be soldered to the at least one heating block. The analytic device can comprise a cooling unit disposed within the housing. The cooling unit can reduce the thermal energy from the assay tube.

The first set of optical frequencies can comprise a first color and the second set of optical frequencies can comprise a second color different than the first color. The first color can be any color on the color spectrum, e.g., green, amber, and red. The second color can be any color on the color spectrum different than the first color.

The analytic device can comprise a lighting unit. The lighting unit can comprise at least one light path comprising an excitation filter and an emission filter. The at least one light path can be configured to provide excitation energy from a light source to the assay tube (or to the first or second biological sample). The at least one light path can comprise one or more light pipes to convey the excitation energy from the light source to the first or second biological sample. The one or more light pipes can comprise a first end comprising a single pipe, a second end comprising two or more pipes, and a branching portion therebetween.

The analytic device can comprise a lighting unit comprising a plurality of light sources configured to provide excitation energy at a plurality of different frequencies or frequency ranges. The lighting unit can be configured to bring a light source of the plurality of light sources in optical alignment with a light path that is in optical communication with the assay tube (or the first or second biological sample). The light source can be configured to provide light at a frequency or frequency range from the plurality of different frequencies or frequency ranges. The lighting unit may be rotatable along an axis. The lighting unit may be translatable along an additional axis orthogonal to the axis. The lighting unit may be translatable along the additional axis to remove the light path from alignment with the assay tube (or the first or second biological sample).

The analytic device can comprise a movable carriage comprising an excitation filter and an emission filter. The movable carriage can be configured to translate to bring the excitation filter and the emission filter to a first position in alignment with a light path that provides excitation energy from the excitation source to the assay tube (or the first or second biological sample). The movable carriage can comprise a plurality of light paths. The analytic device can further comprise an actuator for moving the movable carriage from the first position to a second position.

The light source can be an excitation source. The excitation source can comprise one or more light emitting diodes (LEDs). The one or more LEDs can comprise single-color LEDs. The one or more LEDs can comprise a plurality of LEDs, and each of the plurality of LEDs can be configured to emit a different frequency of the excitation energy.

The method of configuring the analytic device can further comprise assaying the first biological sample. In some embodiments, assaying the first biological sample is performed subsequent to providing the analytic device. In some embodiments, assaying the first biological sample is performed before configuring the analytic device using the one or more instructions to unlock the additional function. Next, the first set of optical frequencies and/or the second set of optical frequencies can be detected. An error signal or a warning signal may be received indicative of inability to output the second set of optical frequencies when detecting the second set of optical frequencies. The warning signal may suggest upgrading software to unlock the function to output the second set of optical frequencies. Next, a request may be directed to the remote server for the one or more instructions.

The analytic device may comprise a processing unit or a computer processor. The processing unit of the analytic device can comprise a circuit within the housing. The processing unit can be configured to communicate with a mobile electronic device. The mobile electronic device may be external to the housing. The analytic device can further comprise a communication unit. The communication unit can provide wireless connection between the processing unit and the mobile electronic device. The wireless connection may be a WiFi connection, a Bluetooth connection, a Bluetooth LE connection, an ANT+ connection, or a Gazell connection. The mobile electronic device can be a phone, a laptop, a computer, or an iPad. The phone may be a smart phone. The mobile electronic device can be a device that can perform wireless communication with the analytic device.

The mobile electronic device can be used to transfer instructions between the analytic device and the remote server. The mobile electronic device can comprise a program or computer software to receive and send instructions between the analytic device and the remote server. The mobile electronic device can comprise an APP to receive and send instructions between the analytic device and the remote server. The mobile electronic device can be used to direct the request to the remote server for the one or more instructions. The mobile electronic device can be used to receive the one or more instructions from the remote server. The mobile electronic device can be used to direct the request to the remote server for the one or more instructions, and/or receive the one or more instructions from the remote server. Upon receiving the one or more instructions, the mobile electronic device can be used to send instructions to the processing unit to configure the analytic device. The processing unit can be configured to receive instructions from the mobile electronic device external to the housing for processing a biological sample, e.g., the first or second biological sample. In response to the instructions, the processing unit can be used direct the at least one heating unit to provide thermal energy to the at least one heating block to provide heat to the first or second biological sample, and/or direct the excitation source to provide the excitation energy.

The analytic device can be configured to unlock the function to detect one or more additional optical frequencies. The analytic device can be configured to unlock the function to output data corresponding to one or more additional sets of optical frequencies. For example, the one or more instructions can be used to configure the analytic device such that the analytic device outputs data corresponding to at least the first set of optical frequencies, the second set of optical frequencies and a third set of optical frequencies when assaying a second biological sample. The third set of optical frequencies can be different than the first set of optical frequencies and the second set of optical frequencies. Next, data corresponding to at least the first set of optical frequencies and the second set of optical frequencies when assaying the second biological sample can be output.

Systems for Assaying Biological Samples

The present disclosure also provides systems for biological sample assaying. A system for biological assaying may comprise an analytic device with one or more locked functions or features. When locked, a user may not be permitted to use such functions or features, or data from such functions or features may not be accessible by the user. The one or more locked functions or features can be unlocked, for example, through one or more instructions received from a remote server. When unlocked, the user may be permitted to use such functions or features, or data from such functions or features may be accessible by the user. The one or more functions that can be unlocked or activated include, but are not limited to, running or outputting data for melt curve protocols, running or outputting data for high resolution melt analysis, running or outputting data for quantification analysis, running or outputting data for thermal cycling certain blocks, and running or outputting data for a maximum number of tests.

A system for unlocking features in an analytic device may comprise an analytic device configured to perform a first assay and a second assay. The first assay may be unlocked such that the analytic device can perform the first assay on a first biological sample and output data corresponding to the first assay. The second assay may be locked such that the analytic device cannot perform the second assay or output data corresponding to the second assay. The system may further comprise one or more computer processors operatively coupled to the analytic device. The one or more computer processors can be individually or collectively programmed to (i) receive over a network instructions to unlock the second assay, and (ii) unlock the second assay such that the analytic device can perform the second assay on a second biological sample or output data corresponding to the second assay when the second assay is performed on the second biological sample. The system may further comprise a housing. The analytic device and the one or more computer processors can be within the housing. The analytic device can be within the housing, and the one or more computer processors can be external to the housing.

A system for biological sample assaying may comprise an analytic device configured to perform a first assay and a second assay on a first biological sample. The second assay may be different from the first assay. The analytic device can be configured to output data corresponding to the first assay but not output data corresponding to the second assay. The one or more computer processors can be operatively coupled to the analytic device. The one or more computer processors can be individually or collectively programmed to receive, over a network, one or more instructions from a remote server. The one or more instructions can be usable by the one or more computer processors to program the analytic device to output data corresponding to the second assay. The one or more computer processors can be individually or collectively programmed to use the one or more instructions to program the analytic device such that the analytic device can output data corresponding to the first assay and the second assay when assaying a second biological sample.

The first assay can be a thermal cycling assay. The first assay can be a melting curve assay. The first assay can comprise detecting an optical frequency of a sample. The thermal cycling assay may comprise heating and cooling of the first or second biological sample. The melting curve assay can comprise heating or cooling the first or second biological sample over a range of temperatures, in some cases by increasing or decreasing the temperature of the first or second biological sample (or a solution having the first or second biological sample) at a temperature increment. The temperature increment may be at least about 0.1° C., 0.2° C., 0.3° C., 0.4° C., 0.5° C., 0.6° C., 0.7° C., 0.8° C., 0.9° C., 1° C., or higher. The second assay can be a melting curve assay. The second assay can be a thermal cycling assay. The second assay can comprise detecting one, two, three, four, five, six, seven, eight, night, or ten more optical frequencies of a sample than the first assay.

The first biological sample and the second biological sample can be same or different.

The system may further comprise a housing. The analytic device and the one or more computer processors can be within the housing. The analytic device can be within the housing, and the one or more computer processors can be external to the housing.

A system provided herein can comprise an analytic device comprising an optical detector configured to detect optical signals from a first biological sample over a plurality of optical frequencies comprising a first set of optical frequencies and a second set of optical frequencies different than the first set of optical frequencies. The analytic device can be configured to output data corresponding to the first set of optical frequencies but not output data corresponding to the second set of optical frequencies when assaying the first biological sample. The system can comprise one or more computer processors (or one or more processing units) operatively coupled to the analytic device. The one or more computer processors can be individually or collectively programmed to receive, over a network, one or more instructions from a remote server. The one or more instructions can be usable by the one or more computer processors to configure the analytic device to output data corresponding to the second set of optical frequencies. The one or more computer processors can be individually or collectively programmed to use the one or more instructions to configure the analytic device such that the analytic device outputs data corresponding to the first set of optical frequencies and the second set of optical frequencies when assaying a second biological sample.

The analytic device can comprise a housing with a volume that is less than about 1,500 cubic centimeters. The analytic device can comprise at least one heating block within the housing. The at least one heating block can comprise a recess configured to receive an assay tube. The assay tube can be configured to receive a biological sample. The analytic device can comprise at least one heating unit in thermal communication with the at least one heating block. The at least one heating unit can provide thermal energy to the assay tube through the at least one heating block. The at least one heating unit can comprise a resistive heater. The at least one heating unit can be thermally cured to the at least one heating block, and/or soldered to the at least one heating block. The analytic device can further comprise a cooling unit disposed within the housing. The cooling unit can reduce the thermal energy from the assay tube.

The first set of optical frequencies can comprise a first color and the second set of optical frequencies can comprise a second color different than the first color.

The analytic device can comprise a lighting unit. The lighting unit can comprise at least one light path comprising an excitation filter and an emission filter. The at least one light path may be configured to provide excitation energy from a light source to the assay tube (or the biological sample contained therein). The at least one light path can comprise one or more light pipes to convey the excitation energy from the light source to the biological sample. The one or more light pipes can comprise a first end comprising a single pipe, a second end comprising two or more pipes, and a branching portion therebetween.

The analytic device can comprise a lighting unit comprising a plurality of light sources configured to provide excitation energy at a plurality of different frequencies or frequency ranges. The lighting unit can be configured to bring a light source of the plurality of light sources in optical alignment with a light path that is in optical communication with the assay tube (or the biological sample contained therein). The light source can be configured to provide light at a frequency or frequency range from the plurality of different frequencies or frequency ranges. The lighting unit can be rotatable along an axis. The lighting unit can be translatable along an additional axis orthogonal to the axis. The lighting unit can be translatable along the additional axis to remove the light path from alignment with the assay tube.

The analytic device can comprise a movable carriage comprising an excitation filter and an emission filter. The movable carriage can be configured to translate to bring the excitation filter and the emission filter to a first position in alignment with a light path that provides excitation energy from the excitation source to the assay tube (or the biological sample contained therein). The movable carriage can comprise a plurality of light paths. The analytic device can further comprise an actuator for moving the movable carriage from the first position to a second position.

The light source can be an excitation source. The excitation source can comprise one or more light emitting diodes (LEDs). The one or more LEDs can comprise single-color LEDs. The one or more LEDs can comprise a plurality of LEDs, and each of the plurality of LEDs can be configured to emit a different frequency of the excitation energy.

The system can further comprise a mobile electronic device. The mobile electronic device can be external to the housing of the analytic device. The one or more computer processors can be configured to communicate with the mobile electronic device. The analytic device can further comprise a communication unit that provides wireless connection between the one or more computer processors and the mobile electronic device. The wireless connection can be a WiFi connection, a Bluetooth connection, a Bluetooth LE connection, an ANT+ connection, or a Gazell connection. The one or more computer processors can be individually or collectively programmed to direct a request to the remote server for the one or more instructions. The mobile electronic device can be configured to direct the request to the remote server for the one or more instructions, and/or receive the one or more instructions from the remote server. The mobile electronic device can be configured to send instructions to the one or more computer processors to configure the analytic device upon receiving the one or more instructions. The one or more computer processors can be configured to receive instructions from the mobile electronic device for processing a biological sample. In response to the instructions, the one or more computer processors can be used to direct the at least one heating unit to provide thermal energy to the at least one heating block to provide heat to the biological sample, and/or direct the excitation source to provide the excitation energy.

The one or more computer processors can be individually or collectively programmed to configure the analytic device such that the analytic device outputs data corresponding to at least the first set of optical frequencies, the second set of optical frequencies and a third set of optical frequencies when assaying a second biological sample, wherein the third set of optical frequencies can be different than the first set of optical frequencies and the second set of optical frequencies.

Samples

A variety of samples (e.g., biological samples) may be analyzed. A sample may be obtained invasively (e.g., tissue biopsy) or non-invasively (e.g., venipuncture). The sample may be an environmental sample. The sample may be a water sample (e.g., a water sample obtained from a lake, stream, river, estuary, bay, or ocean). The sample may be a soil sample. The sample may be a tissue or fluid sample from a subject, such as saliva, semen, blood (e.g., whole blood), serum, synovial fluid, tear, urine, or plasma. The sample may be a tissue sample, such as a skin sample or tumor sample. The sample may be obtained from a portion of an organ of a subject. The sample may be a cellular sample. The sample may be a cell-free sample (e.g., a plasma sample comprising cell-free analytes or nucleic acids). A sample may be a solid sample or a liquid sample. A sample may be a biological sample or a non-biological sample. A sample may comprise an in-vitro sample or an ex-vivo sample. Non-limiting examples of a sample include an amniotic fluid, bile, bacterial sample, breast milk, buffy coat, cells, cerebrospinal fluid, chromatin DNA, ejaculate, nucleic acids, plant-derived materials, RNA, saliva, semen, blood, serum, soil, synovial fluid, tears, tissue, urine, water, whole blood or plasma, and/or any combination and/or any fraction thereof. In one example, the sample may be a plasma sample that may comprise DNA. In another example, the sample may comprise a cell sample that may comprise cell-free DNA.

A sample may be a mammalian sample. For example, a sample may be a human sample. Alternatively, a sample may be a non-human animal sample. Non-limiting examples of a non-human sample include a cat sample, a dog sample, a goat sample, a guinea pig sample, a hamster sample, a mouse sample, a pig sample, a non-human primate sample (e.g., a gorilla sample, an ape sample, an orangutan sample, a lemur sample, or a baboon sample), a rat sample, a sheep sample, a cow sample, and a zebrafish sample.

The devices and methods disclosed herein may be useful for analyzing nucleic acids (e.g., circulating and/or cell-free DNA fragments). Nucleic acids may be derived from eukaryotic cells, prokaryotic cells, or non-cellular sources (e.g., viral particles). A nucleic acid may refer to a substance whose molecules consist of many nucleotides linked in a long chain. Non-limiting examples of the nucleic acid include an artificial nucleic acid analog (e.g., a peptide nucleic acid, a morpholino oligomer, a locked nucleic acid, a glycol nucleic acid, or a threose nucleic acid), chromatin, mRNA, cDNA, DNA, single stranded DNA, double stranded DNA, genomic DNA, plasmid DNA, or RNA. A nucleic acid may be double stranded or single stranded. A sample may comprise a nucleic acid that may be intracellular. Alternatively, a sample may comprise a nucleic acid that may be extracellular (e.g., cell-free). A sample may comprise a nucleic acid (e.g., chromatin) that may be fragmented.

Assays

An assay may comprise nucleic acid amplification. For example, any type of nucleic acid amplification reaction may be used to amplify a target nucleic acid and generate an amplified product. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction, ligase chain reaction, asymmetric amplification, rolling circle amplification, and multiple displacement amplification (MDA). The amplified product may be DNA. In cases where a target RNA is amplified, DNA may be obtained by reverse transcription of the RNA and subsequent amplification of the DNA may be used to generate an amplified DNA product. The amplified DNA product may be indicative of the presence of the target RNA in the biological sample. In cases where DNA is amplified, various DNA amplification methods may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). DNA amplification may be linear. Alternatively, DNA amplification may be exponential. DNA amplification may be achieved with nested PCR, which may improve sensitivity of detecting amplified DNA products. Nucleic acid amplification may be isothermal. Non-limiting examples of isothermal nucleic acid amplification methods include helicase-dependent amplification, nicking enzyme amplification, recombinase polymerase amplification, loop-mediated isothermal amplification, and nucleic acid sequence based amplification.

Nucleic acid amplification reactions may be conducted in assay tubes in parallel. Nucleic acid amplification reactions may be conducted, for example, by including reagents necessary for each nucleic acid amplification reaction in a reaction vessel to obtain a reaction mixture and subjecting the reaction mixture to conditions necessary for each nucleic amplification reaction. Reverse transcription amplification and DNA amplification may be performed sequentially, such as, for example, performing reverse transcription amplification on RNA to generate complementary DNA (cDNA), and subsequently subjecting the cDNA to DNA amplification (e.g., PCR) to amplify the cDNA.

A nucleic acid sample may be amplified using reagents directed to a given target, such as, for example, a primer having sequence complementarity with a target sequence. After multiple heating and cooling cycles, any amplification products may be detected optically, such as using fluorophores. Fluorophore-labeled primers or hybridization probes and/or fluorescent dyes that bind to DNA maybe excited, and an emitted fluorescence detected. Detection may comprise analyzing fluorescence emission from a dye and calculating the ratio of fluorophore emission to dye emission. A primer may comprise a fluorophore and a quencher. In some cases, a tertiary structure of an unbound primer may be such that a quencher may be in close enough proximity to a fluorophore to prevent excitation of the fluorophore and/or the detection of an emission signal from the fluorophore.

In one example, a fluorescent DNA dye, such as SYBR Green I, may be added to a mixture containing a target nucleic acid and at least one amplification primer. In other examples, an amplification primer may be a linear single-stranded oligonucleotide that is extendable by a DNA polymerase and that is labeled with an excitable fluorophore. Upon performing an amplification reaction, such as, e.g., PCR, that includes annealing and extending the labeled primer, the fluorophore may be excited and a resultant emission detected during the amplification reaction (e.g., real-time detection) or following completion of the amplification reaction (e.g., an end-point detection at the conclusion of the amplification reaction or during a subsequent thermal analysis (melting curve)). Unincorporated primers may not fluoresce.

The thermal analysis may be melting curve analysis. The melting curve analysis can be an assessment of the dissociation characteristics of double-stranded DNA during heating. During the melting curve analysis, the nucleic acid sample can be heated across a range of temperatures. The thermal analysis may be high resolution melt (HRM) analysis. The HRM analysis can be used to detect mutations, polymorphisms, and epigenetic differences in nucleic acid samples, e.g., double-stranded DNA samples. Intercalating dyes that can be used with the HRM analysis include, but are not limited to, SYTO 9, LC Green, Chromofy, BEBO, SYBR Green, and Eva Green. The intercalating dye used for HRM analysis can be in high amount or saturating concentration. In some cases, the nucleic acid sample is amplified first using polymerase chain reaction (PCR) prior to HRM analysis to generate amplification products. The amplification can be performed to amplify the region in which the mutation of interest lies. During HRM analysis, the nucleic acid sample or amplification products can be heated from about 40° C. up to about 100° C., from about 50° C. up to about 95° C., from 55° C. up to about 98° C., from 60° C. up to about 95° C., or from 60° C. up to about 100° C. The temperature within a given range can be increased or decreased in increments, for example, at least about 0.1° C., 0.2° C., 0.3° C., 0.4° C., 0.5° C., 0.6° C., 0.7° C., 0.8° C., 0.9° C., 1.0° C., or greater. At each temperature, the nucleic acid sample can be heated for at least about 5 seconds, 6 seconds, 7 seconds, 8 seconds, 9 seconds, 10 seconds, 11 seconds, 12 seconds, 13 seconds, 14 seconds, 15 seconds, or more. A fluorescent signal can be monitored in real time during HRM analysis when the temperature is increased or decreased.

A wide range of fluorophores and/or dyes may be used in primers or melting curve analysis according to the present disclosure. Available fluorophores include coumarin; fluorescein; tetrachlorofluorescein; hexachlorofluorescein; Lucifer yellow; rhodamine; BODIPY; tetramethylrhodamine; Cy3; Cy5; Cy7; eosine; Texas red; SYBR Green I; SYBR Gold; 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'- dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl) azo)benzoic acid) Cy5 (Indodicarbocyanine-5) Cy3 (Indo-dicarbocyanine-3); BODIPY FL (2,6-dibromo-4,4-difluoro-5,7-dimethyl-4-bora-3a,4a-diaza-s-indacene-3-proprionic acid); Quasar-670 (Bioreseach Technologies); CalOrange (Bioresearch Technologies); and Rox as well as suitable derivatives thereof. Combination fluorophores such as fluorescein-rhodamine dimers may also be suitable. Fluorophores may be chosen to absorb and emit in the visible spectrum or outside the visible spectrum, such as in the ultraviolet or infrared ranges. Suitable quenchers may also include DABCYL and variants thereof, such as DABSYL, DABMI and Methyl Red. Fluorophores may also be used as quenchers, because they tend to quench fluorescence when touching certain other fluorophores. Preferred quenchers may be chromophores such as DABCYL or malachite green, or fluorophores that may not fluoresce in the detection range when the probe is in the open conformation.

Allele-discriminating probes useful according to the invention also include probes that bind less effectively to a target-like sequence, as compared to a target sequence. The change in the level of fluorescence in the presence or absence of a target sequence compared to the change in the level of fluorescence in the presence or absence of a target-like sequence may provide a measure of the effectiveness of binding of a probe to a target or target-like sequence.

DNA generated from reverse transcription of the RNA may be amplified to generate an amplified DNA product. Any suitable number of nucleic acid amplification reactions may be conducted. In some cases, at least about 1, 2, 3, 4, 5, 6, 7, 8, 9, 10, 11, 12, 13, 14, 15, 16, 17, 18, 19, 20, or more nucleic acid amplification reactions are conducted.

For example, a target nucleic acid (e.g., target RNA, target DNA) may be extracted or released from a biological sample during heating phases of nucleic acid amplification. In the case of a target RNA, for example, the biological sample comprising the target RNA may be heated and the target RNA released from the biological sample. The released target RNA may begin reverse transcription (via reverse transcription amplification) to produce complementary DNA. The complementary DNA may then be amplified.

Primer sets directed to a target nucleic acid may be utilized to conduct nucleic acid amplification reaction. Primer sets may comprise one or more primers. For example, a primer set may comprise at least 1, 2, 3, 4, 5, 6, 7, 8, 9, 10, or more primers. A primer set may comprise primers directed to different amplified products or different nucleic acid amplification reactions. For example, a primer set may comprise a first primer necessary to generate a first strand of nucleic acid product that is complementary to at least a portion of the target nucleic acid and a second primer complementary to the nucleic acid strand product necessary to generate a second strand of nucleic acid product that is complementary to at least a portion of the first strand of nucleic acid product.

In cases in which a plurality of assay tubes is used, the plurality of assay tube may include the same primers or primer sets, or different primers or primer sets. Each assay tube may be directed to a different target, or at least a subset of the assay tubes may be directed to the same target.

For example, a primer set may be directed to a target RNA. The primer set may comprise a first primer that may be used to generate a first strand of nucleic acid product that is complementary to at least a portion the target RNA. In the case of a reverse transcription reaction, the first strand of nucleic acid product may be DNA. The primer set may also comprise a second primer that may be used to generate a second strand of nucleic acid product that is complementary to at least a portion of the first strand of nucleic acid product. In the case of a reverse transcription reaction conducted with DNA amplification, the second strand of nucleic acid product may be a strand of nucleic acid (e.g., DNA) product that is complementary to a strand of DNA generated from an RNA template.

Any suitable number of primer sets may be used. For example, at least about 1, 2, 3, 4, 5, 6, 7, 8, 9, 10, or more primer sets may be used. Where multiple primer sets are used, one or more primer sets may each correspond to a particular nucleic acid amplification reaction or amplified product.

A DNA polymerase may also be used. Any suitable DNA polymerase may be used, including commercially available DNA polymerases. A DNA polymerase may refer to an enzyme that is capable of incorporating nucleotides to a strand of DNA in a template bound fashion. Non-limiting examples of DNA polymerases include Taq polymerase, Tth polymerase, Tli polymerase, Pfu polymerase, VENT polymerase, DEEPVENT polymerase, EX-Taq polymerase, LA-Taq polymerase, Expand polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, and variants, modified products, and derivatives thereof. A "hot start" polymerase may be used, e.g., in an amplification reaction. For certain "hot start" polymerases, a denaturation step at about 94° C.-95° C. for about 2 minutes to 10 minutes may be used, which may change the thermal profile based on different polymerases.

Figure 12A:
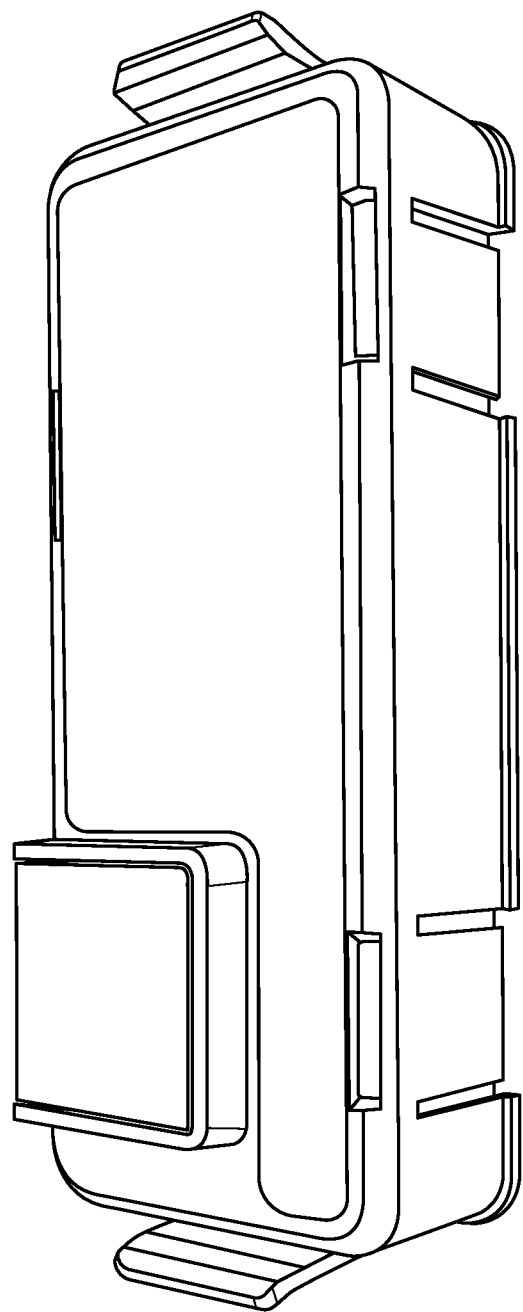
FIG. 12A shows an example cartridge that can be inserted into the analytic device for sample testing. The cartridge can contain one or more reagents to be used for nucleic acid amplification (e.g., polymerase chain reaction (PCR)).
Figure 12B:
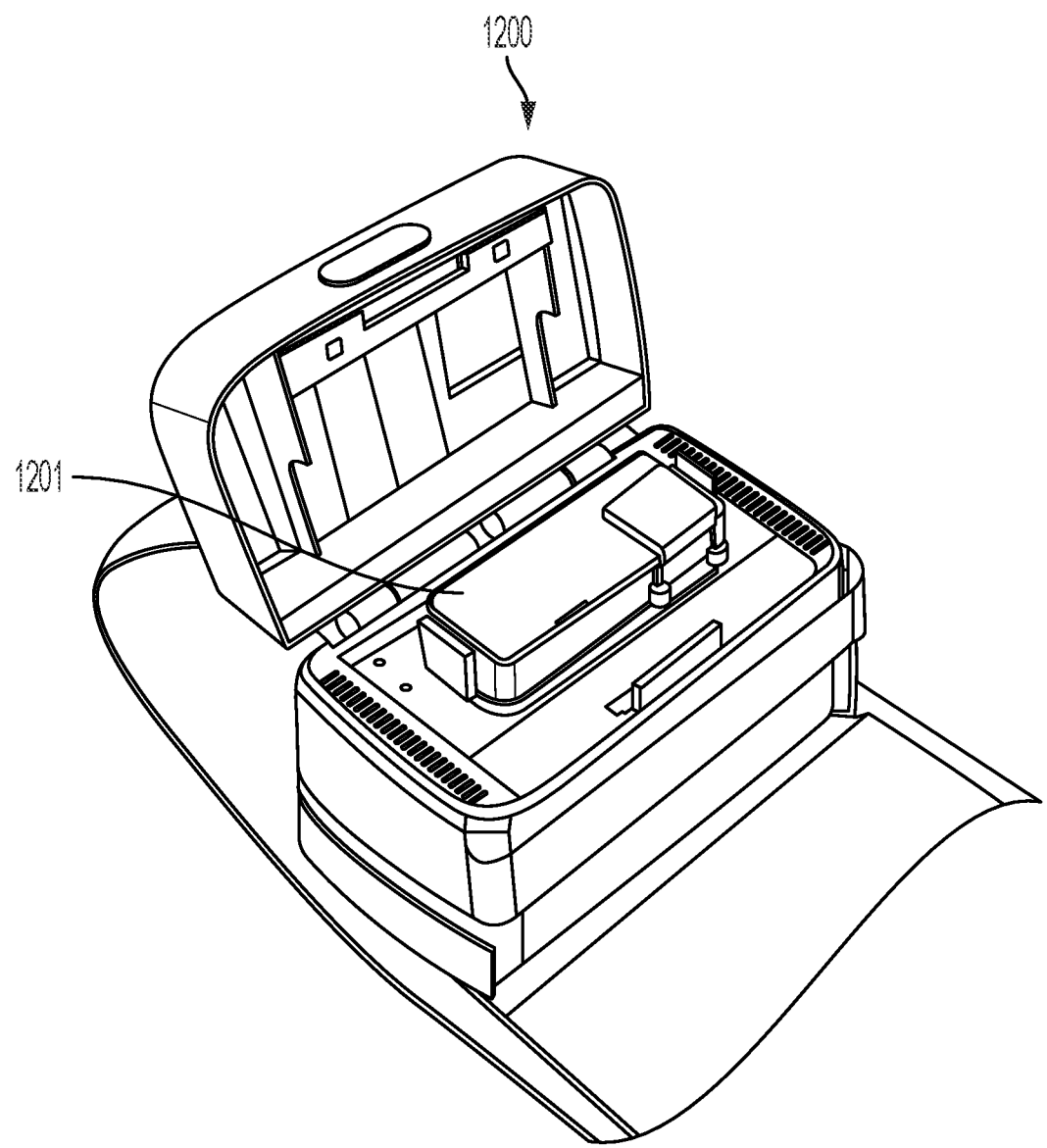
FIG. 12B shows an example cartridge inserted into the housing of the analytic device.

The reagents used for assays (e.g., thermocycling reactions or nucleic acid amplifications) can be provided in a reagent cartridge. The reagent cartridge can be premixed or prepacked. The reagent cartridge can be prepacked and ready for use. The reagent cartridge can be designed for different targets, for example, by containing primers specific for a given target or given targets. For example, the reagent cartridge can be designed for targeting microorganisms that cause a disease. In some embodiments, the reagent cartridge is designed for targeting nucleic acids from one or more microorganisms that cause fever or flu. In some embodiments, the reagent cartridge is designed for targeting nucleic acids from one or more viruses that cause fever or flu. In some embodiments, the reagent cartridge is designed for targeting nucleic acids from one or more microorganisms that cause an infectious disease. In some embodiments, the reagent cartridge is designed for targeting one or more microorganisms present in a sample. In some embodiments, the reagent cartridge is designed for targeting one or more microorganisms present in an environmental sample. The reagent cartridge can comprise a chamber for sample loading. An example cartridge is shown in FIG. 12A. The example cartridge 1201 can be inserted into the housing 1200 of the analytic device, for example, as shown in FIG. 12B.

The reagent cartridge can be stable and have a long shelf life. For example, the reagent cartridge can be stable at ambient condition or have a shelf life of at least about 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, or 30 months. For another example, the reagent cartridge can be stable at ambient condition or have a shelf life of at least 1 year, 1.5 years, 2 years, 2.5 years, 3 years, 4 years, 5 years, or longer.

In some cases, the reagent used for assays can be divided into two parts, a dry part and a wet (e.g., liquid) part. The dry part can be provided in a reagent cartridge as described herein. The wet part can be provided in the device during an assay. The dry part and the wet part can be mixed in the device when performing an assay.

In some embodiments, the wet part can be provided in a reagent cartridge as described herein. The dry part can be provided in the device during an assay. The dry part and the wet part can be mixed in the device when performing an assay.

In some embodiments, both the dry part and the wet part can be provided in a reagent cartridge without contacting or mixing with each other. In some embodiments, both the dry part and the wet part can be provided in separate reagent cartridges.

In some embodiments, the dry part and the wet part can be premixed before inserting into the device. In some embodiments, the dry part and the wet part can be inserted into the device and then mixed in the device.

When a wet reagent is provided in a reagent cartridge, the reagent cartridge can be sealed. In some embodiments, the reagent cartridge containing the wet reagent can be sealed by laser welding. Other methods to seal the reagent cartridge include, but are not limited to, using foil, membrane, film, or valve.

Using the device and reagent described in the present disclosure, the assay can be performed in various conditions. For example, the assay can be performed in various vibration conditions, dust levels, humidity levels, or altitudes. In some embodiments, the assay can be performed at normal ambient condition. For example, the normal ambient condition may have a temperature of about 25° C. and a pressure of about 100 kilopascal (kPa). In some other embodiments, the assay can be performed in a condition deviated from a normal ambient condition. In some cases, the assay can be performed at a pressure of at least about 10 kPa, 20 kPa, 30 kPa, 40 kPa, 50 kPa, 60 kPa, 70 kPa, 80 kPa, 90 kPa, 100 kPa, 105 kPa, 110 kPa, 120 kPa, 130 kPa, or more. In some cases, the assay can be performed at a pressure of at most about 70 kPa, 60 kPa, 50 kPa, 40 kPa, 30 kPa, 20 kPa, or 10 kPa. In some cases, the assay can be performed at an altitude above sea level. The altitude above sea level can be at least about 500 feet, 1000 feet, 1500 feet, 2000 feet, 2500 feet, 3000 feet, 3500 feet, 4000 feet, 4500 feet, 5000 feet, 6000 feet, 7000 feet, 8000 feet, 9000 feet, 10000 feet, 15000 feet, 20000 feet, 30000 feet, 40000 feet, 50000 feet, or more. The assay described herein may be performed in space.

The assay described herein can be performed at various humidity levels. As used herein, absolute humidity (units are grams of water vapor per cubic meter volume of air) is a measure of the actual amount of water vapor in the air, regardless of the air's temperature. The higher the amount of water vapor, the higher the absolute humidity. For example, a maximum of about 30 grams of water vapor can exist in a cubic meter volume of air with a temperature of about 85° F. As used herein, relative humidity, expressed as a percent, is a measure of the amount of water vapor that air is holding compared to the amount it can hold at a specific temperature. Warm air can possess more water vapor (moisture) than cold air. For example, a relative humidity of 50% means that the air holds on that day (at a specific temperature) about 50% of the water needed for the air to be saturated. Saturated air has a relative humidity of 100%. In some embodiments, the assay can be performed at a humidity level with a relative humidity of at least about 10%, 20%, 30%, 40%, 50%, 60%, 80%, 70%, 90%, 95%, 98%, or more.

Figure 22A:
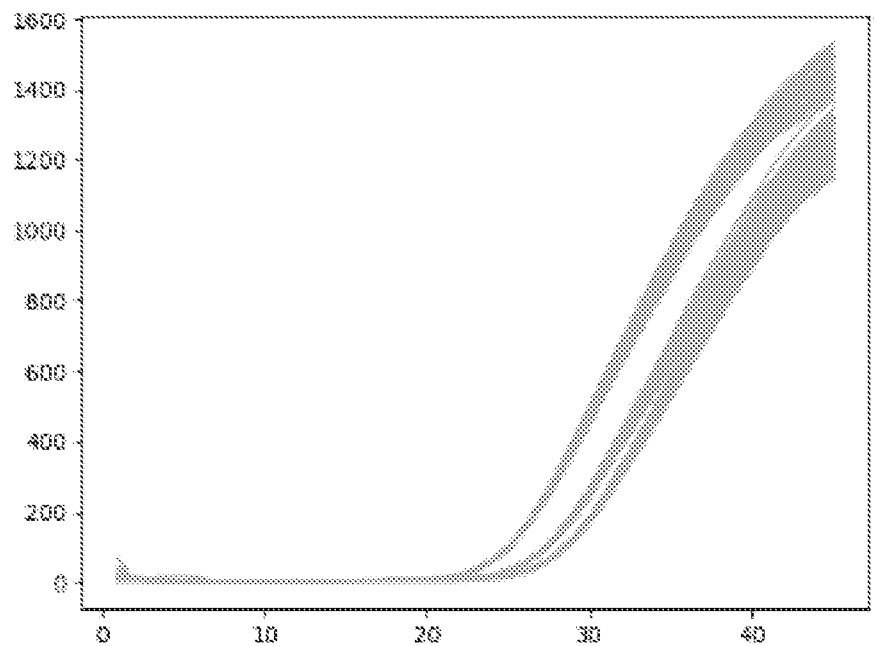
FIG. 22A shows experimental data of nucleic acid amplification using a portable analytic device of the present disclosure.
Figure 22B:
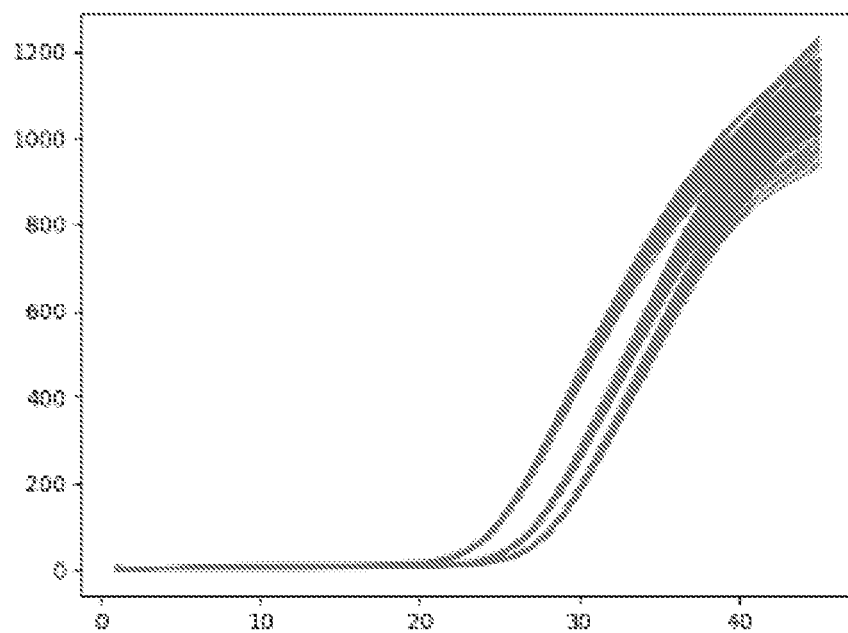
FIG. 22B shows other experimental data of nucleic acid amplification using the portable analytic device.
Figure 22C:
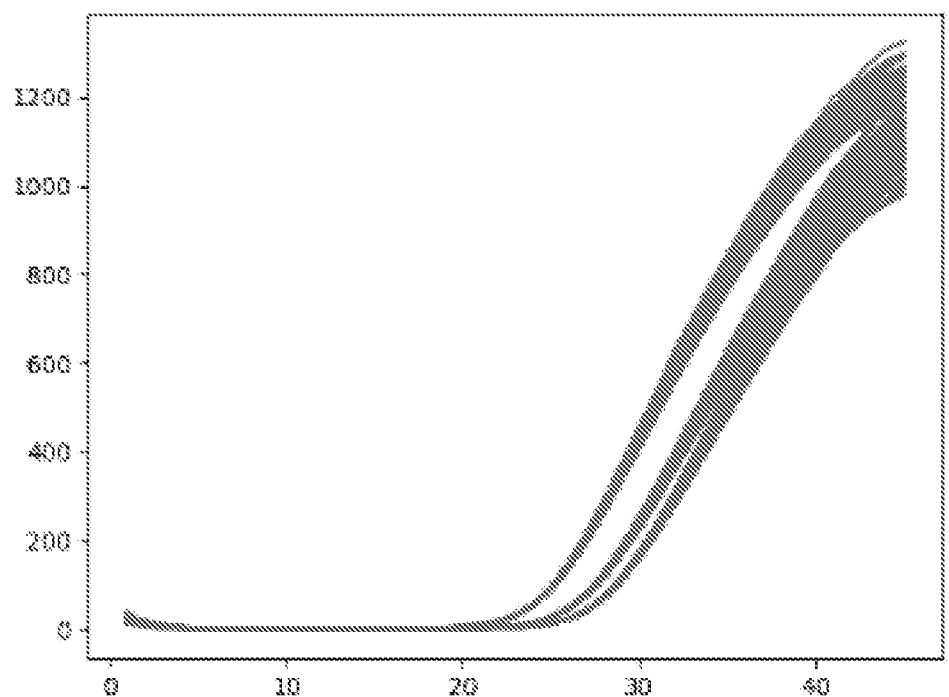
FIG. 22C shows other experimental data of nucleic acid amplification using the portable analytic device.
Figure 22D:
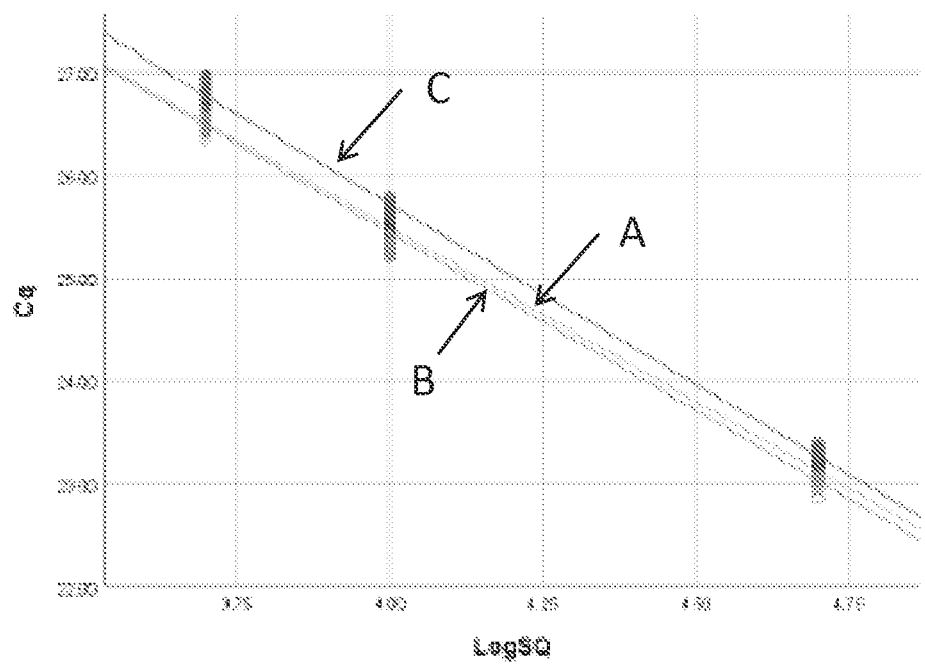
FIG. 22D shows a Cq versus LogSQ plot of the experimental data from FIGS. 22A-22C.

FIGS. 22A-22D show example nucleic acid amplification data obtained using the portable analytic device described herein. FIG. 22A shows amplification plot on the portable analytic device described herein from multiplexed reactions using a synthetic DNA target at 50,000, 10,000 and 5,000 copies/reaction using Texas Red-X. FIG. 22B shows amplification plot on the portable analytic device described herein from multiplexed reactions using a synthetic DNA target at 50,000, 10,000 and 5,000 copies/reaction using FAM. FIG. 22C shows amplification plot on the portable analytic device described herein from multiplexed reactions using a synthetic DNA target at 50,000, 10,000 and 5,000 copies/reaction using ATTO647n. All nine wells in the system were run with each concentration 4 times, for a total n=36 per concentration (n=108 per fluorophore). FIG. 22D shows Linear Regression Curve of Cq vs. Log(SQ) (Sq=Starting Quantity) with synthetic DNA target at 50,000, 10,000 and 5,000 copies/reaction [n=36 per concentration (4 runs×9 wells per concentration), n=108 per fluorophore]. The curve A shows a plot using the data obtained in FIG. 22A ($R^2=0.995$). The curve B shows a plot using the data obtained in FIG. 22B ($R^2=0.996$). The curve C shows a plot using the data obtained in FIG. 22C ($R^2=0.996$).

Computer Systems

Figure 11:
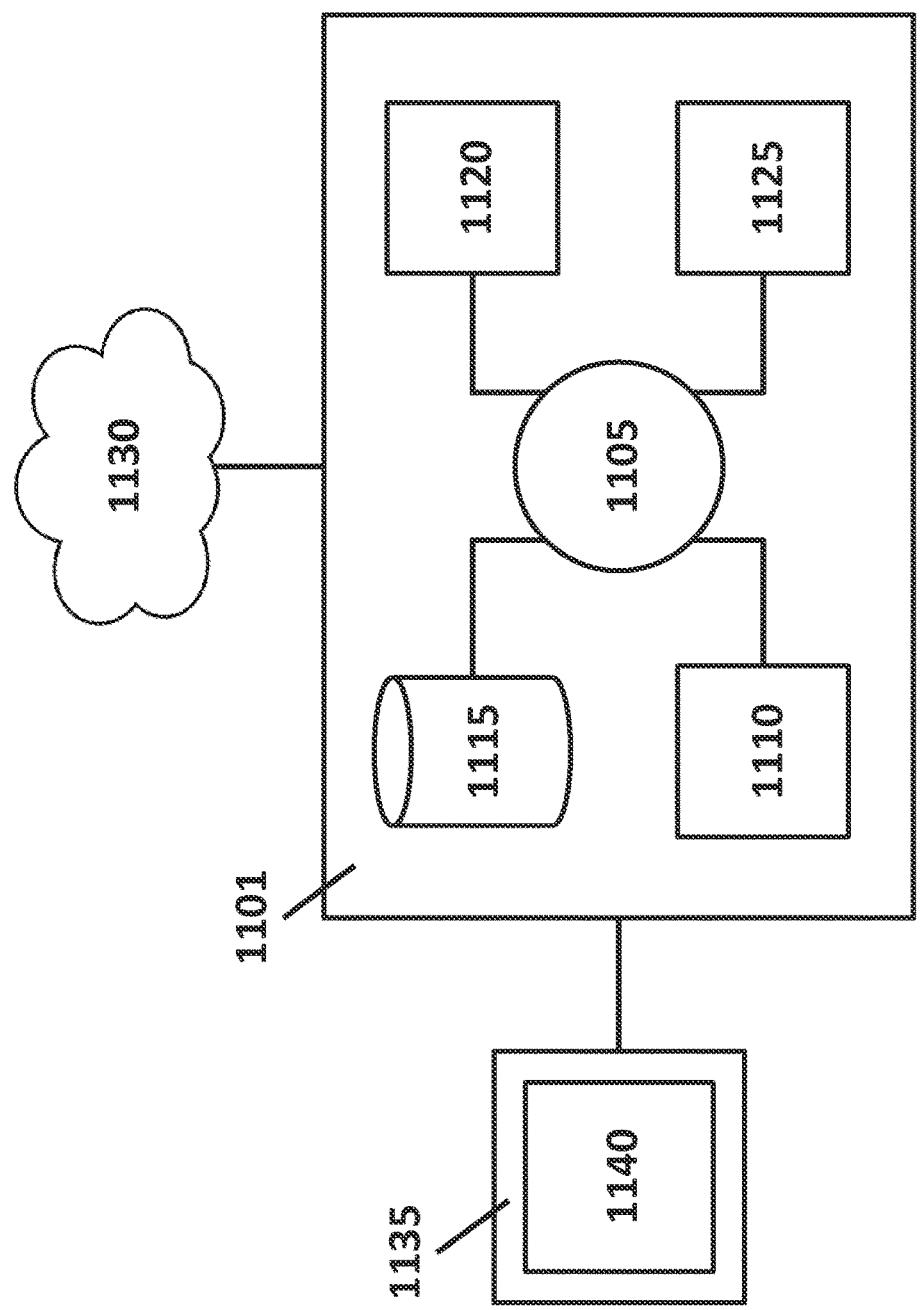
FIG. 11 shows a computer system that is programmed or otherwise configured to implement methods provided herein.

The present disclosure provides computer systems that are programmed to implement methods of the disclosure. FIG. 11 shows a computer system 1101 that is programmed or otherwise configured to analyze a sample. The computer system 1101 may regulate some aspects of the analytic device of the present disclosure, such as, for example, movement of a moving carriage, heating or cooling of a heating block, and/or activation/deactivation of an excitation source or detector. The computer system may control of the temperature of a heating block (e.g., through activation of a resistive heater or fan). The computer system 1101 may be integrated into the analytic device of the present disclosure and/or include an electronic device of a user or a computer system that is remotely located with respect to the electronic device. The electronic device may be a mobile electronic device.

The computer system 1101 includes a central processing unit (CPU, also "processor" and "computer processor" herein) 1105, which may be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 may be a data storage unit (or data repository) for storing data. The computer system 1101 may be operatively coupled to a computer network ("network") 1130 with the aid of the communication interface 1120. The network 1130 may be the Internet, an internet and/or extranet, or an intranet and/or extranet that is in communication with the Internet. The network 1130 in some cases is a telecommunication and/or data network. The network 1130 may include one or more computer servers, which may enable distributed computing, such as cloud computing. The network 1130, in some cases with the aid of the computer system 1101, may implement a peer-to-peer network, which may enable devices coupled to the computer system 1101 to behave as a client or a server.

The CPU 1105 may execute a sequence of machine-readable instructions, which may be embodied in a program or software. The instructions may be stored in a memory location, such as the memory 1110. The instructions may be directed to the CPU 1105, which may subsequently program or otherwise configure the CPU 1105 to implement methods of the present disclosure. Examples of operations performed by the CPU 1105 may include fetch, decode, execute, and writeback.

The CPU 1105 may be part of a circuit, such as an integrated circuit. One or more other components of the system 1101 may be included in the circuit. In some cases, the circuit is an application specific integrated circuit (ASIC).

The storage unit 1115 may store files, such as drivers, libraries and saved programs. The storage unit 1115 may store user data, e.g., user preferences and user programs. The computer system 1101 in some cases may include one or more additional data storage units that are external to the computer system 1101, such as located on a remote server that is in communication with the computer system 1101 through an intranet or the Internet.

The computer system 1101 may communicate with one or more remote computer systems through the network 1130. For instance, the computer system 1101 may communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user may access the computer system 1101 via the network 1130.

Methods as described herein may be implemented by way of machine (e.g., computer processor) executable code stored on an electronic storage location of the computer system 1101, such as, for example, on the memory 1110 or electronic storage unit 1115. The machine executable or machine readable code may be provided in the form of software. During use, the code may be executed by the processor 1105. In some cases, the code may be retrieved from the storage unit 1115 and stored on the memory 1110 for ready access by the processor 1105. In some situations, the electronic storage unit 1115 may be precluded, and machine-executable instructions are stored on memory 1110.

The code may be pre-compiled and configured for use with a machine having a processer adapted to execute the code, or may be compiled during runtime. The code may be supplied in a programming language that may be selected to enable the code to execute in a pre-compiled or as-compiled fashion.

Aspects of the systems and methods provided herein, such as the computer system 1101, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 may include or be in communication with an electronic display 1135 that comprises a user interface (UI) 1140 for providing, for example, a current stage of processing of a sample (e.g., a particular step, such as a lysis step, that is being performed). Examples of UI's include, without limitation, a graphical user interface (GUI) and web-based user interface.

Methods and systems of the present disclosure may be implemented by way of one or more algorithms. An algorithm may be implemented by way of software upon execution by the central processing unit 1105.

Methods and systems of the present disclosure may be combined with or modified by other methods or systems, such as, for example, those described in U.S. Pat. No. 9,579,655, which is entirely incorporated herein by reference.

Certain inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, or within 2-fold, of a value. Where particular values are described in the application and claims, unless otherwise stated the term "about" meaning within an acceptable error range for the particular value may be assumed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for biological sample assaying, comprising:
an analytic device comprising an optical detector configured to detect optical signals from a first biological sample over a plurality of optical frequencies comprising a first set of optical frequencies and a second set of optical frequencies different than said first set of optical frequencies, wherein said analytic device is programmed to output data corresponding to said first set of optical frequencies and locked with respect to outputting data corresponding to said second set of optical frequencies such that said analytic device does not output said data corresponding to said second set of optical frequencies when assaying said first biological sample; and
one or more computer processors operatively coupled to said analytic device, wherein said one or more computer processors are individually or collectively programmed to (i) receive, over a network, one or more instructions from a remote server, which one or more instructions cause said one or more computer processors to program said analytic device to be unlocked with respect to outputting data corresponding to said second set of optical frequencies such that said analytic device outputs said data corresponding to said second set of optical frequencies, and (ii) use said one or more instructions to program said analytic device such that said analytic device outputs data corresponding to said first set of optical frequencies and said second set of optical frequencies when assaying a second biological sample.

2. The system of claim 1, further comprising a housing, wherein said analytic device and said one or more computer processors are within said housing.

3. The system of claim 2, wherein said analytic device further comprises a cooling unit disposed within said housing, which cooling unit reduces said thermal energy from said assay tube.

4. The system of claim 1, further comprising a housing, wherein said analytic device is within said housing, and wherein said one or more computer processors are external to said housing.

5. The system of claim 1, wherein said analytic device comprises a housing with a volume that is less than about 1,500 cubic centimeters.

6. The system of claim 5, wherein said analytic device comprises at least one heating block within said housing, said at least one heating block comprising a recess configured to receive an assay tube comprising said first or second biological sample.

7. The system of claim 6, wherein said analytic device comprises at least one heating unit in thermal communication with said at least one heating block, which at least one heating unit provides thermal energy to said assay tube through said at least one heating block.

8. The system of claim 7, wherein said at least one heating unit comprises a resistive heater.

9. The system of claim 8, wherein said at least one heating unit is (i) thermally cured to said at least one heating block, or (ii) soldered to said at least one heating block.

10. The system of claim 1, wherein said first set of optical frequencies comprises a first color and said second set of optical frequencies comprises a second color different than said first color.

11. The system of claim 1, wherein said analytic device comprises a lighting unit, which lighting unit comprises at least one light path comprising an excitation filter and an emission filter, wherein said at least one light path is configured to provide excitation energy from a light source to said first or second biological sample.

12. The system of claim 11, wherein said at least one light path comprises one or more light pipes to convey said excitation energy from said light source to said first or second biological sample.

13. The system of claim 12, wherein said one or more light pipes comprise a first end comprising a single pipe, a second end comprising two or more pipes, and a branching portion therebetween.

14. The system of claim 1, wherein said analytic device comprises a lighting unit comprising a plurality of light sources configured to provide excitation energy at a plurality of different frequencies or frequency ranges, wherein said lighting unit is configured to bring a light source of said plurality of light sources in optical alignment with a light path that is in optical communication with said first or second biological sample, which light source is configured to provide light at a frequency or frequency range from said plurality of different frequencies or frequency ranges.

15. The system of claim 14, wherein said lighting unit is rotatable along an axis.

16. The system of claim 15, wherein said lighting unit is translatable along an additional axis orthogonal to said axis, wherein said lighting unit is translatable along said additional axis to remove said light path from alignment with said first or second biological sample.

17. The system of claim 1, wherein said analytic device comprises a movable carriage comprising an excitation filter and an emission filter, wherein said movable carriage is configured to translate to bring said excitation filter and said emission filter to a first position in alignment with a light path that provides excitation energy from said excitation source to said first or second biological sample.

18. A method for programming an analytic device, comprising:
- (a) providing said analytic device comprising an optical detector configured to detect optical signals from a first biological sample over a plurality of optical frequencies comprising a first set of optical frequencies and a second set of optical frequencies different than said first set of optical frequencies, wherein said analytic device is programmed to output data corresponding to said first set of optical frequencies and locked with respect to outputting data corresponding to said second set of optical frequencies such that said analytic devices does not output said data corresponding to said second set of optical frequencies when assaying said first biological sample;
- (b) receiving, over a network, one or more instructions from a remote server, which one or more instructions program said analytic device to be unlocked with respect to outputting data corresponding to said second set of optical frequencies such that said analytic device outputs said data corresponding to said second set of optical frequencies; and
- (c) using said analytic device to output data corresponding to at least said first set of optical frequencies and said second set of optical frequencies when assaying a second biological sample.

19. The method of claim 18, wherein said analytic device comprises a housing.

20. The method of claim 19, wherein said analytic device comprises at least one heating block within said housing, said at least one heating block comprising a recess configured to receive an assay tube comprising said first or second biological sample.

21. The method of claim 20, wherein said analytic device comprises at least one heating unit in thermal communication with said at least one heating block, which at least one heating unit provides thermal energy to said assay tube through said at least one heating block.

22. The method of claim 21, wherein said at least one heating unit comprises a resistive heater.

23. The method of claim 22, wherein said at least one heating unit is (i) thermally cured to said at least one heating block, or (ii) soldered to said at least one heating block.

24. The method of claim 23, wherein said analytic device further comprises a cooling unit disposed within said housing, which cooling unit reduces said thermal energy from said assay tube.

* * * * *